United States Patent [19]

Sato

[11] 4,338,322

[45] Jul. 6, 1982

[54] 1,4-DIHYDROPYRIDINE DERIVATIVES, PHARMACEUTICAL COMPOSITIONS CONTAINING SAME AND METHODS OF EFFECTING VASODILATION USING SAME

[75] Inventor: Yoshinari Sato, Takaishi, Japan

[73] Assignee: Fujisawa Pharmaceutical Co., Ltd., Osaka, Japan

[21] Appl. No.: 180,905

[22] Filed: Aug. 25, 1980

Related U.S. Application Data

[60] Division of Ser. No. 39,752, May 17, 1979, Pat. No. 4,284,634, which is a continuation-in-part of Ser. No. 809,788, Jun. 24, 1977, abandoned, which is a continuation-in-part of Ser. No. 701,994, Jul. 1, 1976, Pat. No. 4,145,432.

[30] Foreign Application Priority Data

| Jul. 2, 1975 | [GB] | United Kingdom | 27945/75 |
| Sep. 29, 1975 | [GB] | United Kingdom | 39854/75 |
| Dec. 16, 1975 | [GB] | United Kingdom | 51524/75 |
| Apr. 5, 1976 | [GB] | United Kingdom | 13761/76 |
| Dec. 17, 1976 | [GB] | United Kingdom | 52720/76 |
| Jun. 6, 1978 | [GB] | United Kingdom | 26429/78 |
| Oct. 10, 1978 | [GB] | United Kingdom | 39978/78 |

[51] Int. Cl.$^3$ ............... C07D 213/55; C07D 213/57; A61K 31/455

[52] U.S. Cl. .................................. 424/266; 546/286; 546/287; 546/321

[58] Field of Search ...................... 546/286, 287, 321; 424/266

[56] References Cited

FOREIGN PATENT DOCUMENTS

| 1963188 | 6/1971 | Fed. Rep. of Germany | 546/321 |
| 2248150 | 4/1974 | Fed. Rep. of Germany | 546/321 |

*Primary Examiner*—Alan L. Rotman
*Attorney, Agent, or Firm*—Dayton R. Stemple

[57] ABSTRACT

This invention relates to 2-or 6-cyano or cyano(lower-)alkyl-4-phenyl or (substituted phenyl)1,4-dihydropyridine-3,5-dicarboxylates and derivatives which have vasodilating and hypertensive activity, processes for their preparation, pharmaceutical compositions for containing same and for methods of treating hypertension and cardiovascular diseases.

27 Claims, No Drawings

1,4-DIHYDROPYRIDINE DERIVATIVES, PHARMACEUTICAL COMPOSITIONS CONTAINING SAME AND METHODS OF EFFECTING VASODILATION USING SAME

This is a division, of application Ser. No. 39,752, filed May 17, 1979, U.S. Pat. No. 4,284,634, which is a continuation-in-part of application Ser. No. 809,788, filed on June 24, 1977, now abandoned, which is a continuation-in-part application of Ser. No. 701,944, filed on July 1, 1976, now U.S. Pat. No. 4,145,432.

This invention relates to 1,4-dihydropyridine derivatives. More particularly, it relates to new 1,4-dihydropyridine derivatives thereof which have vasodilating and anti-hypertensive activity, to processes for the preparation thereof, and to pharmaceutical composition comprising the same for therapeutical treatment in cardiovascular deseases and hypertension in human being.

Accordingly, one object of this invention is to provide new and useful 1,4-dihydropyridine derivatives.

Another object of this invention is to provide processes for the preparation of 1,4-dihydropyridine derivatives.

A further object of this invention is to provide useful pharmaceutical composition comprising said 1,4-dihydropyridine derivatives as a vasodilator and anti-hypertensive.

Still further object of the present invention is to provide a therapeutical method of treating cardiovascular diseases such as coronary insufficiency, angina pectoris or myocardial infarction and hypertension.

The 1,4-dihydropyridine derivatives of this invention may be represented by the general formula:

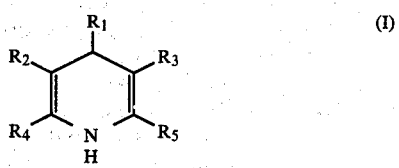

(I)

wherein $R_1$ is aryl which may have one or more suitable substituent(s) or a heterocyclic group, $R_2$ and $R_3$ are each, same or different, esterified carboxy, and $R_4$ and $R_5$ are each hydrogen; cyano; lower alkyl; or substituted lower alkyl in which the substituent is cyano, hydroxy, acyloxy, hydroxyimino, hydrazono, lower alkoxyimino, hydroxy(lower)alkylimino, N'-or N', N'-di-(lower)alkylamino(lower)alkylimino, hydrazino, hydroxy(lower)alkylamino, N'- or N', N'-di-(lower)alkylamino(lower)alkylamino, a 5 or 6-membered saturated N-containing heterocyclic-1-yl which may have hydroxy, lower alkyl or hydroxy(lower)alkyl, or oxo wherein thus formed carbonyl may be protected with suitable protecting group; provided that, when one of $R_4$ and $R_5$ is hydrogen or lower alkyl, the other is always cyano or said substituted lower alkyl, and when $R_4$ and $R_5$ are not hydrogen or lower alkyl, both of them are a group selected from cyano and said substituted lower alkyl, or $R_4$ is hydrogen or lower alkyl and $R_3$ and $R_5$ are combined to form a group of the formula:

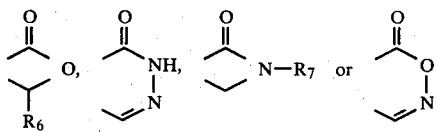

wherein $R_6$ is hydrogen or methyl and $R_7$ is 2-(N,N-diethylamino)ethyl or 2-hydroxyethyl.

The term used in the definitions of the symbols of the general formulae given in this specification and claims are explained as follows:

The term "lower" used in connection with an alkylene, alkyl and alkenyl is intended to mean the one having 1 to 8 carbon atoms.

Aryl and aryl moiety may be phenyl, naphthyl, xylyl, tolyl, mesityl, cumenyl and the like, which may have one or more suitable substituent(s). Preferred examples of the suitable substituent(s) are halogen, nitro, hydroxy, halo(lower)-alkyl, lower alkoxy, lower alkenyloxy, cyano, lower alkoxycarbonyl or lower alkylsulfamoyl. Halogen or halo moiety is fluorine, chlorine, bromine or iodine.

Lower alkylene may be one having a straight or branched and saturated bivalent hydrocarbon chain such as methylene, ethylene, methylmethylene, trimethylene, propylene or tetramethylene.

Lower alkyl and lower alkyl moiety may be ones having a straight or branched and saturated hydrocarbon chain such as methyl, ethyl, propyl, isopropyl, butyl, isobutyl, t-butyl, pentyl, neo-pentyl, hexyl, heptyl or octyl.

Lower alkoxy and lower alkoxy moiety may be methoxy, ethoxy, propoxy, isopropoxy, butyoxy, t-butoxy and pentyloxy.

Halo(lower)alkyl may be mono-halo(lower)alkyl such as chloromethyl, bromomethyl or chloropropyl; di-halo(lower)alkyl such as 1,2-dichloroethyl, 1,2-dibromoethyl or 2,2-dichloroethyl; and tri-halo(lower)alkyl such as trifluoromethyl or 1,2,2-trichloroethyl.

Lower alkenyl and lower alkenyl moiety may be ones having a straight or branched hydrocarbon chain which contains one or more double bond(s), such as vinyl, allyl, butenyl, butanedienyl or penta-2,4-dienyl.

Acyl and acyl moiety may be lower alkanoyl such as formyl, acetyl, propionyl, butyryl, isobutyryl, valeryl, isovaleryl, pivaloyl; substituted lower alkanoyl, for example, carboxy(lower)-alkanoyl, esterified carboxy(lower)alkanoyl such as lower alkoxycarbonyl(lower)alkanoyl, N- or N,N-di-substituted amino(lower)alkanoyl such as N- or N,N-di-(lower)alkylamino(lower)alkanoyl (e.g. N-methyl (or N,N-dimetyl) aminoacetyl, 1(or 2)-[N-ethyl(or N,N-diethyl)amino]propionyl or 1 (or 2)-[N-methyl-N-ethylamino]propionyl) or N-lower alkyl -N-ar(lower)alkylamino(lower)alkanoyl (e.g. 1-(or 2)-[N-methyl-N-benzylamino]propionyl) or aryloxy(lower)alkanoyl such as phenoxyacetyl, tolyloxyacetyl, 2-[2(or 3 or 4)-chlorophenoxyacetyl, 2-[2(or 3 or 4)-chlorophenoxy]-propionyl, 2(or 3 or 4)-nitrophenoxyacetyl or 2(or 3 or 4)-methoxyphenoxyacetyl); aroyl such as benzoyl, naphthoyl or toluoyl and the like.

Lower alkoxycarbonyl may be methoxycarbonyl, ethoxycarbonyl, propoxycarbonyl, isopropoxycarbonyl, butoxycarbonyl, t-butoxycarbonyl and the like.

Lower alkylsulfamoyl may be methylsulfamoyl, ethylsulfamoyl, propylsulfamoyl, isopropylsulfamoyl, butylsulfamoyl, pentylsulfamoyl and the like.

A heterocyclic group for $R_1$ may be an aromatic heterocyclic group containing one or more hetero atom(s) selected form nitrogen atom, sulfur atom and oxygen atom, for example, thienyl, furyl, pyrrolyl, thiazolyl, thiadiazolyl, tetrazolyl, pyridyl, pyrimidinyl, quinolyl, isoquinolyl, benzothienyl, indolyl or purinyl.

Esterifed carboxy for $R_2$ and $R_3$ may be lower alkoxycarbonyl such as methoxycarbonyl, ethoxycarbonyl, propoxycarbonyl, butoxycarbonyl, t-butoxycarbonyl; halo(lower)alkoxycarbonyl such as the halo-analogues of the above-mentioned lower alkoxycarbonyl (e.g., 2-bromoethoxycarbonyl, 2-chloroethoxycarbonyl, 2 (or 3)-chloropropoxycarbonyl, 2 (or 3)-bromopropoxycarbonyl, 2,2-dichloroethoxycarbonyl or 2,2,2-trichroloethoxycarbonyl); hydroxy(lower)alkoxycarbonyl such as 2-hydroxyethoxycarbonyl or 2(or 3)-hydroxypropoxycarbonyl; lower alkoxy(lower)alkoxycarbonyl such as 2-methoxyethoxycarbonyl, 2-ethoxyethoxycarbonyl or 2(or 3)-methoxy(or ethoxy)-propoxycarbonyl; aryloxycarbonyl such as phenoxycarbonyl, tolyloxycarbonyl, xylyloxycarbonyl or p-chlorophenoxycarbonyl; ar(lower)alkoxycarbonyl such as benzyloxycarbonyl, p-bromobenzyloxycarbonyl, o-methoxybenzyloxycarbonyl or phenethyloxycarbonyl; ar(lower)alkoxy(lower)alkoxycarbonyl such as 2-(benzyloxyl)ethoxycarbonyl or 2(or 3)-(benzyloxy)-propoxycarbonyl; aryloxy(lower)alkoxycarbonyl such as 2-(phenoxy)ethoxycarbonyl or 2(or 3)-(phenoxy)-propoxycarbonyl; N- or N,N-(di)-substituted amino(-lower)alkoxycarbonyl such as N- or N,N-(di)-(lower)-alkylamino(lower) alkoxycarbonyl (e.g. 1(or 2)-[N-methyl(or N,N-dimethyl)amino]ethoxycarbonyl, 1(or 2)-[N-ethyl(or N,N-diethyl)amino]ethoxycarbonyl, or 1(or 2)-(N-methyl-N-ethylamino)ethoxycarbonyl or lower alkyl-N-ar(lower)alkylamino(lower)-alkoxycarbonyl(e.g.2-(N-methyl-N-benzylamino)ethoxycarbonyl) and the like, and further $R_2$ and $R_3$ may be same or different;

Lower alkyl substituted with oxo includes lower alkanoyl such as formyl, acetyl, propionyl, butyryl, isobutyryl, valeryl, isovaleryl or pivaloyl and lower alkanoyl(lower)alkyl such as formylmethyl, acetonyl, 2-formylethyl, 3-formylpropyl or butyrylmethyl. The carbonyl group thereof may be protected with suitable protecting group, and thus protected carbonyl group in this invention means a group given by protecting the carbonyl with conventionally employed protecting group for a carbonyl. Suitable examples of such protected carbonyl group are acetal, cyclic-acetal, thioacetal, cyclic-thioacetal, cyclicmonothioacetal or acylal types of group. Examples of these lower alkyl containing such protected carbonyl group are gem-di-(lower)alkoxy(lower)alkyl (e.g. dimethoxymethyl, 1,1-dimethoxyethyl, diethoxymethyl, dipropoxymethyl, 2,2-diethoxyethyl or 2,2-diethoxypropyl); gem-lower alkylenedioxy(lower)alkyl (e.g. 1,3-dioxolan-2-yl, 2-methyl-1,3-dioxolan-2-yl, 4-methyl-1,3-dioxolan-2-yl, 4,5-dimethyl-1,3-dioxolan-2-yl, 1,3-dioxan-2-yl, 2-methyl-1,3-dioxan-2-yl, 1,3-dioxolan-2-ylmethyl, 2-methyl-1,3-dioxolan-2-ylmethyl or 3-(1,3-dioxolan-2-yl)propyl); gem-di-(lower)alkylthio(lower)-alkyl (e.g. dimethylthiomethyl, 1,1-dimethylthioethyl, diethylthiomethyl or 2,2-diethylthioethyl); gem-lower alkylenedithio(lower-)alkyl (e.g. 1,3-dithiolan-2-yl, 2-methyl-1,3-dithiolan-2-yl, 4-methyl-1,3-dithiolan-2-yl, 4,5-dimethyl-1,3-dithiolan-2-yl, 1,3-dithian-2-yl, 2-methyl-1,3-dithian-2-yl, 1,3-dithiolan-2-ylmethyl, 2-methyl-1,3-dithiolan-2-ylmethyl or 3-(1,3-dithiolan-2-yl)propyl); and gem-di(-lower)alkanoyloxy(lower)alkyl (e.g. diacetoxymethyl, 1,1-diacetoxyethyl, dipropionyloxymethyl or 2,2-dipropionyloxyethyl); 5 or 6-membered saturated 1-oxa-3-thioheterocyclic-1-yl-(lower)alkyl (e.g. 1,3-oxathiolan-2-yl, 2-methyl-1,3-oxathiolan-2-yl, 4-methyl-1,3-oxathiolan-2-yl, 4,5-dimethyl-1,3-oxathiolan-2-yl, 1,3-oxothian-2-yl, 2-methyl-1,3-oxothian-2-yl, 1,3-oxathiolan-2-ylmethyl, 2-methyl-1,3-oxathiolan-2-ylmethyl or 3-(1,3-oxathiolan-2-yl)propyl).

A 5 or 6-membered saturated N-contianing heterocyclic-1-yl group may be one which may contain additional one or more hetero atom(s) selected from nitrogen, sulfur and oxygen atoms such as pyrrolidin-1-yl, piperidino, imidazolidin-1-yl, morpholino or thiomorpholino, and it may be optionally substituted with hydroxy, lower alkyl or hydroxy(lower)alkyl such as hydroxymethyl, 2-hydroxyethyl, 2-hydroxypropyl or 3-hydroxypropyl.

The other terms of each lower alkoxyimino, N'- or N',N'-di-(lower)alkylamino(lower)alkylimino, hydroxy(lower)alkylamino, N'- or N',N'-di-(lower)alkylamino(lower)alkylamino and hydroxy(lower)alkylamino will be clearly defined by applying optionally the above given exemplifications of the terms to them.

According to the present invention, 1,4-dihydropyridine derivatives (I) can be produced by various processes, which fall into the following classification:
(I Construction of fundamental structure)
  1. Ring formation of 1,4-dihydropyridine nucleus.
(II Transformations of functions)
  2. Hydrolysis for removal of protecting group of protected carbonyl group
  3. Condensation to form imino-function.
  4. Dehydration
  5. Reduction of oxo- or imino-function.
  6. Acylation of hydroxy-function.
  7. Oxidation of alcohol to carbonyl compound.
  8. Pyrolytic ring closure.
  9. Other transformations.

Each of these processes will be hereinafter illustrated.
1. Ring Formation of 1,4-dihydropyridine nucleus.
Some of the compound (I) representable by the following formula:

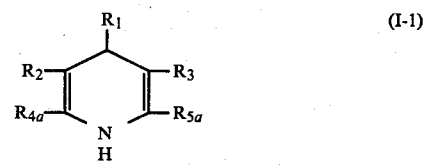
(I-1)

wherein $R_1$, $R_2$ and $R_3$ are each as defined above and $R_{4a}$ and $R_{5a}$ are each hydrogen, lower alkyl or lower alkyl substituted with oxo wherein thus formed carbonyl group is protected with suitable protecting group, provided that at least one of $R_{4a}$ and $R_{5a}$ is lower alkyl substituted with oxo wherein thus formed carbonyl group is protected with suitable protecting group, can be prepared by carrying out one of the reactions of the processes, which comprises
(1) reacting a compound of the formula:

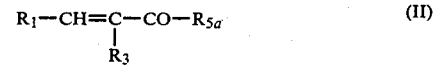
(II)

wherein $R_1$, $R_3$ and $R_{5a}$ are each as defined above, with an amino compound of the formula:

$$R_{4a}-C=CH-R_2 \quad \text{(III)}$$
$$\phantom{R_{4a}-C=C}|$$
$$\phantom{R_{4a}-C=C}NH_2$$

wherein $R_2$ and $R_{4a}$ are each as defined above, (2) subjecting a mixture of an aldehyde compound of the formula:

$$R_1-CHO \quad \text{(II')}$$

wherein $R_1$ is as defined above, an ester of β-ketonic acid of the formula:

$$R_{5a}-COCH_2-R_3 \quad \text{(II'')}$$

wherein $R_3$ and $R_{5a}$ are each as defined above, and an amino compound (III) to reaction, or (3) reacting an acetylene compound of the formula:

$$R_2-C\equiv C-R_{4a} \quad \text{(III')}$$

wherein $R_2$ and $R_{4a}$ are each as defined above, with ammonia or an ammonium salt and a compound (II).

The starting compound (II) used in the reactions (1) and (3) may be novel and prepared by reacting the aldehyde (II') with the β-ketoacid ester (II'') in a conventional manner, and the ammonium salt used in the reaction (3) includes an inorganic ammonium salt such as ammonium chloride or ammonium sulfate, or an organic ammonium salt such as ammonium acetate.

In the above reactions (1), (2) and (3), there can be employed the starting compounds (II), (II''), (III) and (III') wherein the symbols $R_{4a}$ and $R_{5a}$ are occasionally exchanged into each other, even when both symbols are not the same groups, and, in such case, the substantially same object compound (I-1) may be obtained not only when $R_{4a}$ and $R_{5a}$ are the same groups, irrespective of $R_2$ and $R_3$ being the same groups or not, but also when $R_{4a}$ and $R_{5a}$ are not the same groups and $R_2$ and $R_3$ are the same groups.

Regarding the reactions (1) and (2), the starting compound (II) may include geometric isomers such as cis-trans isomers due to the double bond in its molecule. Such cis-trans isomers may be equilibrated and, therefore, each or a mixture of the isomers of (II) may be applied as the starting materials to provide the same object compound (I-1).

The reactions (1), (2) and (3) can be carried out at ambient temperature or under warming or heating with or without a suitable solvent such as benzene, toluene, xylene, chloroform, carbon tetrachloride, methylene chloride, ethylene chloride, methanol, propanol, butanol, water or other conventional solvents. The reactions can be usually promoted in the presence of an agent such as an acid (e.g. acetic acid), a base (e.g. pyridine or picoline) or in a conventional buffer solution. These agents may act as a reaction promotor and also used as a solvent when they are in liquid. The reactions can be also accelerated by heating. The reaction condition may vary according to the kind of the reactants to be used.

2. Hydrolysis for removal of protecting group of protected carbonyl group. The compound of the formula:

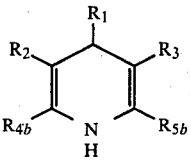

wherein $R_1$, $R_2$ and $R_3$ are each as defined above and $R_{4b}$ and $R_{5b}$ are each hydrogen, lower alkyl or lower alkyl substituted with oxo, provided that at least one of $R_{4b}$ and $R_{5b}$ is lower alkyl substituted with oxo, can be prepared by hydrolyzing the compound (I-1) which can be obtained in the above-mentioned ring formation process. In this process, the protecting group(s) of the carbonyl group on the alkyl group for $R_{4a}$ and/or $R_{5a}$ of the compound (I-1) is removed by hydrolysis.

Hydrolysis may be carried out in a conventional manner and, for example, the removal of the protecting groups of acetal-type and cyclic acetal-type is preferably carried out by an acidic hydrolysis, i.e. in the presence of an acid such as an inorganic acid (e.g. hydrochloric acid or sulfuric acid) or an organic acid (e.g. formic acid, acetic acid, trifluoroacetic acid or p-toluenesulfonic acid); the removal of the protecting groups of thioacetal-type, cyclic thioacetal-type and cyclic monothioacetal type is preferably carried out by hydrolysis in the presence of a heavy metal salt such as mercuric chloride or copper chloride; and the removal of the protecting group of acylal-type is preferably carried out by the above mentioned acidic hydrolysis or a basic hydrolysis, i.e. in the presence of a base such as an inorganic base (e.g. sodium hydroxide, potassium hydroxide, sodium carbonate or potassium carbonate) or an organic base (e.g. sodium methoxide, sodium ethoxide, potassium methoxide, potassium ethoxide, pyridine or picoline). These reactions of hydrolysis may be carried out in a suitable conventional solvent such as water, acetone, methyl ethyl ketone, dioxane, ethanol, methanol, N,N-dimethylformamide, N-methylmorpholine or dimethylsulfoxide, an optional mixture with water or a buffer solution thereof. The reaction temperature is not restrictive, and the reaction is usually conducted under cooling, at room temperature or under somewhat elevated temperature.

3. Condensation to form imino function The compound of the formula:

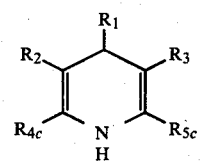

wherein $R_1$, $R_2$ and $R_3$ are each as defined above and $R_{4c}$ and $R_{5c}$ are each hydrogen, lower alkyl or substituted lower alkyl in which the subsituent is hydroxyimino, hydrazono, lower alkoxyimino, hydroxy(lower)alkylimino or N'- or N,N-di-(lower)alkylamino(lower)alkylimino, provided that at least one of $R_{4c}$ and $R_{5c}$ is said substituted lower alkyl, may be prepared by reacting a compound of the formula:

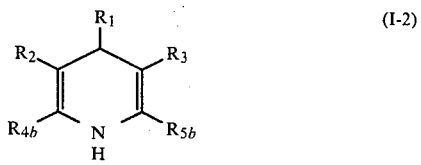
(I-2)

wherein $R_1$, $R_2$, $R_3$, $R_{4b}$ and $R_{5b}$ are each as defined above, with an amine of the formula:

$$R_8-NH_2 \qquad (IV)$$

wherein $R_8$ is hydroxy, amino, lower alkoxy, hydroxy(-lower)alkyl or N— or N,N-di(lower)alkylamino(lower-)alkyl.

According to this process the oxo group in $R_{4b}$ and/or $R_{5b}$ of the starting compound (I-2) is replaced by the imino group of N-$R_8$ (wherein $R_8$ is as defined above).

The starting compound (I-2) can be obtained by the above-mentioned hydrolysis process.

The reaction is carried out in a usual manner, for example, in the presence of a catalyst, such as an acid (e.g. hydrochloric acid, hydrobromic acid, sulfuric acid, formic acid, acetic acid, p-toluenesulfornic acid, boron trifluoride, silicon tetrachloride or titanium tetrachloride); in a basic condition realized by using the free amino-compound (IV); or an acidic or basic conventional buffer solution, and usually in a suitable conventional solvent such as water, dioxane, ethanol, methanol or dimethylformamide or an optional mixture with water thereof.

The reaction temperature is not restrictive, and the reaction is usually carried out under cooling, at room temperature or under somewhat elevated temperature. The amine (IV), which is used as a reactant, includes an N'- or N',N'-di-(lower)-alkylamino(lower)alkylamine such as N'-methyl or N',N'-dimethylamino-ethylenediamine, N'-ethyl or N',N'-diethylethylenediamine, N'-methyl or N',N'-dimethylaminotrimethylenediamine or N'-ethyl or N',N'-diethylaminotrimethylenediamine; hydroxy(lower)alkylamine such as ethanolamine or propanolamine; hydroxylamine; hydrazine and lower alkoxyamine such as O-methyl-, O-ethyl-, O-propyl-, or O-isopropyl-hydroxyamine. And these amines may be used in the form of salt with an acid such as an inorganic acid (e.g. hydrochloric acid or sulfuric acid) or an organic acid (e.g. acetic acid).

4. Dehydration

The compound of the formula:

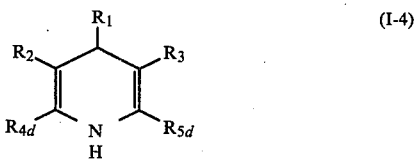
(I-4)

wherein $R_1$, $R_2$ and $R_3$ are each as defined above and $R_{4d}$ and $R_{5d}$ are each hydrogen, lower alkyl, cyano or ω-cyano(lower)alkyl, provided that, when one of $R_{4d}$ and $R_{5d}$ is hydrogen or lower alkyl, the other is always cyano or ω-cyano(lower)alkyl, and when $R_{4d}$ and $R_{5d}$ are not hydrogen or lower alkyl, both of them are a group selected from cyano or ω-cyano(lower)alkyl, or $R_{4d}$ is hydrogen or lower alkyl and $R_3$ and $R_{5d}$ are combined together to form a group of the formula:

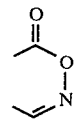

may be prepared by treating the compound of the formula:

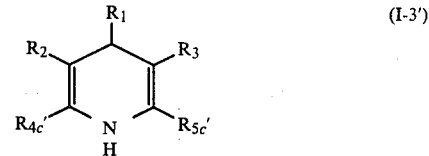
(I-3')

wherein $R_1$, $R_2$ and $R_3$ are each as defined above and $R'_{4c}$ and $R'_{5c}$ are each hydrogen, lower alkyl or ω-hydroxyimino(lower)alkyl, provided that at least one of $R'_{4c}$ and $R'_{5c}$ is ω-hydroxyinimo(lower)alkyl, with a dehydrating agent.

The starting compound (I-3') can be obtained by the above-mentioned condensation process.

Suitable example of the dehydrating agent may be organic or inorganic conventional ones such as an acid (e.g. sulfuric acid, phosphoric acid, polyphosphoric acid, formic acid, acetic acid, ethane sulfonic acid or p-tolene sulfonic acid), an acid anhydride (e.g. acetic anhydride, benzoic anhydride or phthalic anhydride), and acid halide (e.g. acetyl chloride, benzoyl chloride, trichloroacetylchloride, mesyl chloride, tosylchloride, ethyl chloroformate or phenylchloroformate), an inorganic halogen compound (e.g. thionylchloride, phosphorus pentachloride, phosphorus oxychloride, phosphorus tribromide, stannic chloride or titanium tetrachloride), a carbodiimide (e.g. N,N'-dicyclohexylcarbodiimide or N-cyclohexyl-N'-morpholinoethylcarbodiimide), N,N'-carbonyldiimidazole, pentamethyleneketene-N-cyclohexylmine, ethoxyacetylene, 2-ethyl-7-hydroxyisoxazolium salt, another phosphorus compound (e.g. phosphorus pentoxide, polyphosphoric acid ethylester, triethylphosphate or phenylphsphate) or the like. When an acid is used as the dehydrating agent, the reaction may be conveniently conducted in the presence of its alkali metal salt (e.g. sodium salt or potassium salt), or the like.

This reaction is usually carried out in a conventional solvent such as diethyl ether, dimethylformamide, pyridine, acetic acid, formic acid, benzene, carbon tetrachloride, chloroform, methylene chloride, tetrahydrofuran, dioxane, and the like, and usually carried out at room temperature or under heating, and the reaction temperature is not restrictive to the above.

According to this process, the terminal —CH═N-OH function in $R'_{4c}$ and/or $R'_{5c}$ of the starting compound (I-3') is transformed into cyano function in the resultant compound (I-4), and further there tends to produce the compound of the formula:

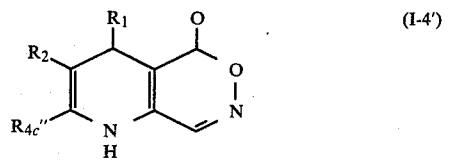
(I-4')

wherein R₁ and R₂ are each as defined above and R″₄c is hydrogen or lower alkyl when the starting compound (I-3′) wherein R′₅c is hydroxyiminomethyl is treated, for example, in rather highly acidic condition. The compound (I-4′) and the process for preparation thereof are also included in the scope of this invention.

This dehydration process can be also carried out successively to the foregoing condensation process without any isolation of the compound (I-3′). This case is also included in the scope of this invention.

5. Reduction of oxo- or imino- function

The compound of the formula:

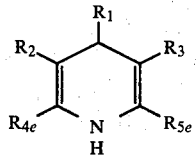

(I-5)

wherein R₁, R₂ and R₃ are each as defined above and R₄e and R₅e are each hydrogen, lower alkyl or substituted lower alkyl in which the substituent is hydroxy, Hydrazino, hydroxy(lower)-alkylamino or N′- or N′,N′-di(lower)alkylamino(lower)alkylamino, provided that at least one of R₄e and R₅e is said substituted lower alkyl or R₄e is hydrogen or lower alkyl and R₃ and R₅e are combined together to form

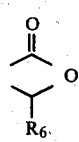

or

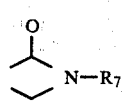

(wherein R₆ and R₇ are each as defined above), can be prepared by reducing the compound of the formula:

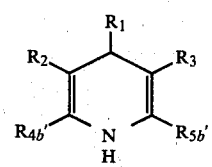

(I-2′)

wherein R₁, R₂ and R₃ are each as defined above and R′₄b and R′₅b are each hydrogen, lower alkyl or substituted lower alkyl in which the substituent is oxo, hydrazono, hydroxy(lower)alkylimino or N′- or N′,N′-di(-lower)alkylamino(lower)alkylimino, provided that at least one of R′₄b and R′₅b is said substitued lower alkyl.

The starting compound (I-2′) can be prepared by either of the above-mentioned process hydrolysis or condensation.

The reduction can be carried out by a conventional manner for reduction of oxo or imino to hydroxy or amino, respectively, for example, reduction with a reducing agent such as an alkali metal hydride (e.g. lithium borohydride, sodium borohydride, potassium borohydride or sodium cyanoborohydride) or catalytic reduction for which catalyst may be palladium carbon, palladium chloride or rhodium carbon and the like in a suitable conventional solvent. Examples of such solvents are water, methanol, ethanol, isopropanol, dimethylformamide, and the like. The reaction temperature is not restrictive, and the reaction is usually carried out under cooling, at room temperature or at somewhat elevated temperature. And, the method of reduction may be optionally selected according to the kind of the starting compound (I-2′).

According to this process, each oxo- or imino- function in the starting compound (I-2′) is transformed into the hydroxy- or amino-function, respectively, in the resultant compound (I-5), and further, the compound of the formula:

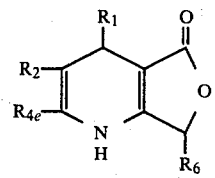

(I-5-1)

wherein R₆ is as defined above and R₄e is hydrogen or lower alkyl, and the compound of the formula:

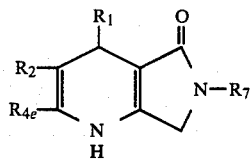

(I-5-2)

wherein R₇ is as defined above and R₄e is hydrogen or lower alkyl, can be produced simultaneously via the compound (I-5) wherein R₅e is hydroxymethyl (when R₆ is hydrogen), 1-hydroxyethyl (when R₆ is methyl), 2-(N′,N′-diethylamino)ethylaminomethyl (when R₇ is 2-(N, N-diethylamino)ethyl) or 2-hydroxyethylaminomethyl (when R₇ is 2-hydroxyethyl), respectively.

These cases are also included in the scope of this invention.

6. Acylation of hydroxy function

The compound of the formula:

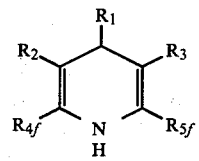

(I-6)

wherein R₁, R₂ and R₃ are each as defined above and R₄f and R₅f are each hydrogen, lower alkyl or acyloxy(-lower)alkyl, provided that at least one of R₄f and R₅f is acyloxy(lower)alkyl, can be prepared by reacting the compound of the formula:

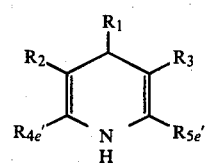

(I-5′)

wherein $R_1$, $R_2$ and $R_3$ are each as defined above and $R'_{4e}$ and $R'_{5e}$ are each hydrogen, lower alkyl or hydroxy(lower)alkyl, provided that at least one of $R'_{4e}$ and $R'_{5e}$ is hydroxy(lower)alkyl, with an acylating agent of the formula:

$$R_9-OH \quad (V)$$

wherein $R_9$ is acyl, or its reactive derivative.

The starting compound (I-5′) can be prepared in the above-mentioned reduction process.

Suitable examples of acyl for $R_9$ are lower alkanoyl which may be substituted with carboxy, esterified carboxy, N- or N,N-di-substituted amino or arylxoy, aroyl and the like.

Suitable acylating agent (V) includes lower alkanoic acid such as formic acid, acetic acid, propionic acid, butyric acid, isobutyric acid, valeric acid, isovaleric acid or pivalic acid; carboxy(lower)alkanoic acid, i.e. di- or poly-basic carboxylic acid such as malonic acid, succinic acid, adipic acid, glutaric acid, pimeric acid or suberic acid; esterified carboxy(lower)alkanoic acid, i.e. a half ester of the preceding di- or poly-basic carboxylic acid such as a respective half lower alkyl ester (e.g. methyl ester, ethyl ester or propyl ester); N- or N,N-di-substituted amino(lower)alkanoic acid such as N- or N,N-di-(lower)alkylamino(lower)alkanoic acid (e.g. N-methyl(or N, N-dimethyl)amino-acetic acid, 1(or 2)-[N-ethyl(or N,N-diethyl(amino]propionic acid or 1(or 2)-[N-methyl-N-ethylamino]propionic acid) or N-lower alkyl-N-ar(lower)alkylamino(lower)alkanoic acid (e.g. 1-(or 2)[N-methyl-N-benzylamino] propionic acid); aryloxy(lower)alkanoic acid such as phenoxyacetic acid, tolyloxyacetic acid, 2(or 3 or 4)-chlorophenoxyacetic acid, 2-[2(or 3 or 4)-chlorophenoxy]propionic acid, 2(or 3 or 4)nitrophenoxyacetic acid or 2(or 3 or 4)-methoxy-phenoxyacetic acid); and aromatic carboxylic acid such as benzoic acid, naphthoic acid, toluic acid; and the like.

The reactive derivative at the carboxy group of the compound (V) may be its acid halide such as acid chloride; acid anhydride; active amide; azide; or reactive ester such as methyl ester, ethyl ester, cyanomethyl ester, p-nitrophenyl ester of pyranyl ester.

The reaction can be preferably carried out in the presence of a base such as an inoranic base (e.g. sodium hydroxide, potassium hydroxide, sodium bicarbonate, potassium bicarbonate, sodium carbonate or potassium carbonate) or an organic base (e.g. N-methylpiperidine, triethylamine, pyridine, N-methylmorphorine or N,N-dimethylaniline), and a suitable conventional solvent such as pyridine, ether, dioxane, acetone, chloroform, methylene chloride, tetrahydrofuran, dimethylformamide, benzene or water. The reaction temperature is not restrictive, and the reaction is usually carried out under cooling, at room temperature or under somewhat elevated temperature. If necessary, there may be used a conventional condensing agent such as phosphorus oxychloride, thionylchloride, N,N′-dicyclohexylcarbodiimide, N-cyclohexyl-N′-morphorinoethylcarbodiimide, pentamethyleneketene-N-cyclohexylimine, alkoxyacetylene, 2-ethyl 7-hydroxyisoxazolium salt, 2-ethyl-5-(m-sulfophenyl)isoxazolium hydroxide or 6-chloro-1-tosyloxybenzotriazole.

7. Oxidation of alcohol to aldehyde

The compound of the formula:

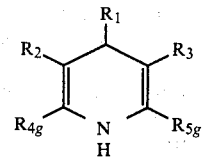

(I-7)

wherein $R_1$, $R_2$ and $R_3$ are each as defined above and $R_{4g}$ and $R_{5g}$ are each hydrogen, lower alkyl, formyl or ω-formyl(lower)alkyl, provided that, when one of $R_{4g}$ and $R_{5g}$ is hydrogen or lower alkyl, the other is always formyl or ω-formyl(lower)alkyl, and $R_{4g}$ and $R_{5g}$ are not hydrogen or lower alkyl, both of them are a group selected from formyl and ω-formyl(lower)alkyl, may be also prepared by oxidizing the compound of the formula

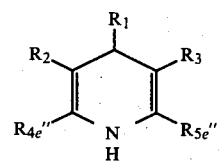

(I-5″)

wherein $R_1$, $R_2$ and $R_3$ are each as defined above and $R''_{4e}$ and $R''_{5e}$ are each hydrogen, lower alkyl, or ω-hydroxy(lower)alkyl, provided that at least one of $R''_{4e}$ and $R''_{5e}$ is ω-hydroxy(lower)alkyl.

The starting compound (I-5″) can be prepared in the above-mentioned reduction process.

The oxidation can be carried out by any conventional method which selectively oxidize a primary alcohol function to the corresponding formyl function without any adverse influence on the other parts of the compound (I-5″).

A suitable oxidation is carried out by reacting the starting compound (I-5″) with an organic sulfonic acid or its reactive derivative, preferably under warming and in the presence of a base, with or without a solvent. This reaction may be proceeded via the organic sulfonic acid ester of the compound (I-5″) as an intermediate which may be produced in the course of the reaction.

Suitable organic sulfonic acid may be methanesulfonic acid, p-toluenesulfonic acid, p-nitrophenylsulfonic acid and the like, and its reactive derivative and the base can be referred to those of the compound (V) as mentioned in the preceding acylation process.

8. Pyrolytic ring closure

The compound of the formula:

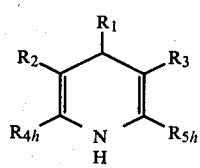

(I-8)

wherein $R_1$ and $R_2$ are each as defined above, $R_{4h}$ is hydrogen or lower alkyl, and $R_3$ and $R_{5h}$ are combined together to form a group of the formula:

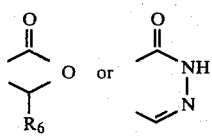

in which $R_6$ is as defined above, may be prepared by heating in neat or in a conventional solvent the compound (I-5) wherein $R_{4e}$ is hydrogen or lower alkyl and $R_{5e}$ is hydroxymethyl, or the compound (I-3) wherein $R_{4c}$ is hydrogen or lower alkyl and $R_{5c}$ is hydrazonomethyl, respectively.

A suitable conventional solvent includes water, methanol, ethanol, isopropanol, butanol, dioxane, benzene, toluene, dimethylformamide, tetrahydrofuran, or a conventional buffer solution and the like. The reation can be accelerated by the addition of a catalytic or more amount of an organic or inorganic base such as trialkylamine (e.g. trimethylamine or triethylamine), pyridine, alkali metal compound (e.g. sodium hydroxide, potassium hydroxide, sodium bicarbonate or potassium bicarbonate) and the like, or an organic or inorganic acid such as acetic acid, p-toluensulfonic acid, hydrochloric acid, sulfuric acid, boron trifluoride, silicon tetrachloride, titanium tetrachloride and the like. The reaction temperature is not so much restrictive, and the reaction is preferably carried out under warming or heating.

9. Other transformations (1) The compound (I) wherein $R_1$, $R_2$ and $R_3$ are as defined above and $R_4$ and $R_5$ are each hydrogen, lower alkyl or lower alkyl substituted with a 5 or 6-membered saturated N-containing heterocyclic-1-yl which may have hydroxy, lower alkyl or hydroxy(lower)alkyl, provided that at least one of $R_4$ and $R_5$ is said substituted lower alkyl, can be prepared by subjecting the compound (I-5') to halogenation of the hydroxy function, whereby a halo-compound is provided, followed by substitution reaction with a 5 or 6-membered saturated imino-containing heterocyclic compound.

The first halogenation reaction can be carried out by reacting halogenating agent such as conventional one (e.g. thionyl chloride, phosphorus tribromide, phosphorus pentachloride or phosgene) and other one which comprises a combination of phosphorus compound such as triphenyl phosphine or tri(lower)-alkyl phosphite (e.g. trimethyl phosphite or triethyl phosphite) and a polyhalo(lower)alkane such as carbon tetrachloride or carbon tetrabromide in a suitable solvent. Examples of the solvents may be carbon tetrachloride, chloroform, methylene chloride, benzene and the like. This reaction is preferably carried out in around neutral conditions, therefore, the latter combination agent is the most preferable one. On the contrary, in case of the former conventional agent, it may be usually carried out on maintaining neutrality of the reaction medium, for example, by neutralizing with a base or scavenging the resulting acidic substances from the halogenating agent in the course of reaction performed. The reaction temperature is usually varied in accordance with the kind of halogenating agent, and therefore, the reaction is preferably carried out at somewhat elevated temperature (e.g. under warming or heating) in case of the latter combination agent, and at much more milder temperature (e.g. under cooling or warming) in case of the former conventional agent, and preferably under anhydrous conditions.

The second substitution reaction is carried out in a substantially similar manner to that of aforementioned acylation process in the presence or absence of a base. The reaction can be carried out in a suitable solvent such as chloroform, methylene chloride, benzene, acetone, ether, tetrahydrofuran, dimethylformamide, methanol, ethanol or propanol. The reaction temperature is not restrictive, and the reaction is usually carried out at room temperature or at an elevated temperature (e.g. under warming or heating). According to this method, the hydroxy(lower)alkyl group for $R'_{4e}$ and/or $R'_{5e}$ of the compound (I-5') is transformed at first into the halo(lower)alkyl group and then into the lower alkyl substituted with 5 or 6-membered saturated N-containing heterocyclic group for $R_4$ and/or $R_5$ of the compound (I).

(2) The compound (I) wherein at least one of $R_2$ and $R_3$ is N- or N,N-di-substituted amino(lower)alkoxycarbonyl can be prepared by reacting the corresponding compound (I) wherein at least one of $R_2$ and $R_3$ is halo(lower)alkoxycarbonyl with a N- or N,N-di-substituted amine in accordance with the substantially same manner as that of the above-mentioned substitution reaction in (1).

(3) The compound (I) wherein at least one of $R_2$ and $R_3$ is hydroxy(lower)alkoxycarbonyl can be prepared by subjecting the corresponding compound (I) wherein at least one of $R_2$ and $R_3$ is halo(lower)alkoxycarbonyl to hydrolysis substantially in the same method as that of the afore-mentioned hydrolysis process.

(4) The compound (I) wherein $R_1$, $R_2$ and $R_3$ are each as defined above and $R_4$ and $R_5$ are each hydrogen, lower alkyl or substituted lower alkyl selected from gem-di-(lower)alkoxy(lower)alkyl; gem-lower alkylenedioxy(lower)alkyl; gem-di-(lower)alkylthio(lower)alkyl and gem-(lower)alkylene-dithio(lower)alkyl, provided that at least one of $R_4$ and $R_5$ is said substituted lower alkyl can be also prepared by reacting the corresponding compound (I-2) with a hydroxy compound such as lower alkanol (e.g. methanol, ethanol or propanol) or lower alkane diol (e.g. ethylene glycol, propylene glycol, 2,3-butane diol or 1,3-propane diol); a thiol compound such as lower alkanethiol (e.g. methanethiol or ethanethiol) or lower alkane dithiol (e.g. ethanedithiol, 1,2-propanedithiol, 2,3-butanedithiol or 1,3-propanedithiol).

This reaction preferably carried out in the presence of catalytic amount of an organic or inorganic acid such as hydrochloric acid, sulfuric acid, acetic acid, boron trifluoride, zinc chloride or p-toluenesulfonic acid.

(5) The compound (I) wherein $R_1$, $R_2$ and $R_3$ are each as defined above and $R_4$ and $R_5$ are each hydrogen, lower alkyl or cyano(lower)alkyl, provided that at least one of $R_4$ and $R_5$ is cyano(lower)alkyl can be prepared by reacting the halo-compound obtained in the above transformation (1) with a compound of the formula: $R_{10}$—CN wherein $R_{10}$ is hydrogen or a metal.

Suitable metals for $R_{10}$ are alkali metal such as sodium or potassium, alkaline earth metal such as magnesium or calcium, heavy metal such as mercury or silver and the like.

The reaction is usually carried out at room temperature or under heating in a suitable solvent such as water, methanol, ethanol, butanol chloroform, benzene, toluene, N,N-dimethylformamide, dimethylsulfoxide, N- methylmorpholine, pyridine or other conventional solvent.

(6) In addition to the above, the compound of the formula:

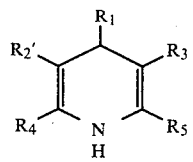

wherein $R_1$, $R_3$, $R_4$ and $R_5$ are each as defined above, and $R_{2'}$ is hydroxy(lower)alkoxycarbonyl, may also be prepared by subjecting a compound of the formula:

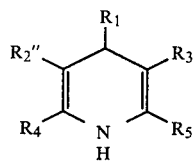

wherein $R_1$, $R_3$, $R_4$ and $R_5$ are each as defined above, and $R_{2''}$ is acyloxy(lower)alkoxycarbonyl, to hydrolysis in substantially the same method as that of hydrolysis process.

A suitable acyloxy moiety in acyloxy(lower)alkoxycarbonyl includes lower alkanoyloxy such as formyloxy, acetoxy, propionyloxy and the like.

In accordance with the present invention, the product which is given during the reaction is separated and isolated from the reaction mixture by methods commonly used for this purpose, and may be subjected to routinely used purification procedures, for instance, to recrystallization from an appropriate solvent or a mixture of such solvents.

The compound (I) thus obtained wherein at least $R_2$ and $R_3$ or $R_4$ and $R_5$ are not just same each other, includes stereoisomers due to the presence of at least one asymmetric carbon atom at the fourth position of the 1,4-dihydropyridine nucleus and can exist as each optical isomer or a racemic mixture. And further some of the compound (I) which has not less than two asymmetric carbon atoms in its molecule may exist as each diastereomer(s) or the mixture thereof. The mixture of the diastereomers can be resolved into each racemic compound by conventional resolution methods such as chromatography or fractional recrystallization and the like and the racemic compound can be resolved into each optical isomer by a conventional method for racemic resolution such as a resolution by fractional recrystallization of a salt of the racemic compound with an optically active acid, e.g., tartaric acid or camphor sulfonic acid.

The compound (I) is possessed of vasodilating activity and useful for therapeutic treatment in hypertension and cardiovascular diseases such as coronary insufficiency, angina pectoris or myocardial infarction.

The compositions of this invention comprise, as an active ingredient, the 1,4-dihydropyridine derivatives (I) in an amount of about 0.1 mg. to about 500 mg., preferably about 1 mg. to about 50 mg. per daily oral dosage unit, with IV dosage being 10 to 25% of oral.

One skilled in the art will recognize that in determining the amounts of the active ingredient in the claimed dosage unit form, the activity of the ingredient as well as the size of the host animal must be considered. That is, on mg./kg. oral basis (see above ratio for IV), the amount of the active ingredient in the compositions will be about 1 μg./kg. to about 10 mg./kg. and more, preferably about 0.5 mg./kg. For administration purpose of this pharmaceutical composition, the active ingredients may be usually formed as tablet, granule, powder, capsule, suppository, suspensions, solutions and the like. A pharmaceutical carrier or diluent includes solid or liquid non-toxic pharmaceutically acceptable substances. Exemplar of solid or liquid carriers or diluents are lactose, magnesium stearate, terra alba sucrose, corn starch, talc, stearic acid, gelatin, agar, pectin, acacia peanut oil, olive oil or sesame oil, cacao butter or the like. Similarly, the carrier or diluent may include a time delay material such as glyceryl monostearate or glyceryl distearate alone or with a wax.

A wide variety of pharmaceutical forms can be employed. Thus, if a solid carrier is used, the preparation can be tabletted, placed in a hard gelatin capsule or in the form of a troche or lozenge.

The pharmacological activity of the 1,4-dihydropyridines of the formula (I) is demonstrated by standard procedures, that is, by administering intravenously the following test 1,4-dihydropyridines to dogs anesthetized with pentobarbital and recording the coronary blood flow. The test results are given below:

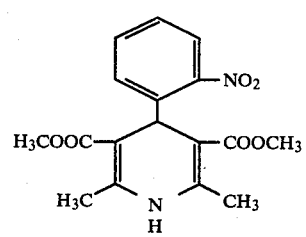

[A]

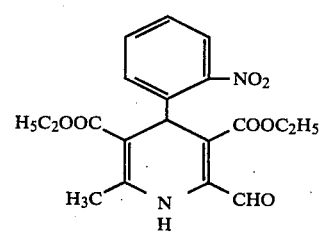

[B]

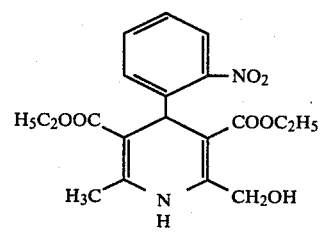

[C]

-continued

[D] 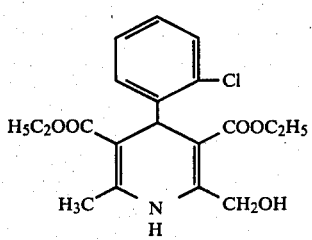

[E] 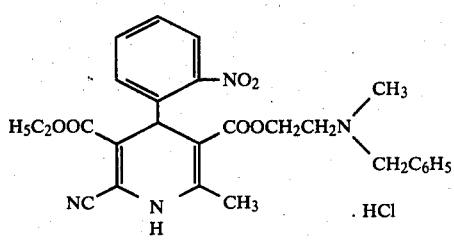

[F] 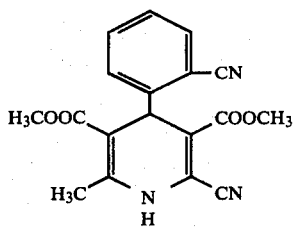

[G] 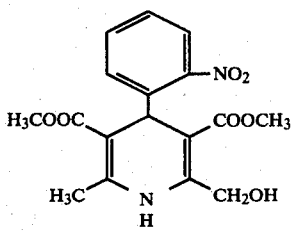

[H] 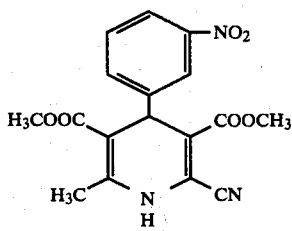

TABLE

Increase of coronary blood flow (%)
The values indicate percentages compared to
control [29.5 ± 5.5 ml/min.].

| Compound | Dose μg/kg | | |
|---|---|---|---|
| | 64 | 250 | 1000 |
| A | 169 | 118 | dead |
| B | 190 | 174 | 155 |
| C | 214 | 168 | 175 |
| D | 171 | 195 | 179 |
| E | 185 | 215 | 144 |
| F | 173 | 159 | 156 |
| G | 199 | 195 | 170 |
| H | 182 | 205 | 174 |

Compound A is known as the generic name "Nifedipine" and already marketed as a coronary vasodilator.

The following Examples are given merely for the purpose of illustrating the syntheses of some specific object compounds of the present invention, but not of limiting the same thereto.

EXAMPLE 1

(1) A solution of 2-chlorobenzaldehyde (1.0543 g), ethyl 4,4-diethoxyacetoacetate (1.6477 g) and piperidine (1 to 2 drop(s)) in benzene (30 ml) was refluxed under azeotropic dehydration for 4.5 hours. After cooling, the resultant solution was washed with water and dried. The solvent was removed from the solution to give orange oil (2.7196 g) of ethyl 2-(2-chlorobenzylidene)-4,4-diethoxyacetoacetate. The mixture of the compound obtained above and ethyl 3-amino-4,4-diethoxycrotonate (1.6580 g) was heated with stirring at about 100° C. for 1.5 hours and about 120° C. for 8 hours. After cooling, the reaction mixture was dissolved in ethyl acetate. The solution was washed with water and dried, and then the solvent was removed from the solution to give orange oil (4.21 g) of diethyl 2,6-bis(diethoxymethyl)-4-(2-chlorophenyl)-1,4-dihydropyridine-3,5-dicarboxylate. The product was purified by a column chromatography on silica gel with an eluent (benzene:ethyl acetate=10:1) to give pure product.

I.R. Spectrum (Film)
ν(cm$^{-1}$): 3430, 1695, 1610, 1487, 1472, 1368, 1273, 1200, 1093, 1059, 755

N.M.R. Spectrum (δ, CDCl$_3$)
ppm: 1.22 (18H, t, J=7 Hz), 3.3 to 3.9 (8H, m), 4.08 (4H, q, J=7 Hz), 5.55 (1H, s), 6.14 (2H, s), 6.9 to 7.5 (4H, m), 7.90 (1H, broad s)

(2)-(1) A solution of 2-chlorobenzaldehyde (14.0570 g), ethyl 4,4-diethoxyacetoacetate (21.8240 g) and piperidine (1 ml) in benzene (100 ml) was refluxed under azeotropic dehydration for 4 hours. The resultant solution was washed with water, dried and concentrated to give oily ethyl 2-(2-chlorobenzylidene)-4,4-diethoxyacetoacetate. The mixture of the compound obtained above and ethyl 3-aminocrotonate (12.92 g) was heated in an oil bath (about 100° C.) for 8 hours. The reaction mixture was dissolved in ethyl acetate, washed with water, dried and then the solvent was removed to give crude oil (52.4 g). The oil was purified by column chromatography on silica gel with an eluent (benzene:ethyl acetate=20:1) to give diethyl 2-methyl-4-(2-chlorophenyl)-6-diethoxymethyl-1,4-dihydropyridine-3,5-dicarboxylate, which was recrystallized from n-hexane to give the pure crystals (20.2445 g), m.p. 75° to 77° C.

(2)-(2) A solution of 2-chlorobenzaldehyde (1.4057 g), ethyl acetate (1.3014 g) and piperidine (5 drops) in benzene (10 ml) was refluxed under azeotropic dehydration for 5 hours. After cooling, to the resultant solution was added benzene, and the solution was washed with water twice and dried. The solvent was removed from the resultant solution to give yellowish oil of ethyl 2-(2-chlorobenzylidene)acetoacetate (2.7351 g). The mixture of the compound obtained above and ethyl 3-amino-4,4-diethoxycrotonate (2.17 g) was heated at about 120° C. with stirring for 4 hours. After cooling, the resultant oil was dissolved in diethyl ether, washed with water and saturated aqueous solution of sodium chloride in turn and then dried. The solution was concentrated under reduced pressure to give a reddish oil (4.5133 g). The product was purified by column chromatography on silica gel with an eluent (benzene:ethyl acetate=20:1) to give yellowish oil of diethyl 2-methyl-4-(2-chlorophenyl)-6-diethoxymethyl-1,4-dihydropyridine-3,5-dicarboxylate (2.25 g). The product was crystallized in n-hexane and the crystals were collected by filtration, which were identified with the authentic sample.

(3) A mixture of 2-chlorobenzaldehyde (2.81 g), methyl 4,4-dimethoxy-3-oxovalerate (3.81 g) and piperidine (0.2 ml) in benzene (20 ml) was refluxed under azeotropic dehydration for 7.5 hours. A small amount of benzene was added to the reaction mixture and the resultant solution was washed with water and dried over magnesium sulfate. The solvent was removed from the solution to give a reddish oil (7.04 g) of methyl 2-(2-chlorobenzylidene)-4,4-dimethoxy-3-oxovalerate. The mixture of the oily product (6.39 g) obtained above and methyl 3-aminocrotonate (2.33 g) was heated at 132° C. for 3.5 hours, allowed to stand and then dissolved in ethyl acetate. The resultant solution was washed with water and an aqueous sodium chloride solution, and dried over magnesium sulfate. The solvent was removed from the solution under reduced pressure to give a viscous and brown oil (8.28 g). This oil was subjected to column chromatography on silica gel with an eluent (a mixture of 20 parts of benzene and one part of ethyl acetate by volume) to give an oily substance (5.26 g).

This substance was dissolved in a mixture of ethyl acetate and diethyl ether and the solvent was removed under reduced pressure to give colorless powder (1.0625 g). This powder was recrystallized from a mixture of n-hexane and ethyl acetate to give faint yellow granules of dimethyl 2-methyl-4-(2-chlorophenyl)-6-(1,1-dimethoxyethyl)-1,4-dihydropyridine-3,5-dicarboxylate, m.p. 145° to 146° C.

(4)-(1) A solution of 2-nitrobenzaldehyde (9.0672 g), ethyl 4,4-diethoxyacetoacetate (13.0944 g) and piperidine (1ml) in benzene (45 ml) was refluxed under azeotropic dehydration for 3 hours. To the resultant solution was added water, and the solution was extracted with diethyl ether. The extract was washed three times with water, dried and then the solvent was removed under reduced pressure to give ethyl 2-(2-nitrobenzylidene)-4,4-diethoxyacetoacetate. The mixture of the compound obtained above and ethyl 3-aminocrotonate (7.7496 g) was heated in an oil bath (95° to 100° C.) for 8 hours. The resultant mixture was extracted with diethyl ether, and the extract was washed with water and dried. The solvent was removed from the extract. The residue was purified by column chromatography on silica gel with an eluent (benzene:ethyl acetate=20:1) to give oily diethyl 2-methyl-4-(2-nitrophenyl)-6-diethoxymethyl-1,4-dihydropyridine-3,5-dicarboxylate (19.3 g). The product was crystallized in n-hexane and the crystals were collected by filtration and then recrystallized from a mixture of n-hexane and diethyl ether to give the pure compound, m.p. 80° to 81.5° C.

N.M.R. Spectrum ($\delta$, CDCl$_3$)
ppm: 1.16 (3H, t, J=7 Hz), 1.18 (3H, t, J=7 Hz), 1.25 (6H, t, J=7 Hz), 2.37 (3H, s), 3.4 to 4.4 (8H, m), 5.92 (1H, s), 6.20 (1H, s) 6.67 (1H, broad s), 7.0 to 7.8 (4H, m)

(4)-(2) A solution of 2-nitrobenzaldehyde (3.0224 g), ethyl 4,4-diethoxyacetoacetate (4.3650 g) and piperidine (240 mg) in benzene (12 ml) was refluxed under azeotropic dehydration for 80 minutes. The reaction mixture was allowed to stand to cool, and ethyl acetate was added thereto. The mixture was washed with water twice and dried. The solvent was removed to give an orange-yellow oil (6.88 g). The oil was kept in a refrigerator overnight to give crystals. The crystals were collected by filtration to give faint yellow crystals (3.3690 g), which were recrystallized from diisopropyl ether to give colorless granules (2.2479 g) of ethyl 2-(2-nitrobenzylidene)-4,4-diethoxyacetoacetate, m.p. 66° to 67.5° C. This product is one of the two isomers of ethyl 2-(2-nitrobenzylidene)-4,4-diethoxyacetoacetate and shows signal at 5.23 ppm(methine proton) and 8.31 ppm (olefinic proton) on N.M.R. spectrum ($\delta$, CDCl$_3$). The filtrate was condensed and the resultant brown oil, which comprises the two isomers of ethyl 2-(2-nitrobenzylidene)-4,4-diethoxyacetoacetate in the ratio approximately 1:1 and shows signals of 4.93 and 5.23 ppm (methine proton) and 8.17 and 8.31 ppm (olefinic proton) on N.M.R. spectrum ($\delta$, CDCl$_3$).

A mixture of the above obtained crystals (2.4497 g) and ethyl 3-aminocrotonate (1.3508 g) was heated at 75° to 82° C. with stirring under slightly reduced pressure for four hours and further heated at 105° to 108° C. for five hours. The reaction mixture was cooled and crystallized. The resultant crystals were recrystallized from a mixture of diisopropyl ether and n-hexane to give crystals (0.5128 g) of diethyl 2-methyl-4-(2-nitrophenyl-6-diethoxymethyl-1,4-dihydropyridine-3,5-dicarboxylate which was identified with the product of the above Example 1-4)-(1).

(5) A solution of 3-nitrobenzaldehyde (2.27 g), ethyl 4,4-diethoxyacetoacetate (3.28 g) and piperidine (0.2 ml) in benzene (15 ml) was refluxed under azeotropic dehydration for 3 hours. The resultant solution was washed three times with water and dried over magnesium sulfate. The solvent was removed from the reaction solution to give oily ethyl 2-(3-nitrobenzylidene)-4,4-diethoxyacetoacetate (6.0 g). The mixture of the compound obtained above and ethyl 3-aminocrotonate (1.94 g) was heated at about 95° to 100° C. for 7 hours and then at about 120° C. for 1.5 hours with stirring. After cooling, the resultant oil was extracted with ethyl acetate and the extract was washed with water and dried. The solvent was removed from the resultant solution to give an oil (7.8 g). The product was purified by column chromatography on silica gel with an eluent (benzene: ethyl acetate=20:1) to give the pure product of diethyl 2-methyl-4-(3-nitrophenyl)-6-diethoxymethyl-1,4-dihydropyridine-3,5-dicarboxylate (4.65 g).

I.R. Spectrum (Film)
$\nu$(cm$^{-1}$): 3400, 1690, 1615, 1530, 1480, 1350, 1280, 1200, 1090, 920, 765

N.M.R. Spectrum ($\delta$, CDCl$_3$)
ppm: 1.23, 1.26 (12H, t, t, t, J=7 Hz) 2.4 (3H, s), 3.5 to 3.86 (4H, m), 4.11 (4H, q, J=7Hz), 5.16 (1H, s), 6.82 (1H, broad), 7.25 to 8.16 (4H, m)

(6) A mixture of ethyl 2-(2-trifluoromethylbenzylidene)-4,4-diethoxyacetoacetate (7.48 g) and ethyl 3-aminocrotonate (2.582 g) was heated at 130° C. for 5 hours. The resultant mixture was dissolved in ethyl acetate and solution was washed with water twice, dried over magnesium sulfate and concentrated under reduced pressure to give a red oil (9.8 g). The oil was subjected to column chromatography on silica gel with an eluent (a mixture of 20 parts of benzene and one part of diethyl ether by volume) to give an oily substance. This substance turned into crystals, which were recrystallized from a mixture of n-hexane and diethyl ether to give crystals of diethyl 2-methyl-4-(2-trifluoromethylphenyl)-6-diethoxymethyl-1,4-dihydropyridine-3,5-dicarboxylate, m.p. 82° to 83° C.

(7) A solution of 2-methoxybenzaldehyde (2.7228 g), ethyl 4,4-diethoxyacetoacetate (4.3648 g) and piperidine (4 or 5 drops) in benzene (20 ml) was refluxed under azeotropic dehydration for 3 hours. The resultant solution was washed with water and dried. The solvent was removed from the extract to give oily ethyl 2-(2-methoxybenzylidene)4,4-diethoxyacetoacetate. The mixture of the compound obtained above and ethyl 3-aminocrotonate (2.5832 g) was heated in an oil bath (about 100° C.) for 7 hours. After cooling, the reaction mixture was extracted with diethyl ether, and the extract was washed with water twice and dried over magnesium sulfate. The solvent was removed to give a red oil. The oil was purified by a column chromatography on silica gel with an eluent (benzene: ethyl acetate=20:1) to give diethyl 2-methyl-4-(2-methoxyphenyl)-6-diethoxymethyl-1,4-dihydropyridine-3,5-dicarboxylate (5.0779 g). The product was recrystallized from n-hexane to give pale yellowish prisms, m.p. 105° and 107° C.

(8) A mixture of 2-chloro-5-nitrobenzaldehyde (3.73 g), ethyl 4,4-diethoxyacetoacetate (4.365 g) and piperidine (272.5 mg) in benzene (10 ml) was refluxed under azeotropic dehydration for 1.5 hours. To the mixture was added ethyl acetate, and the resultant mixture was washed three times with water and then with an aqueous solution of sodium chloride, and dried over magnesium sulfate. The solvent was removed under reduced pressure to give a reddish brown oil (7.87 g) of ethyl 2-(2-chloro-5-nitrobenzylidene)-4,4-diethoxyacetoacetate. The mixture of thus obtained reddish brown oil and ethyl 3-aminocrotonate (3.48 g) was heated with stirring at 105° to 107° C. in an oil bath for 4.5 hours. The resultant mixture was extracted with ethyl acetate, and the extract was washed with water three times and then with an aqueous solution of sodium chloride, and dried over magnesium sulfate. After removal of the solvent from the extract, the obtained residue (10.87 g) was subjected to column chromatography on silica gel with an eluent (a mixture of 20 parts of chloroform and one part of ethyl acetate by volume). The fractions were checked with thin-layer chromatography and crystals (6.02 g) were obtained by removing the solvent from the fraction containing the designated substance. The crystals were recrystallized from a mixture of diethyl ether and n-hexane to give crystals and diethyl 2-methyl-4-(2-chloro-5-nitrophenyl)-6-diethoxymethyl-1,4-dihydropyridine-3,5-dicarboxylate, m.p. 117° to 118° C.

(9) A solution of thiophene-2-carbaldehyde (2.2430 g), ethyl 4,4-diethoxyacetoacetate (4.3648 g) and piperidine (4 drops) in benzene (20 ml) was refluxed under azeotropic dehydration for 4.5 hours. After cooling, to the resultant solution was added diethyl ether, and the solution was washed with water and dried. The solvent was removed from the reaction mixture to give oily ethyl 2-(2-thenylidene)-4,4-diethoxyacetoacetate.

The mixture of the compound obtained above and ethyl 3-aminocrotonate (2.6 g) was heated in an oil bath (about 100° C.) for 7.5 hours. The resultant mixture was dissolved in diethyl ether, washed with water and dried. The solvent was removed to give brown oil (9.0 g). The oil was purified by column chromatography on silica gel with an eluent (benzene: ethyl acetate=20:1) to give diethyl 2-methyl-4-(2-thienyl)-6-diethoxymethyl-1,4-dihydropyridine-3,5-dicarboxylate. The product was recrystallized from n-hexane to give yellowish crystals (2.2056 g), m.p. 77° to 77.5° C.

(10) To a mixture of 2-furaldehyde (2.88 g) and ethyl 4,4-diethoxyacetoacetate (6.55 g) in benzene (15 ml) was added each one fourth portion of piperidine (408 mg) with an interval of 15 minutes under refluxing with azeotropic dehydration. Thus obtained mixture was refluxed for another 30 minutes. To the reaction mixture was added ethyl acetate, and the resultant mixture was washed with water three times and then with an aqueous solution of sodium chloride and dried over magnesium sulfate. The solvent was removed to give a reddish brown oil (9.47 g) of ethyl 2-(2-furfurylidene)-4,4-diethoxyacetoacetate. Then the mixture of the oil gained above the ethyl 3-aminocrotonate (5.9 g) was heated at 105° C. under stirring for 7 hours. The resultant mixture was extracted with ethyl acetate, and the extract was washed with water and an aqueous solution of sodium chloride and then dried over magnesium sulfate. After removal of the solvent, the resultant oil was purified by column chromatography on silica-gel with an eluent (a mixture of 20 parts of chloroform and one part of ethyl acetate by volume) and crystallized from n-hexane (3 ml). The obtained crystals were washed with n-hexane to result crystals (7.05 g). The resultant crystals (500 mg) were recrystallized from n-hexane to give crystals (450 mg) of diethyl 2-methyl-4-(2-furyl)-6-diethoxymethyl-1,4-dihydropyridine-3,5-dicarboxylate, m.p. 59° to 60° C.

(11) A mixture of 2-nitrobenzaldehyde (3.02 g), 2-ethoxyethyl acetoacetate (3.48 g) and piperidine (272.5 mg) in benzene (10 ml) was refluxed under azeotropic dehydration for 1.5 hours. The mixture was washed with water three times and with an aqueous solution of sodium chloride, dried over magnesium sulfate and concentrated. To the resultant oil of 2-ethoxyethyl 2-(2-nitrobenzylidene)acetoacetate was added ethyl 3-amino-4,4-diethyoxycrotonate (4.77 g) and the mixture was heated at 110° C. under stirring for 5 hours. The reaction mixture was extracted with ethyl acetate and the extract was washed with water three times and dried over magnesium sulfate. After removal of the solvent, the resultant brown oil was purified by column chromatography with an eluent (a mixture of ten parts of benzene and one part of ethyl acetate by volume) to give an oil (3.18 g) of 2-ethoxyethyl 2-methyl-4-(2-nitrophenyl)-5-ethoxycarbonyl-6-diethoxymethyl-1,4-dihydropyridine-3-carboxylate.

I.R. Spectrum (film)
$\nu(cm^{-1})$: 3420, 1730, 1695, 1650, 1610, 1530, 1480, 1355, 1275, 1210, 1100, 860, 830, 785, 752, 715

N.M.R. Spectrum ($\delta$, $CDCl_3$)
ppm: 1 to 1.37 (12H, m), 2.37 (3H, s), 3.28 to 4.3 (12H, m), 5.93 (1H, s), 6.2 (1H, s), 6.78 (1H, m), 7.23 to 7.83 (4H, m)

(12) A mixture of 2-nitrobenzaldehyde (4.536 g), 2-chloroethyl acetoacetate (4.94 g) and piperidine (110 mg) in benzene (18 ml) and acetic acid (360 mg) was refluxed for an hour under azeotropic dehydration. The reaction mixture was washed with water and dried. The solvent was distilled off to give an reddish oil of 2-chloroethyl 2-(2-nitrobenzylidene)acetoacetate, and thus obtained oil was treated with ethyl 3-amino-4,4-diethoxycrotonate (7.1 g) to give yellow granules of 2-chloroethyl 2-methyl-4-(2-nitrophenyl)-5-ethoxycarbonyl-6-diethoxymethyl-1,4-dihydropyridine-3-carboxylate, m.p. 82° to 84° C. (recrystallized from diisopropyl ether).

(13) A mixture of 2-nitrobenzaldehyde (3.023 g), benzyl acetoacetate (3.802 g) and piperidine (272.5 mg) in benzene (10 ml), was treated in a substantially similar manner that of Example 1-11) to give a brown oil (6.94 g) of benzyl 2-(2-nitrobenzylidene)acetoacetate, which was further treated with ethyl 3-amino-4,4-diethoxycrotonate (4.34 g) to give a dark brown oil (10.3 g). This oil was purified by column chromatography on silica-gel and the resultant oil (3.8 g) was crystallized to give crystals (1.65 g) of benzyl 2-methyl-4-(2-nitrophenyl)-5-ethoxycarbonyl-6-diethoxymethyl-1,4-dihydropyridine-3-carboxylate, m.p. 103° to 103.5° C. (recrystallized from a mixture of diisopropyl ether and n-hexane).

(14) In an essentially similar manner to that of Example 1-11) given in the above, the following compounds were obtained:

Starting from a mixture of 2-nitrobenzaldehyde (3.02 g), 2-benzyloxyethyl acetoacetate (4.72 g), piperidine (272.5 mg) in benzene (10.8 ml) was obtained 2-benzyloxyethyl 2-(2-nitrobenzylidene)acetoacetate, which was further treated with ethyl 3-amino-4,4-diethoxycrotonate to give an oil (4.80 g) of 2-benzyloxyethyl 2-methyl-4-(2-nitrophenyl)-5-ethoxycarbonyl-6-diethoxymethyl-1,4-dihydropyridine-3-carboxylate.

I.R. Spectrum (film)
$\nu(cm^{-1})$: 3400, 1700, 1650, 1610, 1530, 1480 1355, 1273, 1205, 1090, 1055, 750, 700

N.M.R. Spectrum ($\delta$, CDCl$_3$)
ppm: 1.1 to 1.3 (9H, m), 2.32 (3H, s), 3.45 to 4.32 (10H, m), 4.46 (2H, s), 5.94 (1H, s), 6.2 (1H, s), 6.82 (1H, s), 7.16 to 7.74 (9H, m)

(15) In an essentially similar manner to that of Example 1-11) given in the above, the following compounds were obtained:

Starting from a mixture of 2-nitrobenzaldehyde (3.02 g), 2-phenoxyethyl acetoacetate (4.44 g), piperidine (272.5 mg) in benzene (10.8 ml) was obtained an oil (8.0 g) of 2-phenoxyethyl 2-(2-nitrobenzylidene)acetoacetate. Thus obtained oil was treated with ethyl 3-amino-4,4-diethoxycrotonate (4.34 g) to give an oil of 2-phenoxyethyl 2-methyl-4-(2-nitrophenyl)-5-ethoxycarbonyl-6-diethoxymethyl-1,4-dihydropyridine-3-carboxylate.

I.R. Spectrum (film)
$\nu(cm^{-1})$: 3410, 1700, 1602, 1555, 1480, 1356, 1277, 1250, 1210, 1100, 1060, 755, 695

N.M.R. Spectrum ($\delta$, CDCl$_3$)
ppm: 1.13 (3H, t, J=7 Hz), 1.23 (6H, t, J=7 Hz)
2.33 (3H, s),
3.41 to 4.47 (10H, m),
5.91 (1H, s),
6.17 (1H, s),
6.71 to 7.71 (9H, m)

(16) A mixture of 3-nitrobenzaldehyde (4.54 g), 2-ethoxyethyl acetoacetate (5.23 g) and piperidine (85.2 mg) in benzene (15 ml) was refluxed under azeotropic dehydration for 3 hours. The resultant mixture was washed with water, an aqueous solution saturated with sodium chloride and water in turn, dried and concentrated to give an oil of 2-ethoxyethyl 2-(3-nitrobenzylidene)acetoacetate. To this oily product was added ethyl 3-amino-4,4-diethoxycrotonate (6.5 g). The mixture was heated at 110° C. for about 3 hours. The reaction mixture was dissolved in ethyl acetate and washed with water twice and dried. The solvent was removed from the mixture to give an oil (15.58 g). This oil was subjected to column chromatography on silica gel with an eluent (a mixture of 10 parts of benzene and one part of ethyl acetate by volume) to give an oily substance (8.09 g). This oily substance (0.93 g) was treated with a mixture of n-hexane and diethyl ether to give crystals, which were further recrystallized from a mixture of n-hexane and diethyl ether to give yellow granules (565.2 mg) of 2-ethoxyethyl 2-methyl-4-(3-nitrophenyl)-5-ethoxycarbonyl-6-diethoxymethyl-1,4-dihydropyridine-3-carboxylate, m.p. 99° to 100° C.

(17) A mixture of 2-chloroethyl 2-(3-nitrobenzylidene)acetoacetate (16 g) and ethyl 3-amino-4,4-diethoxycrotonate (10.85 g) was heated at 100° C. for 3 hours and allowed to stand overnight at room temperature. Appearing crystals were collected by filtration to give yellow crystals (7.02 g), and then the filtrate was subjected to column chromatography on silica gel with an eluent [a mixture of 20 parts of benzene and one part of ethyl acetate by volume] to give an oil (7.4 g). The oil was allowed to stand to give crystals (3.6 g) and put together with the above obtained crystals (7.02 g). These crystals were recrystallized from a mixture of n-hexane and diethyl ether to give 2-chloroethyl 2-methyl-4-(3-nitrophenyl)-5-ethoxycarbonyl-6-diethoxymethyl-1,4-dihydropyridine-3-carboxylate, m.p. 96° to 97° C.

(18) A mixture of ethyl 2-(3-hydroxybenzylidene)-acetoacetate (2.1 g) and ethyl 3-amino-4,4-diethoxy-crotonate (1.95 g) in n-propyl alcohol (1.5 ml) was heated at 105° C. for 4.5 hours. After removal of the solvent from the reaction mixture under reduced pressure, ethyl acetate was added to the residue. The resultant solution was washed with water twice and an aqueous sodium chloride solution in turn, and then dried over magnesium sulfate. The solvent was removed from the solution to give red oil (4.2 g). The oil was subjected to column chromatography on silica gel with an eluent [a mixture of 10 parts of benzene and one part of diethyl ether by volume] to give an oily substance, which was crystallized from n-hexane to give crystals (1.5 g). These crystals (280 mg) were recrystallized from a mixture of n-hexane and diethyl ether to give crystals of diethyl 2-methyl-4-(3-hydroxyphenyl)-6-diethoxymethyl-1,4-dihydropyridine-3,5-dicarboxylate (106.2 mg), m.p. 107° to 108° C.

(19) A solution of 2-chlorobenzaldehyde (351.4 mg), ethyl 4,4-diethoxyacetoacetate (545.6 mg) and ethyl 3-aminocrotonate (322.9 mg) in n-propanol (2 ml) was refluxed for 10 hours. The resultant solution was concentrated, and the residue was dissolved in ether, and then washed twice with water. After drying the extract over magnesium sulfate, the solvent was removed from the extract to give orange oil (1.1765 g). The oil was purified by a column chromatography on silica gel with an eluent (benzene:ethyl acetate=20:1) to give oily diethy 2-methyl-4-(2-chlorophenyl)-6-diethoxymethyl-,4-dihydropyridine-3,5-dicarboxylate (374.6 mg). The product was dissolved in n-hexane and allowed to stand in a refrigerator, and the precipitated crystals were collected by filtration and washed with n-hexane to give pure crystals, m.p. 75° to 77° C.

(20) A mixture of ethyl 2-(2-chlorobenzylidene)-4,4-diethoxyacetoacetate (2.42 g), ammonium acetate (1 g) and methyl propiolate (1 ml) in acetic acid (1 ml) was refluxed for 30 minutes. The reaction mixture was poured into an aqueous solution of sodium bicarbonate and extracted twice with ethyl acetate. The ethyl acetate layer was washed with water and then with a saturated aqueous solution of sodium chloride, dried, and further concentrated. The resultant red oil was dissolved in diethyl ether and appeared crystals were filtered off. The filtrate was concentrated to give a brown oil (2.57 g). This oil was purified by colomn chromatography on silica-gel with an eluent (a mixture of ten parts of benzene and one part of ethyl acetate by volume). The fraction containing the designated substance was concentrated to give a yellow oil (1.03 g) of methyl 4-(2-chlorophenyl)-5-ethoxycarbonyl-6-diethoxymethyl-1,4-dihydropyridine-3-carboxylate.

I.R. Spectrum (film)
$\nu(cm^{-1})$: 3350, 1700, 1590, 760
N.M.R. Spectrum ($\delta$, CDCl$_3$)
ppm: 5.45 (1H, s), 6.20 (1H, s)

(21) Similarly, the following compounds were obtained:

(1) 2-(N-Benzyl-N-methylamino)ethyl 2-methyl-4-(3-nitrophenyl)-5-ethoxycarbonyl-6-diethoxymethyl-1,4-dihydropyridine-3-carboxylate.

I.R. Spectrum (film)
$\gamma(cm^{-1})$: 3400, 1700, 1690, 1610, 1523, 1475, 1350, 1275, 1197, 1092, 1055, 755, 698
N.M.R. Spectrum ($\delta$: CDCl$_3$+D$_2$O)
ppm: 1.21 (9H, t, J=7 Hz), 2.21 (3H, s), 2.36 (3H, s), 2.63 (2H, t, J=6 Hz), 3.5 (2H, s), 3.65 (2H, q, J=7 Hz), 3.66 (2H, q, J=7 Hz), 4.1 (2H, q), 4.18 (2H, t, J=6 Hz), 5.18 (1H, s), 6.2 (1H, s), 6.86 (1 H, s), 7.16 to 8.16 (4H, m)

(2) 2-N,N-Diethylaminoethyl 2-methyl-4-(3-nitrophenyl)-5-ethoxycarbonyl-6-diethoxymethyl-1,4- dihydropyridine-3-carboxylate (a brown oil).

(3) 2-Hydroxyethyl 2-methyl-4-(3-nitrophenyl)-5-ethoxycarbonyl-6-diethoxymethyl-1,4-dihydropyridine-3-carboxylate, m.p. 98° to 100° C.

(4) 2-hydroxyethyl 2-methyl-4-(2-nitrophenyl)-5-ethoxycarbonyl-6-diethoxymethyl-1,-4-dihydropyridine-3-carboxylate.

I.R. Spectrum (film)
$\nu(cm^{-1})$: 3530, 3410, 3360 (shoulder), 1706 (shoulder), 1697, 1690 (shoulder), 1532, 1480, 1356, 1275, 1208, 1100, 1105, 860, 832, 785
N.M.R. Spectrum ($\delta$, CDCl$_3$)
ppm: 1.0 to 1.45 (9H, m), 2.39 (3H, s), 2.2 to 2.73 (1H, broad), 3.4 to 4.5 (10H, m), (5) Diethyl 2-methyl-4-(2-nitrophenyl)-6-ethylenedioxymethyl-1,4-dihydropyridine-3,5-dicarboxylate, m.p. 152° to 153.5° C.

EXAMPLE 2

(1) To a solution of diethyl 2,6-bis(diethoxymethyl)-4-(2-chlorophenyl)-1,4-dihydropyridine-3,5-dicarboxylate (1.7 g) in acetone (17 ml) was added 6N-hydrochloric acid (1.5 ml) and stirred at room temperature for 3 hours. After removing the solvent, the residue was extracted with diethyl ether and the extract was washed with water and dried. The solvent was removed from the extract to give diethyl 2,6diformyl-4-(2-chlorophenyl)-1,4-dihydropyridine-3,5-dicarboxylate (1.35 g). The product was recrystallized from diethyl ether to give pure yellowish granules, m.p. 85° to 86° C.

(2) To a solution of diethyl 2-methyl-4-(2-chlorophenyl)-6-diethoxymethyl-1,4-dihydropyridine-3,5-dicarboxylate (452 mg) in acetone (5 ml) was added 6N-hydrochloric acid (0.2 to 0.3 ml) and stirred at room temperature for an hour. After removing acetone, the residue was extracted with ethyl acetate twice and the extract was washed with water and dried. The solvent was removed from the extract to give diethyl 2-methyl-4-(2-chlorophenyl)-6-formyl-1,4-dihydropyridine-3,5-dicarboxylate. The product was recrystallized from a mixture of n-hexane and diethyl ether to give the pure product, m.p. 87° to 88° C.

(3) To a solution of dimethyl 2-methyl-4-(2-chlorophenyl)-6-(1,1-dimethoxyethyl)-1,4-dihydropyridine-3,5-dicarboxylate (409.9 mg) in acetone (5 ml) was added 6 N hydrochloric acid (0.5 ml) and stirred at room temperature for 17 minutes. The reaction mixture was neutralized with an aqueous solution saturated with sodium bicarbonate and the solvent was distilled off under reduced pressure. Water was added to the residue and the mixture was allowed to stand to give crystals, which were collected by filtration and dried to give crystals (350.2 mg). These crystals were recrystallized from a mixture of n-hexane and ethyl acetate to give yellow granules of dimethyl 2-methyl-4-(2-chlorophenyl)-6-acetyl-1,4-dihydropyridine-3,5-dicarboxylate, m.p. 161° to 162° C.

(4) To a solution of diethyl 2-methyl-4-(2-nitrophenyl)-6-diethoxymethyl-1,4-dihydropyridine-3,5-dicarboxylate (1.1563 g) in acetone (10 ml) was added 6N-hydrochloric acid (2.5 ml) and stirred at room temperature for 30 minutes. After removing acetone, water was added to the residue and neutralized with aqueous solution of sodium bicarbonate. The precipitated solid was collected by filtration, washed with water and then dried to give yellowish powder to diethyl 2-methyl-4-(2-nitrophenyl)-6-formyl-1,4-dihydropyridine-3,5-dicarboxylate (0.9407 g). The product was recrystallized for a mixture of ethanol and n-hexane to give the pure product, m.p. 101°to 103° C.

(5) To a solution of diethyl 2-methyl-4-(3-nitrophenyl)-6-diethoxymethyl-1,4-dihydropyridine-3,5-dicarboxylate (462.5 mg) in acetone (4 ml) was added 6N-hydrochloric acid (0.4 ml) and stirred at room temperature for an hour. After the reaction, the solvent was removed from the resultant solution. To the residue was added water, and the residue was pulverized. The powder was collected by filtration, washed with water and dried to give diethyl 2-methyl-4-(3-nitrophenyl)-6-formyl-1,4-dihydropyridine-3,5-dicarboxylate (360 mg), m.p. 130° to 133° C.

(6) To a solution of diethyl 2-methyl-4-(2-trifluoromethylphenyl)-6-diethoxymethyl-1,4-dihydropyridine-3,5-dicarboxylate (5.2 g) in acetone (5 ml) was added 6N-hydrochloric acid (5 ml) and stirred at room temperature for about 1.5 hours. After removal of the acetone, water was added to the residue and the resultant aqueous solution was extracted with ethyl acetate twice. The extract was washed with water and dried and the solvent was removed therefrom to give a reddish oil (4.2 g) of diethyl 2-methyl-4-(2-trifluoromethylphenyl)-6-formyl-1,4-dihydropyridine-3,5-dicarboxylate.

I.R. Spectrum (Nujol)
$\nu(cm^{-1})$: 3350, 1700, 1640, 1605, 1480, 1370, 1308, 1200, 1100, 1035, 950, 763
N.M.R. Spectrum ($\delta$: CDCl$_3$+D$_2$O)
ppm: 1.2 (6H, t, J=7 Hz), 2.4 (3H, s), 3.92 to 4.38 (4H, m), 5.72 (1H, s), 7.06 (1H, s), 7.24 to 7.62 (4H, m)

(7) To a solution of diethyl 2-methyl-4-(2-methoxyphenyl)-6-diethoxymethyl-1,4-dihydropyridine-3,5-dicarboxylate (447.5 mg) in acetone (7.5 ml) was added 6N-hydrochloric acid (0.2 ml) and stirred at room temperature for an hour. The resultant mixture was treated in a similar manner to Example 2-4), to give reddish yellow crystals of diethyl 2-methyl-4-(2-methoxypheny)-6-formyl-1,4-dihydropyridine-3,5-dicarboxylate (373.2 mg). The product was recrystallized from a mixture of diethyl ether and n-hexane to give the pure product, m.p. 111° to 112° C.

(8) To a solution of diethyl 2-methyl-4-(2-chloro-5-nitrophenyl)-6-diethoxymethyl-1,4-dihydropyridine-3,5-dicarboxylate (5.45 g) in acetone (54.5 ml) was added 6N hydrochloric acid (5 ml) and the resultant mixture was stirred at room temperature for 1.5 hours. After removal of the acetone from the reaction mixture, water was added to the residue and the mixture was allowed to stand for 15 minutes. The precipitated crystals were collected by filtration, washed with water and dried to give crystals (4.2 g). Thus obtained crystals (500 mg) were recrystallized from a mixture of n-hexane and ethyl acetate to give crystals (347 mg) of diethyl 2-methyl-4-(2-chloro-5-nitrophenyl)-6-formyl-1,4-dihydropyridine-3,5-dicarboxylate, m.p. 172° to 173° C.

(9) To a solution of diethyl 2-methyl-4-(2-thienyl)-6-diethoxymethyl-1,4-dihydropyridine-3,5-dicarboxylate (424 mg) in acetone (15 ml) was added 6N-hydrochloric acid (0.2 ml) and this solution was stirred at room temperature for an hour. The resultant solution was concentrated and the residue was extracted with diethyl ether. The extract was washed with water and dried and then the solvent was removed to give yellowish oil of diethyl 2-methyl-4-(2-thienyl)-6-formyl-1,4-dihydropyridine-3,5-dicarboxylate, which was soon crystallized. The product was recrystallized from a mixture of n-hexane and diethyl ether to give the pure product (247.7 mg), m.p. 67° to 68.5° C.

(10) To a solution of diethyl 2-methyl-4-(2-furyl)-6-diethoxymethyl-1,4-dihydropyridine-3,5-dicarboxylate (6.6 g) in acetone (66 ml) was added 6 N hydrochloric acid (6.6 ml) and the resultant mixture was stirred for one and three-fourth hour at room temperature. After removal of the acetone from the reaction mixture, the residue was extracted with ethyl acetate. The extract was washed with water, dried and concentrated. The resultant oil (6.1 g) was subjected to column chromatography on silica-gel with an eluent (a mixture of 20 parts of chloroform and one part of ethyl acetate by volume). The concentrate (oil, 2.4 g) of the fraction of the eluate which showed one spot on thin-layer chromatography gave crystals (1.79 g) and the concentrate (700 mg) of the fraction of the eluent which showed plural spots on thin-layer chromatography gave crystals (410 mg). These crystals were combined together and recrystallized from n-hexane to give needles (400 mg) of diethyl 2-methyl-4-(2-furyl)-6-formyl-1,4-dihydropyridine-3,5-dicarboxylate, m.p. 78° to 79.5° C.

(11) Starting from a mixture of 2-ethoxyethyl 2-methyl-4-(2-nitrophenyl)-5-ethoxycarbonyl-6-diethoxymethyl-1,4-dihydropyridine-3-carboxylate (1.9 g) in acetone (19 ml) and 6 N hydrochloric acid (1.9 ml), was obtained, by applying an essentially similar manner to that of Example 2-1), crystals of 2-ethoxyethyl 2-methyl-4-(2-nitrophenyl)-5-ethoxycarbonyl-6-formyl-1,4-dihydropyridine-3-carboxylate, m.p. 107° to 108° C. (recrystallized from diisopropyl ether).

(12) To a solution of 2-hydroxyethyl 2-methyl-4-(2-nitrophenyl)-5-ethoxycarbonyl-6-diethoxymethyl-1,4-dihydropyridine-3-carboxylate (2.5 g) in acetone (30 ml) was added 6 N hydrochloric acid (1 ml) and treated in a substantially similar manner to those of Example 2-6) to give a viscous oil (2.10 g) of 2-hydroxyethyl 2-methyl-4-(2-nitrophenyl)-5-ethoxycarbonyl-6-formyl-1,4-dihydropyridine-3-carboxylate.

N.M.R. Spectrum ($\delta$, CDCl$_3$)
ppm: 6.07 (1H, s), 10.43 (1H, s)

(13) In a substantially similar manner to that of Example 2-6), was treated a mixture of benzyl 2-methyl-4-(2-nitrophenyl)-5-ethoxycarbonyl-6-diethoxymethyl-1,4-dihydropyridine-3-carboxylate (1.5 g) in acetone (15 ml) and 6 N hydrochloric acid (1.5 ml) to give a reddish brown oil which was crystallized and washed with n-hexane to give crystals (1.30 g) of benzyl 2-methyl-4-(2-nitrophenyl)-5-ethoxycarbonyl-6-formyl-1,4-dihydropyridine-3-carboxylate.

I.R. Spectrum (Nujol)
$\nu$(cm$^{-1}$): 3400, 1699, 1673, 1608, 1530, 1490, 1380, 1355, 1220, 1110, 1030, 835, 795

N.M.R. Spectrum ($\delta$, CDCl$_3$)
ppm: 1.21 (3H, t, J=7 Hz), 2.38 (3H, s), 4 to 4.4 (2H, m), 5.07 (2H, s), 6.01 (1H, s), 6.9 (1H, broad s), 7.25 to 7.8 (9H, m), 10.33 (1H, s)

(14) Starting from a mixture of an oil (2.5 g) of 2-benzyloxyethyl 2-methyl-4-(2-nitrophenyl)-5-ethoxycarbonyl-6-diethoxymethyl-1,4-dihydropyridine-3-carboxylate in acetone (25 ml) and 6 N hydrochloric acid (2 ml) was obtained a reddish oil (2.05 g) of 2-benzyloxyethyl 2-methyl-4-(2-nitrophenyl)-5-ethoxycarbonyl-6-formyl-1,4-dihydropyridine-3-carboxylate, in a substantially similar manner to that of Example 2-6).

I.R. Spectrum (film)
$\nu$(cm$^{-1}$): 3380, 1695, 1532, 1485, 1277, 1210, 1100, 1040, 860, 750

N.M.R. Spectrum ($\delta$, CDCl$_3$)
ppm: 2.40 (3H, s), 4.48 (2H, s), 6.08 (1H, s), 10.40 (1H, s)

(15) Starting from a mixture of 2-phenoxyethyl 2-methyl-4-(2-nitrophenyl)-5-ethoxycarbonyl-6-diethoxymethyl-1,4-dihydropyridine-3-carboxylate (1.24 g) in acetone (12 ml) and 6 N hydrochloric acid (1.2 ml) was obtained an oil (1.1 g) of 2-phenoxyethyl 2-methyl-4-(2-nitrophenyl)-5-ethoxycarbonyl-6-formyl-1,4-dihydropyridine-3-carboxylate, in a substantially similar manner to that of Example 2-6).

I.R. Spectrum (film)
$\nu$(cm$^{-1}$): 3400, 1700, 1640, 1600, 1530, 1480, 1350, 1240, 1200, 1100, 860, 785 755, 692

N.M.R. Spectrum ($\delta$, CDCl$_3$)
ppm: 1.2 (3H, t, J=7 Hz), 2.4 (3H, s), 3.98 to 4.46 (6H, m), 6.03 (1H, s), 6.71 to 7.76 (9H, m), 10.4 (1H, s)

(16) To a solution of 2-ethoxyethyl 2-methyl-4-(3-nitrophenyl)-5-ethoxycarbonyl-6-diethoxymethyl-1,4-dihydropyridine-3-carboxylate (5.85 g) in acetone (60 ml) was added 6 N hydrochloric acid (3 ml) and the resultant mixture was stirred at room temperature for about 2 hours. The solvent was distilled off under reduced pressure and water added to the residue. The mixture was extracted with ethyl acetate twice and the extract was washed with an aqueous sodium chloride solution and dried. The solvent was distilled off to give a reddish oil (5.7 g), which was turned into crystals. These crystals were pulverized with a mixture of n-hexane and diethyl ether and the resultant powder (4.81 g) was collected by filtration. The powder (1.81 g) was recrystallized from a mixture of diethyl ether and ethyl acetate to give orange-yellow granules (1.2 g) of 2-ethoxyethyl 2-methyl-4-(3-nitrophenyl)-5-ethoxycarbonyl-6-formyl-1,4-dihydropyridine-3-carboxylate, m.p. 100° to 101° C.

(17) To a solution of 2-(N-methyl-N-benzylamino)ethyl 2-methyl-4-(3-nitrophenyl)-5-ethoxycarbonyl-6-diethoxymethyl-1,4-dihydropyridine-3-carboxylate (7.25 g) in acetone (70 ml) was added 6N-hydrochloric acid (7 ml) and the resultant mixture was stirred at room temperature for 3 hours. The solvent was distilled off under reduced pressure. Water was added to the residue, where an oily substance appeared. The aqueous mixture was adjusted to an alkaline medium by addition of power of sodium bicarbonate, and then extracted with ethyl acetate. The extract was washed with water and dried, and the solvent was distilled off under reduced pressure to give a reddish oil (5.8 g) of 2-(N-methyl-N-benzylamino)ethyl 2-methyl-4-(3-nitrophenyl)-5-ethoxycarbonyl-6-formyl-1,4-dihydropyridine-3-carboxylate.

N.M.R. Spectrum (δ: CDCl₃+D₂O)
ppm: 1.29 (3H, t, J=7 Hz), 2.21 (3H, s) 2.45 (3H, s), 2.63 (2H, t, J=6 Hz), 3.51 (2H, s), 3.95 to 4.42 (2H, t), 3.95 to 4.42 (2H, q), 5.28 (1H, s), 7.08 (1H, s), 7.28 to 8.12 (4H, m), 10.54 (1H, s)

I.R. Spectrum (Film)
$\nu$(cm$^{-1}$): 3350, 1735, 1700, 1690, 1635, 1600, 1525, 1480, 1350, 1279, 1215, 1100, 1030, 735

(18) To a mixture of a brown oil (2.46 g) of 2-(N,N-diethylamino)ethyl 2-methyl-4-(3-nitrophenyl)-5-ethoxycarbonyl-6-diethoxymethyl-1,4-dihydropyridine-3-carboxylate in acetone (24.6 ml) was added 6 N hydrochloric acid (2.46 ml) and this mixture was stirred for two hours at room temperature. The reaction mixture was adjusted to pH 7 with an aqueous solution of sodium bicarbonate and the acetone was distilled off. The residue was extracted with ethyl acetate, and the extract was washed with water, dried, and concentrated to give an oil (1.81 g) of 2-(N,N-diethylamino)ethyl 2-methyl-4-(3-nitrophenyl)-5-ethoxycarbonyl-6-formyl-1,4-dihydropyridine-3-carboxylate.

N.M.R. Spectrum (δ, CDCl₃)
ppm: 2.03 (3H, s), 5.3 (1H, s), 10.47 (1H, s)

(19) To a mixture of diethyl 2-methyl-4-(3-hydroxyphenyl)-6-diethoxymethyl-1,4-dihydropyridine-3,5-dicarboxylate (1.16 g) in acetone (10 ml) was added 6 N hydrochloric acid (1 ml) and this mixture was stirred at room temperature for 1.5 hours. The solvent was distilled off under reduced pressure. The residue was added with water and pulverized. The resultant suspension was extracted with ethyl acetate and the extract was washed with water and dried over magnesium sulfate. The solvent was distilled off under reduced pressure and the residue was treated with diethyl ether to give crystals (0.8 g). The crystals (200 mg) was recrystallized from a mixture of n-hexane and diethyl ether to give pure crystals (130 mg) of diethyl 2-methyl-4-(3-hydroxyphenyl)-6-formyl-1,4-dihydropyridine-3,5-dicarboxylate, m.p. 141.5° to 142.5° C.

(20) To a mixture of a yellow oil (360 mg) of methyl 4-(2-chlorophenyl)-5-ethoxycarbonyl-6-diethoxymethyl-1,4-dihydropyridine-3-carboxylate in acetone (10 ml) was added 6 N hydrochloric acid (0.3 ml) and the resultant mixture was stirred for 1.5 hours at room temperature, and the acetone was removed. Water was added to the residue and the mixture was extracted with ethyl acetate. The ethyl acetate layer was washed with water, dried and concentrated. The resultant orange oil (0.26 g) was crystallized and the crystals were washed with n-hexane to give yellowish-orange powder (80.7 mg) of methyl 4-(2-chlorophenyl)-5-ethoxycarbonyl-6-formyl-1,4-dihydropyridine-3-carboxylate.

I.R. Spectrum (Nujol)
$\nu$(cm$^{-1}$): 3300, 1690, 1675, 1491, 1442, 1376, 1303, 1221, 1186, 1090, 1060, 831, 757

N.M.R. Spectrum (δ, CDCl₃)
ppm: 1.0 (3H, t, J=7 Hz), 3.68 (3H, s), 4.18 (2H, q, J=7 Hz), 5.56 (1H, s), 7 to 7.6 (6H, m), 10.44 (1H, s)

EXAMPLE 3

(1) The solution of diethyl 2-methyl-4-(2-chlorophenyl)-6-formyl-1,4-dihydropyridine-3,5-dicarboxylate (377.8 mg), hydroxylamine hydrochloride (83.4 mg) and sodium carbonate (63.6 mg) in ethanol (1 ml) was stirred at room temperature for 30 minutes. After concentrating the resultant solution, to the residue was added water. After the mixture was extracted with ethyl acetate, the extract was washed with water, and dried. The dried extract was concentrated to give yellowish oil (476 mg). The oil was crystallized with n-hexane to give diethyl 2-methyl-4-(2-chlorophenyl)-6-hydroxyiminomethyl-1,4-dihydropyridine-3,5-dicarboxylate (318.8 mg), which was identified by converting to the corresponding 6-cyano compound, m.p. 136° to 137° C.

(2) A mixture of diethyl 2-methyl-4-(2-chlorophenyl)-6-formyl-1,4-dihydropyridine-3,5-dicarboxylate (756 mg) in ethanol (2 ml) and 85% hydrazine hydrate (141 mg) in water (1 ml) was stirred at room temperature for an hour. The ethanol was distilled off under reduced pressure and the residue was extracted with ethyl acetate. The extract was washed with water, dried over magnesium sulfate and concentrated under reduced pressure to give an oil (960 mg). The oil was subjected to a column chromatography on silica gel with an eluent [a mixture of one part of benzene and one part of diethyl ether by volume] to give an oily substance (720 mg), which was allowed to stand for 14 days in a refrigerator to give needles (120 mg) of diethyl 2-methyl-4-(2-chlorophenyl)-6-hydrazonomethyl-1,4-dihydropyridine-3,5-dicarboxylate, m.p. 107° to 110° C.

(3) To a mixture of diethyl 2-methyl-4-(2-chlorophenyl)-6-formyl-1,4-dihydropyridine-3,5-dicarboxylate (525.3 mg) and O-methylhydroxyamine hydrochloride (139.34 mg) in 99% ethanol (6 ml) was dropwise added a solution of sodium carbonate (88.5 mg) in water (1 ml) over the period of 20 minutes under stirring at room temperature. The mixture was stirred for another 10 minutes. The ethanol was distilled off under reduced pressure, and water was added to the residue. The aqueous mixture was extracted with diethyl ether and the extract was washed with water twice and a saturated aqueous solution of sodium chloride, dried and then concentrated under reduced pressure to give a yellow oil. The oil turned into crystals, and these crystals were washed with n-hexane to give yellow powder (504.6 mg). This powder was recrystallized from a mixture of 10 parts of n-hexane and one part of diethyl ether by volume to give yellow glanules (301.5 mg) of diethyl 2-methyl-4-(2-chlorophenyl)-6-methoxyiminomethyl-1,4-dihydropyridine-3,5-dicarboxylate, m.p. 110° to 112° C.

(4) A mixture of diethyl 2-methyl-4-(2-nitrophenyl)-6-formyl-1,4-dihydropyridine-3,5-dicarboxylate (1.1651 g), N,N-dimethyltrimethylenediamine (306.6 mg) and p-toluenesulfonic acid (catalytic amount) in dried benzene (20 ml) was refluxed under azeotropic dehydration for 4.5 hours. The resultant solution was washed with water and dried. The solvent was removed from the solution to give brown oil (1.4748 g) of diethyl 2-methyl-4-(2-nitrophenyl)-6-[3-(N,N-dimethylamino)propyl]iminomethyl-1,4-dihydropyridine-3,5-dicarboxylate.

I.R. Spectrum (Film)
$\nu$(cm$^{-1}$): 3350, 1710, 1695, 1534, 1487, 1280, 1200, 1100, 1043, 860, 828, 785, 753, 715, 680

N.M.R. Spectrum (δ, CDCl₃)

ppm: 1.18 (3H, t), 1.2 (3H, t), 2.25 (6H, s), 2.41 (3H, s), 3.67 (2H, broad t), 3.8 to 4.3 (8H, m), 5.97 (1H, s), 7.2 to 7.8 (4H, m), 7.8 (1H, broad s), 8.97 (1H, t, J=1 Hz)

(5) A mixture of diethyl 2-methyl-4-(2-nitrophenyl)-6-formyl-1,4-dihydropyridine-3,5-dicarboxylate (970.9 mg), N,N-diethylethylenediamine (290.5 mg) and p-toluenesulfonic acid (catalytic amount) in dried benzene (20 ml) was refluxed under azeotropic dehydration for 4 hours. To the resultant solution was added diethyl ether and the solution was washed with water and dried. The solvent was removed to give red oil (1.1711 g) of diethyl 2-methyl-4-(2-nitrophenyl)-6-[2-(N,N-diethylamino)ethyl]iminomethyl-1,4-dihydropyridine-3,5-dicarboxylate.

I.R. Spectrum (Film)
$\nu(cm^{-1})$: 3350, 1700, 1685, 1528, 1475, 1351, 1273, 1090, 852, 821, 788, 746, 708

N.M.R. Spectrum ($\delta$, CDCl$_3$)
ppm: 2.48 (3H, s), 5.99 (1H, s), 8.96 (1H, t, J=1 Hz)

(6) A mixture of diethyl 2-methyl-4-(2-nitrophenyl)-6-formyl-1,4-dihydropyridine-3,5-dicarboxylate (1.1651 g), 2-aminoethanol (185 mg) and p-toluenesulfonic acid (catalytic amount) in dried benzene (20 ml) was refluxed under azeotropic dehydration for 1.5 hours. After cooling to room temperature, water was added to the resultant solution. The mixture was washed twice with water. The aqueous layer was extracted with diethyl ether and the extract was combined with the benzene solution. The mixed solution was dried over magnesium sulfate and then the solvent was removed from the solution to give viscous oil (1.2397 g) of diethyl 2-methyl-4-(2-nitrophenyl)-6-(2-hydroxyethyl)iminomethyl-1,4-dihydropyridine-3,5-dicarboxylate.

I.R. Spectrum (Film)
$\nu(cm^{-1})$: 3500, 3360, 1694, 1536, 1484, 1280, 1220, 1101, 762, 753

N.M.R. Spectrum ($\delta$, CDCl$_3$)
ppm: 1.13 (3H, t, J=7 Hz), 1.20 (3H, t, J=7 Hz), 2 (1H, broad s), 2.38 (3H, s), 3.8 to 4.3 (4H, m), 3.87 (4H, broad s), 5.96 (1H, s), 7.2 to 7.8 (4H, m), 7.8 (1H, broad s), 9.0 (1H, broad s)

(7)-(1) A mixture of diethyl 2-methyl-4-(2-trifluoromethylphenyl)-6-formyl-1,4-dihydropyridine-3,5-dicarboxylate (870 mg), sodium carbonate (112.1 mg) and hydroxylamine hydrochloride (147 mg) in ethanol (5 ml) was stirred at room temperature for 30 minutes. After removal of the ethanol, water was added to residue and the solution was extracted with ethyl acetate. The extract was washed with a saturated aqueous solution of sodium chloride, dried over magnesium sulfate and concentrated under reduced pressure to give pasty oil (0.992 g). The oil was purified by column chromatography on silica gel with an eluent [benzene (10)+ethyl acetate (1)] to give yellow powder (0.52 g) of diethyl 2-methyl-4-(2-trifluoromethylphenyl)-6-hydroxyiminomethyl-1,4-dihydropyridine-3,5-dicarboxylate.

I.R. Spectrum (Nujol)
$\nu(cm^{-1})$: 3410, 1695, 1680, 1655, 1483, 1445, 1370, 1309, 1221, 1106, 1090, 1057, 1034, 1010, 985, 772

N.M.R. Spectrum ($\delta$: CDCl$_3$)
ppm: 1.17 (3H, t, J=7 Hz), 1.20 (3H, t, J=7 Hz), 2.35 (3H, s), 3.8 to 4.4 (4H, m), 5.64 (1H, broad s), 6.91 (1H, broad s), 7.2 to 7.7 (4H, m), 8.4 (1H, broad s), 8.8 (1H, s)

(7)-(2) To a solution of diethyl 2-methyl-4-(2-trifluoromethylphenyl)-6-formyl-1,4-dihydropyridine-3,5-dicarboxylate (1.23 g) and hydroxylamine hydrochloride (250.2 mg) in ethanol (5 ml) was added a solution of sodium carbonate (190.8 mg) in water (1.5 ml). The mixture was stirred at room temperature for 30 minutes and concentrated under reduced pressure. To the residue was added water and the mixture was extracted with ethyl acetate. The extract was washed with a saturated aqueous solution of sodium chloride, dried over magnesium sulfate and concentrated under reduced pressure to give an oil. The oil was crystallized with n-hexane to give crude crystals (1.09 g) of diethyl 2-methyl-4-(2-trifluoromethylphenyl)-6-hydroxyiminoethyl-1,4-dihydropyridine-3,5-dicarboxylate.

(8) To a mixture of 2-(N-methyl-N-benzylamino)ethyl 2-methyl 4-(3-nitrophenyl)-5-ethoxycarbonyl-6-formyl-1,4-dihydropyridine-3-carboxylate (1.015 g) and hydroxylamine hydrochloride (116.8 mg) in ethanol (3 ml) was dropwise added slowly a solution of sodium carbonate (127.2 mg) in water (1 ml) and the resultant mixture was stirred at room temperature for 50 minutes. The ethanol was distilled off under reduced pressure and to the residue was added water and the mixture was extracted with ethyl acetate. The extract was washed with aqueous sodium chloride solution, dried and then concentrated under reduced pressure to give a yellow oil (1.01 g) of 2-(N-methyl-N-benzylamino)ethyl 2-methyl-4-(3-nitrophenyl)-5-ethoxycarbonyl-6-hydroxyiminomethyl-1,4-dihydropyridine-3-carboxylate.

I.R. Spectrum (film)
$\nu(cm^{-1})$: 3350, 1690, 1460, 1375, 1348, 1205, 1098, 1044, 738, 720, 700

N.M.R. Spectrum ($\delta$: CDCl$_3$) ppm: 1.22 (3H, t, J=7 Hz), 2.26 (3H, s), 2.36 (3H, s), 2.70 (2H, t, J=6 Hz), 3.58 (2H, s), 4.09 (2H, q, J=7 Hz), 4.18 (2H, t, J=6 Hz), 5.14 1H, s), 7.1 to 8.1 (10H, m), 8.97 (1H, s)

(9) According to a similar manner to those of the above Example 3-(1) to (8), the following compounds were obtained:

(1) Diethyl 2-methyl-4-(2-nitrophenyl)-6-hydroxyiminomethyl-1,4-dihydropyridine-3,5-dicarboxylate.

(2) Diethyl 2-methyl-4-(2-chloro-5-nitrophenyl)-6-hydroxyiminomethyl-1,4-dihydropyridine-3,5-dicarboxylate.

(3) Diethyl 2-methyl-4-(2-furyl)-6-hydroxyiminomethyl-1,4-dihydropyridine-3,5-dicarboxylate.

(4) 2-ethoxyethyl 2-methyl-4-(3-nitrophenyl)-5-ethoxycarbonyl-6-hydroxyiminomethyl-1,4-dihydropyridine-3-carboxylate.

(5) 2-(N,N-Diethylamino)ethyl 2-methyl-4-(3-nitrophenyl)-5-ethoxycarbonyl-6-hydroxyiminomethyl-1,4-dihydropyridine-3-carboxylate.

(6) Diethyl 2-methyl-4-(3-nitrophenyl)-6-iminomethyl-1,4-dihydropyridine-3,5-dicarboxylate.

Those compounds were prepared from the corresponding 6-formyl compounds in a similar manner to those of Examples 3-(1) to (8) and were identified by converting them to the corresponding 6-cyano compounds

EXAMPLE 4

(1)-(1) A mixture of diethyl 2-methyl-4-(2-chlorophenyl)-6-hydroxyiminomethyl-1,4-dihydropyridine-3,5-dicarboxylate (0.6135 g) and N,N'-dicyclohexyl-carbodiimide (804.6 mg) in pyridine (3 ml) was heated under reflux for 6 hours. The resultant solution was acidified with dilute hydrochloric acid and extracted with ethyl acetate. The insoluble product was filtered off and the filtrate was washed with water, dried over magnesium sulfate and evaporated under reduced pressure. To the residue was added diethyl ether and the mixture was filtered. The filtrate was concentrated under reduced pressure to give red oil (703.7 mg). The oil was purified by column chromatography on silica gel [eluant:benzene(10)+ethyl acetate (1)] and crystalized with n-hexane. The crystals were recrystallized from a mixture of n-hexane and diethyl ether to give yellow crystals (417.1 mg) of diethyl 2-methyl-4-(2-chlorophenyl)-6-cyano-1,4-dihydropyridine-3,5-dicarboxylate, m.p. 136° to 137° C.

(1)-(2) A mixture of diethyl 2-methyl-4-(2-chlorophenyl)-6-formyl-1,4-dihydropyridine-3,5-dicarboxylate (377.8 mg), sodium formate (125 mg) and hydroxylamine hydrochloride (79.93 mg) in formic acid (1.5 ml) was heated under reflux for an hour. Water was added to the reaction mixture and the mixture was extracted with ethyl acetate. The extract was filtered and the filtrate was washed with water, an aqueous sodium bicarbonate solution, water and a saturated aqueous solution of sodium chloride in turn and dried over magnesium sulfate. After the solvent was distilled from the solution, ether was added to the residue. The solution was filtered and the filtrate was concentrated under reduced pressure to give oil (210 mg). The oil was crystallized from a mixture of n-hexane and diethyl ether to give crystals (154.1 mg) of diethyl 2-methyl-4-(2-chlorophenyl)-6-cyano-1,4-dihydropyridine-3,5-dicarboxylate, which was identified with the authentic sample. The insoluble yellow powder (110 mg) which was collected by filtration in the above was the product of ethyl 1-oxo-6-methyl-8-(2-chlorophenyl)-5,8-dihydro-1H-pyrido[2,3-d][1,2]oxazine-7-carboxylate.

I.R. Spectrum (Nujol)
$\nu$(cm$^{-1}$): 3340, 3250, 1730, 1693, 1686 (shoulder), 1670, 1504, 1374, 1235, 1169, 1094, 972, 834, 778, 755

N.M.R. Spectrum ($\delta$: DMSO-d$_6$)
ppm: 0.98 (3H, t, J=7 Hz), 2.37 (3H, s), 3.90 (2H, q, J=7 Hz), 5.35 (1H, s), 7.1 to 7.5 (4H, m), 10.02 (1H, s), 10.35 (1H, s)

(1)-(3) A mixture of diethyl 2-methyl-4-(2-chlorophenyl)-6-formyl-1,4-dihydropyridine-3,5-dicarboxylate (377.8 mg), sodium formate (125 mg), hydroxylamine hydrochloride (79.93 mg) in formic acid (1.5 ml) was stirred at room temperature for 5 minutes and acetic anhydride (0.2 ml) was added to the solution. The mixture was stirred at room temperature for 20 minutes and heated under reflux for an hour. After adding water to the resultant solution, the solution was extracted with ethyl acetate. The extract was washed with an aqueous sodium bicarbonate solution, water and a saturated aqueous sodium chloride solution in turn, dried over magnesium sulfate and concentrated under reduced pressure to give brown oil (0.41 g). The oil was crystallized from a mixture of diethyl ether and n-hexane to give yellow powder (207 mg) of diethyl 2-methyl-4-(2-chlorophenyl)-6-cyano-1,4-dihydropyridine-3,5-dicarboxylate, which was identified with the authentic sample.

(1)-(4) A mixture of diethyl 2-methyl-4-(2-chlorophenyl)-6-formyl-1,4-dihydropyridine-3,5-dicarboxylate (377.8 mg), sodium acetate (164 mg) and hydroxylamine hydrochloride (80 mg) in acetic acid (1.5 ml) was stirred at room temperature for 30 minutes. After acetic anhydride (0.2 ml) was added to the solution, the solution was stirred at room temperature for an hour and then heated under reflux for an hour. Water was added to the reaction mixture, the solution was extracted with diethyl ether. The extract was washed with water, an aqueous sodium bicarbonate solution and water in turn and dried over magnesium sulfate. The solution was concentrated under reduced pressure to give yellow oil (410 mg). The oil was crystallized with n-hexane to give crystals (342.4 mg) of diethyl 2-methyl-4-(2-chlorophenyl)-6-cyano-1,4-dihydropyridine-3,5-dicarboxylate, which was identified with the authentic sample.

(2) A mixture of diethyl 2-methyl-4-(2-nitrophenyl)-6-formyl-1,4-dihydropyridine-3,5-dicarboxylate (2.03 g), hydroxylamine hydrochloride (417 mg), sodium acetate (861.4 mg) in acetic acid (15 ml) was stirred at room temperature for 30 minutes. Acetic anhydride (1 ml) was added to the reaction mixture, and the mixture was stirred at room temperature for 90 minutes and further refluxed for an hour. The acetic acid was distilled off under reduced pressure, and to the resultant residue was added water, and the aqueous mixture was adjusted to pH 7 to 8 with sodium bicarbonate and extracted with diethyl ether. The extract was washed with water, dried over magnesium sulfate and then concentrated under reduced pressure to give an oil. This oil was subjected to column chromatography on silica gel with an eluent [a mixture of 4 parts of benzene and one part of ethyl acetate by volume]. The resultant oily substance (1.7 g) was crystallized by treating with a mixture of diethyl ether and n-hexane. These crystals (1.5 g) were recrystallized from a mixture of diethyl ether and n-hexane to give pure crystals (1.23 g) of diethyl 2-methyl-4-(2-nitrophenyl)-6-cyano-1,4-dihydropyridine-3,5-dicarboxylate, mp 126° to 127.5° C.

(3)-(1) A solution of the powder (0.49 g) of diethyl 2-methyl-4-(2-trifluoromethylphenyl)-6-hydroxylminomethyl-1,4-dihydropyridine-3,5-dicarboxylate and thionyl chloride (1.5 ml) in dry diethyl ether (1.5 ml) was stirred at room temperature for 30 minutes. After the resultant solution was evaporated to dryness, water was added to the residue and the mixture was extracted with ethyl acetate. The extract was washed with water, dried over magnesium sulfate and concentrated under reduced pressure to give a brown oil (0.39 g). The oil was purified by a column chromatography on silica gel with an eluent [benzene (5)+ethyl acetate (1)] and crystallized by treating with n-hexane to give yellow powder (50 mg). The powder was recrystallized from a mixture of diethyl ether and n-hexane to give crystals of diethyl 2-methyl-4-(2-trifluoromethylphenyl)-6-cyano-1,4-dihydropyridine-3,5-dicarboxylate, m.p. 140° to 143° C.

(3)-(2) A mixture of the crystals (1.09 g) of diethyl 2-methyl-4-(2-trifluoromethylphenyl)-6-hydroxyiminomethyl-1,4-dihydropyridine-3,5-dicarboxylate and N,N'-dicyclohexylcarbodimide (1.319 g) in pyridine (5 ml) was heated under reflux for 6.5 hours. After removing pyridine, dilute hydrochloric acid was added to the residue and the mixture was stirred for 10 minutes. The mixture was extracted with ethyl acetate and the insoluble product was filtered off. The filtrate was washed with water, dried over magnesium sulfate and concentrated under reduced pressure to give brown oil (1.09 g). The oil was purified by column chromatography on silica gel with an eluent [benzene (10)+ethyl acetate (1)] to give oil (720 mg). The oil was crystallized by treating with n-hexane and the precipitates were collected by filtration and washed with n-hexane to give yellow powder (610 mg). The powder was recrystallized from a mixture of ether and n-hexane to give pure diethyl 2-methyl-4-(2-trifluoromethylphenyl)-6- cyano-1,4-dihydropyridine-3,5-dicarboxylate, which was identified with the authentic sample, m.p. 140° to 143° C.

(3)-(3) A mixture of diethyl 2-methyl-4-(2-trifluoromethylphenyl)-6-formyl-1,4-dihydropyridine-3,5-dicarboxylate (205.7 mg), sodium acetate (82 mg) and hydroxylamine hydrochloride (40 mg) in acetic acid (1.5 ml) was stirred at room temperature for 30 minutes. After acetic anhydride (0.1 ml) was added, the solution was stirred at room temperature for 1.5 hours and then heated under reflux for an hour. To the resultant solution was added water and the solution was extracted with diethyl ether. The extract was washed with water, an aqueous sodium bicarbonate solution and water in turn, dried over magnesium sulfate and concentrated under reduced pressure to give oil (201 mg). The oil was purified by column chromatography on silica gel with an eluent [benzene (5)+ethyl acetate (1)] to give pure oil (172.4 mg). The oil was crystallized by treating with n-hexane to give powder (118 mg) of diethyl 2-methyl-4-(2-trifluoromethylphenyl)-6-cyano-1,4-dihydropyridine-3,5-dicarboxylate.

(4) A mixture of diethyl 2-methyl-4-(2-chloro-5-nitrophenyl)-6-formyl-1,4-dihydropyridine-3,5-dicarboxylate (3.70 g), hydroxylamine hydrochloride (695 mg), sodium acetate (1.436 g) in acetic acid (36 ml) was stirred at room temperature for 2.5 hours, and then acetic anhydride (2 ml) was added thereto. The resultant mixture was stirred for 30 minutes and refluxed for 1.5 hours. After removal of the acetic acid, water and ethyl acetate were added to the reaction mixture and the resultant mixture was washed twice with dilute sodium bicarbonate aqueous solution and then with an aqueous sodium chloride, and dried over magnesium sulfate. After removal of the solvent the residue was washed with diethyl ether to give powder (2.5 g). The powder was subjected to column chromatography on silica-gel with an eluent (a mixture of 10 parts of benzene and one part of ethyl acetate by volume). The fraction of the eluate which showed only one spot on thin-layer chromatography was concentrated to give crude crystals (450 mg) and the fraction of the eluate which showed plural spots on thin-layer chromatography was also concentrated to give crude crystals (1.0 g). Thus obtained crude crystals were combined together and recrystallized from a mixture of benzene and ethyl acetate to give pure crystals (657 mg) of diethyl 2-methyl-4-(2-chloro-5-nitrophenyl)-6-cyano-1,4-dihydropyridine-3,5-dicarboxylate, m.p. 204.5° to 205.5° C.

(5) A mixture of diethyl 2-methyl-4-(2-furyl)-6-formyl-1,4-dihydropyridine-3,5-dicarboxylate (1.6 g), hydroxylamine hydrochloride (383.6 mg) and sodium acetate (787.6 mg) in acetic acid (14 ml) was stirred for 30 minutes at room temperature. To the mixture, acetic anhydride (1 ml) was added and stirred for 1.5 hours at room temperature and further stirred for an hour under reflux. After removal of the acetic acid from the reaction mixture, water was added to the residue and the mixture was extracted with ethyl acetate. The extract was washed with saturated sodium bicarbonate solution and water and dried, and then the solvent was distilled off under reduced pressure. The resultant brown oil (1.8 g) was purified by column chromatography on silica gel by an eluent (a mixture of 15 parts of chloroform and one part of ethyl acetate by volume). The concentrate (920 mg) of the fraction of the eluate which showed one spot on thin-layer chromatography and the concentrate of one (450 mg) which showed plural spots respectively gave crystals (totally 875 mg) and these were recrystallized from a mixture of diethyl ether and n-hexane to give pure crystals (818 mg) of diethyl 2-methyl-4-(2-furyl)-6-cyano-1,4-dihydropyridine-3,5-dicarboxylate, m.p. 139° to 141° C.

(6)-(1) A mixture of 2-(N-benzyl-N-methylamino)ethyl 2-methyl-4-(3-nitrophenyl)-5-ethoxycarbonyl-6-hydroxyimino-methyl-1,4-dihydropyridine-3-carboxylate (0.91 g) and N,N'-dicyclohexylcarbodiimide (0.987 g) in pyridine (5 ml) was heated under reflux for 3 hours. After removal of the pyridine under reduced pressure, water was added to the residue. The mixture was extracted with ethyl acetate. The insoluble product was filtered off and the filtrate was washed with water, dried over magnesium sulfate and concentrated under reduced pressure to give red oil (1.6 g). The oil was purified by column chromatography on silica gel with an eluent [benzene (2)+ethyl acetate (1)] to give a reddish oil (0.68 g) of 2-(N-benzyl-N-methylamino)ethyl 2-methyl-4-(3-nitrophenyl)-5-ethoxycarbonyl-6-cyano-1,4-dihydropyridine-3-carboxylate.

I.R. Spectrum (Nujol)
$\nu$(cm$^{-1}$) : 3320, 3250 (shoulder), 2240, 1708, 1685, 1525, 1500, 1345, 1293, 1210, 1100, 1030, 780, 735, 700

N.M.R. Spectrum ($\delta$: CDCl$_3$)
ppm: 1.25 (3H, t, J=7 Hz), 2.15 (3H, s), 2.39 (3H, s), 2.62 (2H, t, J=7 Hz), 3.48 (2H, s), 3.9 to 4.3 (4H, q (CH$_2$CH$_3$), t (COOCH$_2$CH$_2$N)), 5.26 (1H, s), 7.1 to 8.2 (10H, m)

The product obtained above was dissolved in diethyl ether. After adding ethanolic hydrochloric acid to the solution, the solution was evaporated to dryness. The residue was pulverized with n-hexane and the precipitating powder was collected by filtration. The powder was recrystallized from an aqueous ethanol to give yellow pure crystals (460.8 mg) of the object compound hydrochloride, m.p. 228° to 229° C.

(6)-(2) A mixture of 2-(N-benzyl-N-methylamino)ethyl 2-methyl-4-(3-nitrophenyl)-5-ethoxycarbonyl-6-formyl-1,4-dihydropyridine-3-carboxylate (253.8 mg), sodium acetate (82 mg) and hydroxylamine hydrochloride (40 mg) in acetic acid (1 ml) was stirred at room temperature for 30 minutes. After acetic anhydride (0.1 ml) was added, the solution was stirred at room temperature for an hour and then heated under reflux for an hour. Water was added to the reaction mixture and the solution was neutralized with sodium bicarbonate and then extracted with ethyl acetate. The extract was washed with an aqueous sodium bicarbonate solution and water in turn, dried over magnesium sulfate and then concentrated under reduced pressure to give an oil (250 mg) (quantitatively) of 2-(N-benzyl-N-methylamino)-ethyl 2-methyl-4-(3-nitrophenyl)-5-ethoxycarbonyl-6-cyano-1,4-dihydropyridine-3-carboxylate, which was identified with the authentic sample.

(7) Starting from a mixture of an oil (1.66 g) of 2-(N,N-diethylamino)ethyl 2-methyl-4-(3-nitrophenyl)-5-ethoxycarbonyl-6-formyl-1,4-dihydropyridine-3-carboxylate, hydroxylamine hydrochloride (0.302 g) and sodium acetate (0.593 g) in acetic acid (12 ml) and acetic anhydride (1.8 ml) was obtained crystals (700 mg) according to a similar manner to that of Example (4)-(2). These crystals were recrystallized from ethanol to give pure crystals (420 mg) of 2-(N,N-diethylamino)ethyl 2-methyl-4-(3-nitrophenyl)-5-ethoxycarbonyl-6-cyano-1,4-dihydropyridine-3-carboxylate, m.p. 150° to 152° C.

(8) A mixture of 2-ethoxyethyl 2-methyl-4-(3-nitrophenyl)-5-ethoxycarbonyl-6-formyl-1,4-dihydropyridine-3-carboxylate (3.00 g), hydroxylamine hydrochloride (0.5547 g), sodium acetate (1.1382 g) in acetic acid (10 ml) was stirred for 30 minutes at room temperature. To this mixture was added acetic anhydride (1.4 ml) and the resultant mixture was stirred for an hour at room temperature and refluxed for an hour. The acetic acid was distilled off under reduced pressure, and to the residue was added water. The resultant mixture was neutralized with an aqueous solution of sodium bicarbonate and extracted with ethyl acetate twice. The extract was washed with water and an aqueous solution saturated with sodium chloride and dried. The solvent was distilled off and thus obtained viscous oily substance (3.19 g) was subjected to column chromatography on silica gel with an eluent [a mixture of 5 parts of benzene and one part of ethyl acetate by volume] and a yellow oil (1.74 g) was obtained from the fraction which contained the designated product. The oil turned into crystals (1.56 g). These crystals were recrystallized from benzene to give yellow powder (1.5 g) of 2-ethoxyethyl 2-methyl-4-(3-nitrophenyl)-5-ethoxycarbonyl-6-cyano-1,4-dihydropyridine-3-carboxylate.½ benzene, m.p. 89° to 91° C. Thus obtained yellow powder was further recrystallized from a mixture of diethyl ether and n-hexane to give crystals of 2-ethoxyethyl 2-methyl-4-(3-nitrophenyl)-5-ethoxycarbonyl-6-cyano-1,4-dihydropyridine-3-carboxylate, m.p. 115° to 116° C.

(9) A mixture of diethyl 2-methyl-4-(3-nitrophenyl)-6-formyl-1,4-dihydropridine-3,5-dicarboxylate (1.9418 g), hydroxylamine hydrochloride (399.6 mg), sodium acetate (820 mg) in acetic acid (7.5 ml) was stirred at room temperature for 30 minutes. After addition of acetic anhydride (1 ml), the resultant mixture was stirred for an hour at room temperature and further refluxed for an hour. The acetic acid was distilled off, and water was added to the residue. The resultant aqueous mixture was neutralized by an aqueous solution saturated with sodium bicarbonate. A precipitating oily substance was extracted with ethyl acetate twice. The extract was washed with an aqueous solution of sodium chloride and dried. The solvent was distilled off under reduced pressure to give a orange-yellow oil (2.0103 g). This oil turned into crystals and these crystals were recrystallized from a mixture of diethyl ether, ethyl acetate and n-hexane to give yellow powder (0.9119 g). This powder was dissolved into a mixture of 5 parts of benzene and one part of ethyl acetate by volume and filtered on silica gel to give crystals (1.02 g). These crystals were recrystallized from a mixture of benzene and diethyl ether to give yellow granules (0.8479 g) of diethyl 2-methyl-4-(3-nitrophenyl)-6-cyano-1,4-dihydropyridine-3,5-dicarboxylate, m.p. 174° to 177° C.

(10) Starting from a mixture of a reddish oil (2.0 g) of 2-benzyloxyethyl 2-methyl-4-(2-nitrophenyl)-5-ethoxycarbonyl-6-formyl-1,4-dihydropyridine-3-carboxylate, hydroxylamine hydrochloride (336.9 mg), sodium acetate (662.9 mg) in acetic acid (15 ml) and acetic anhydride (1.5 ml) was obtained crystals (767 mg) according to a similar manner to that of Example 4-2). These crystals were recrystallized from a mixture of benzene and diethyl ether to give faint yellow crystals (450 mg) of 2-benzyloxyethyl 2-methyl-4-(2-nitrophenyl)-5-ethoxycarbonyl-6-cyano-1,4-dihydropyridine-3-carboxylate, m.p. 139° to 140° C. (further recrystallized from a mixture of diethyl ether and n-hexane).

(11) Starting from a mixture of 2-phenoxyethyl 2-methyl-4-(2-nitrophenyl)-5-ethoxycarbonyl-6-formyl-1,4-dihydropyridine-3-carboxylate (1.03 g), hydroxylamine hydrochloride (178.6 mg) and sodium acetate (352 mg) in acetic acid (8 ml) and acetic anhydride (1 ml), there was obtained in a similar manner to that of Example 4-2) an oil (420 mg) of 2-phenoxyethyl 2-methyl-4-(2-nitrophenyl)-5-ethoxycarbonyl-6-cyano-1,4-dihydropyridine-3-carboxylate.

I.R. Spectrum (KBr)
$\nu(cm^{-1})$: 3330, 2250, 1710, 1600, 1530, 1500, 1300, 1216, 1110, 757

N.M.R. Spectrum ($\delta$, CDCl$_3$)
ppm: 1.2 (3H, t, J=7 Hz), 2.36 (3H, s), 4 to 4.4 (6H, m), 6.05 (1H, s), 6.73 (1H, m), 6.83 to 7.66 (9H, m)

(12) Starting from a mixture of 2-ethoxyethyl 2-methyl-4-(2-nitrophenyl)-5-ethoxycarbonyl-6-formyl-1,4-dihydropyridine-3-carboxylate (900 mg), hydroxylamine hydrochloride (167 mg) and sodium acetate (341 mg) in acetic acid (7 ml) and acetic anhydride (1 ml) was obtained by applying an essentially similar manner to that of Example 4-2), crystals (420 mg) of 2-ethoxyethyl 2-methyl-4-(2-nitrophenyl)-5-ethoxycarbonyl-6-cyano-1,4-dihydropyridine-3-carboxylate, m.p. 129° to 130.5° C. (recrystallized from a mixture of diethyl ether and n-hexane).

(13) Starting from a mixture of diethyl 2-methyl-4-(2-nitrophenyl)-6-formylmethyl-1,4-dihydropyridine-3,5-dicarboxylate, hydroxylamine hydrochloride and sodium acetate in acetic acid and acetic anhydride, was obtained an oil of diethyl 2-methyl-4-(2-nitrophenyl)-6-cyanomethyl-1,4-dihydropyridine-3,5-dicarboxylate, by applying an essentially similar manner to that of Example 4-2).

I.R. Spectrum (Liquid)
$\nu(cm^{-1})$: 2210

N.M.R. Spectrum ($\delta$, CDCl$_3$)
ppm: 1.17 (6H, t, J=7 Hz), 2.32 (3H, s), 3.9 to 4.3 (4H, m), 4.78 (2H, s), 5.89 (1H, s), 7.14 (1H, broad s) 7.2 to 7.85 (4H, m)

EXAMPLE 5

(1) To a solution of diethyl 2,6-diformyl-4-(2-chlorophenyl)-1,4-dihydropyridine-3,5-dicarboxylate (272.7 mg) in 99% ethanol (7 ml) was added sodium borohydride (52.7 mg) under stirring at about 5° C. and the resultant mixture was further stirred at 5° C. for 10 minutes. The resultant solution was neutralized with dilute hydrochloric acid and ethanol was removed at room temperature under reduced pressure. To the residue was added water and the precipitates were collected by filtration, and then dried to give crude pale yellow crystals (261.0 mg) of diethyl 2,6-dihydroxymethyl-4-(2-chlorophenyl)-1,4-dihydropyridine-3,5-dicarboxylate. The crude crystals were recrystallized from a mixture of ethanol and diethyl ether to give pure pale yellow needles, m.p. 190° to 191° C.

(2) To a solution of diethyl 2-methyl-4-(2-chlorophenyl)-6-formyl-1,4-dihydropyridine-3,5-dicarboxylate (1.5 g) in ethanol (30 ml) was added sodium borohydride (155 mg) under stirring and this mixture was further stirred at room temperature for 2 hours. The resultant mixture was acidified with dilute hydrochloric acid and the solvent was removed. Water was added to the residue and the mixture was extracted twice with ethyl acetate. After the extract was washed with water and dried, the solvent was removed under reduced pressure from the extract to give a red oil (1.3525 g). The oil was dissolved in diethyl ether and allowed to stand at room temperature. After the insoluble product was removed by filtration, the filtrate was allowed to stand. The slowly precipitated crystals were collected by filtration and recrystallized from a mixture of diethyl ether and n-hexane to give pure crystals (92.0 mg) of diethyl 2-methyl-4-(2-chlorophenyl)-6-hydroxymethyl-1,4-dihydropyridine-3,5-dicarboxylate, m.p. 143° C. The insoluble product obtained above was collected by filtration and recrystallized from ethyl acetate to give colorless prisms (241.5 mg) of ethyl 2-methyl-4-(2-chlorophenyl)-5-oxo-1,4,5,7-tetrahydrofuro-[3,4-b]pyridine-3-carboxylate, m.p. 211° to 212° C.

(3) To a mixture of dimethyl 2-methyl-4-(2-chlorophenyl)-6-acetyl-1,4-dihydropyridine-3,5-dicarboxylate (450 mg) in methanol (15 ml) was added gradually sodium borohydride (46.8 mg) under ice-cooling with stirring. The mixture was further stirred for 35 minutes under ice-cooling. The solution was neutralized with 2N-hydrochloric acid under ice-cooling and the solvent was distilled off under reduced pressure at a lower temperature than 30° C. on a water-bath. To the residue was added water and a small amount of an aqueous sodium bicarbonate to adjust the medium to pH 7 to 8. The resultant mixture was allowed to stand to give white powder, which was collected by filtration and dried to give powder (395.0 mg). To this powder was added diethyl ether (20 ml) and the mixture was stirred for about 30 minutes at room temperature. Insoluble white powder was collected by filtration and washed with diethyl ether. The filtrate and the washings were combined together and the solvent was distilled off at relatively low temperature to give crude crystals (100.5 g) of dimethyl 2-methyl-4-(2-chlorophenyl)-6-(1-hydroxyethyl)-1,4-dihydropyridine-3,5-dicarboxylate, m.p. 145° to 147° C.

The insoluble white powder obtained above was collected by filtration and washed with diethyl ether to give crude white powder (264.2 mg) of methyl 2-methyl-4-(2-chlorophenyl)-5-oxo-7-methyl-1,4,5,7-tetrahydrofuro[3,4-b]pyridine-3-carboxylate, m.p. 228° to 233° C.

(4) To a solution of diethyl 2-methyl-4-(2-nitrophenyl)-6-formyl-1,4-dihydropyridine-3,5-dicarboxylate (2.0881 g) in ethanol (20 ml) was gradually added sodium borohydride (0.1892 g) under stirring and the resultant mixture was further stirred at room temperature for an hour. The solution was acidified with dilute hydrochloric acid and stirred at room temperature for 30 minutes. After the resultant solution was filtered, the filtrate was concentrated under reduced pressure and extracted with ethyl acetate. The extract was washed with water and dried and then the solvent was removed to give orange oil (1.8596 g) of diethyl 2-methyl-4-(2-nitrophenyl)-6-hydroxymethyl-1,4-dihydropyridine-3,5-dicarboxylate. After the crude, product was dissolved in ethanol, the solution was filtered. The filtrate was concentrated under reduced pressure and the oily residue was allowed to stand for 3 days. Thus obtained crystals were recrystallized from ether to give pure product, m.p. 112° to 113° C.

The insoluble product obtained by filtration of the resultant solution in the above was recrystallized from ethanol to give pale yellow flakes (455.1 mg) of ethyl 2-methyl-4-(2-nitrophenyl)-5-oxo-1,4,5,7-tetrahydrofuro[3,4-b]pyridine-3-carboxylate, m.p. 220° to 222° C. The product was further recrystallized from ethyl acetate to give pure product, m.p. 221° to 223° C.

(5) To a suspended solution of diethyl 2-methyl-4-(3-nitrophenyl)-6-formyl-1,4-dihydropyridine-3,5-dicarboxylate (233 mg) in ethanol (10 ml) was added sodium borohydride (22.7 mg) at 0° to 5° C. under stirring and this mixture was further stirred at about 5° C. for an hour and 10 minutes. After the reaction, the mixture was adjusted to pH 4 to 5 with 0.1 N-hydrochloric acid, and then the solvent was removed under reduced pressure. The residue was extracted with ethyl acetate and the extract was washed with water and dried over magnesium sulfate. The extract was concentrated under reduced pressure and the residue was crystallized by treating with a mixture of diethyl ether and n-hexane. The precipitated crystals were collected by filtration, dried and recrystallized from a mixture of diethyl ether and n-hexane to give crystals of diethyl 2-methyl-4-(3-nitrophenyl)-6-hydroxymethyl-1,4-dihydropyridine-3,5-dicarboxylate (152 mg), m.p. 141° to 142.5° C.

(6) To a solution of diethyl 2-methyl-4-(2-trifluoromethylphenyl)-6-formyl-1,4-dihydropyridine-3,5-dicarboxylate (1.0 g) in ethanol (20 ml) was gradually added sodium borohydride (92 mg) under stirring and ice-cooling and the resultant mixture was further stirred for 25 minutes. The resultant mixture was adjusted with 0.1 N hydrochloric acid to pH 4 to 5. The ethanol was removed under reduced pressure without heating so much, and water was added to the residue to give crystals. The crystals were collected by filtration to give crude crystals (1.2 g). These were recrystallized from a mixture of diethyl ether and n-hexane to give pure crystals of diethyl 2-methyl-4-(2-trifluoromethylphenyl)-6-hydroxymethyl-1,4-dihydropyridine-3,5-dicarboxylate, m.p. 147° to 148.5° C.

(7) To a solution of diethyl 2-methyl-4-(2-methoxyphenyl)-6-formyl-1,4-dihydropyridine-3,5-dicarboxylate (1.1320 g) in ethanol (30 ml) was gradually added sodium borohydride (114 mg) under stirring and the resultant mixture was further stirred at room temperature for an hour. The resultant mixture was acidified with dilute hydrochloric acid. After removing ethanol from the mixture, water was added to the residue to solidify. The solid was collected by filtration, dried and washed with diethyl ether. The diethyl ether washings were concentrated to the volume of about 10 ml and stood at room temperature to give pale yellowish granules (372.5 mg) of diethyl 2-methyl-4-(2-methoxyphenyl)-6-hydroxymethyl-1,4-dihydropyridine-3,5-dicarboxylate, m.p. 125° to 126° C. On the other hand, the solid obtained above, which was collected by filtration and washed with diethyl ether, was added to a mixed solution of p-toluenesulfonic acid (catalytic amount) in ethanol (5 ml) and the mixture was refluxed for one hour. After removal of ethanol, the residue was pulverized with diethyl ether and collected by filtration. The powder was recrystallized from a mixture of acetone and ethyl acetate to give colorless granules (114.8 mg) of ethyl 2-methyl-4-(2-methoxyphenyl)-5-oxo-1,4,5,7-tetrahydrofuro[3,4-b]-pyridine-3-carboxylate, m.p. 219° to 220° C.

(8) To a suspension of diethyl 2-methyl-4-(3-hydroxyphenyl)-6-formyl-1,4-dihydropyridine-3,5-dicarboxylate (600 mg) in ethanol (15 ml), was added sodium borohydride (63.5 mg) at 0° C. under stirring and the resultant mixture was further stirred for an hour. The resultant mixture was adjusted with 0.1 N hydrochloric acid to pH 3 to 4 under ice-cooling. The ethanol was distilled off under reduced pressure and the residue was extracted with ethyl acetate. The extract was washed with water twice and an aqueous sodium chloride solution in turn, dried over magnesium sulfate and then concentrated under reduced pressure to give crystals (600 mg). These were recrystallized from a mixture of ethyl acetate and diethyl ether to give pure crystals (350 mg) of diethyl 2-methyl-4-(3-hydroxyphenyl)-6-hydroxymethyl-1,4-dihydropyridine-3,5-dicarboxylate, m.p. 161.5° to 163° C.

(9) To a solution of diethyl 2-methyl-4-(2-thienyl)-6-formyl-1,4-dihydropyridine-3,5-dicarboxylate (940.68 mg) in 99% ethanol (30 ml) was gradually added sodium borohydride (113.5 mg) under stirring and this was further stirred at room temperature for 2 hours. After removal of ethanol, the residue was extracted with ethyl acetate and the extract was washed twice with water and then dried. The solvent was removed from the extract to give a pale yellow oil. The oil was pulverized with n-hexane. The powder was dissolved in ethyl acetate. After collecting by filtration of the insoluble product, to the filtrate was added n-hexane and the mixture was allowed to stand in refrigerator. The appearring crystals were collected by filtration to give pale yellow granules (857.2 mg) of diethyl 2-methyl-4-(2-thienyl)-6-hydroxymethyl-1,4-dihydropyridine-3,5-dicarboxylate, m.p. 125° to 126° C.

The insoluble product obtained above was collected by filtration to give powder (33.3 mg) of ethyl 2-methyl-4-(2-thienyl)-5-oxo-1,4,5,7-tetrahydrofuro[3,4-b]pyridine-3-carboxylate, m.p. 232° C.

(10) To a solution of 2-hydroxyethyl 2-methyl-4-(2-nitrophenyl)-5-ethoxycarbonyl-6-formyl-1,4-dihydropyridine-3-carboxylate (2.0 g) in ethanol (40 ml) was added bit-by-bit sodium borohydride (113.5 mg) at 5° C. under stirring. The mixture was further stirred at 5° C. for 30 minutes and acidified weakly with 50% acetic acid. After removal of the ethanol, to the residue was added water, and the mixture was made slightly alkaline with an aqueous solution of sodium bicarbonate, allowed to stand and then filtered, when it became clear. The precipitate (1.58 g) was collected by filtration and recrystallized from a mixture of ethanol and diisopropyl ether to give yellowish-orange granules (0.99 g) of 2-hydroxyethyl 2-methyl-4-(2-nitrophenyl)-5-ethoxycarbonyl-6-hydroxymethyl-1,4-dihydropyridine-3-carboxylate, m.p. 167° to 169° C.

(11) To a suspended solution of benzyl 2-methyl-4-(2-nitrophenyl)-5-ethoxycarbonyl-6-formyl-1,4-dihydropyridine-3-carboxylate (1.2 g) in ethanol (20 ml) was added sodium borohydride (60.6 mg) under ice-cooling and stirred, and further stirred for an hour at 0° C. and another an hour at 3° C. The reaction mixture was added with water and the resultant mixture was adjusted to pH 6 to 7 with 2 N hydrochloric acid, and the solvent was distilled off. The residue was extracted with ethyl acetate and washed with water and dried. After removal of the solvent, the resultant oil (1.3 g) was purified by column chromatography on silica gel with an eluent (a mixture of ten parts of benzene and one part of ethyl acetate by volume) to give an oil which was immediately crystallized. The resultant crystals were recrystallized from a mixture of diethyl ether and n-hexane and dissolved in benzene. The benzene solution was subjected to azeotropic process five times to give pure crystals of benzyl 2-methyl-4-(2-nitrophenyl)-5-ethoxycarbonyl-6-hydroxymethyl-1,4-dihydropyridine-3-carboxylate, m.p. 51° to 57° C.

(12) To a suspension of 2-ethoxyethyl 2-methyl-4-(3-nitrophenyl)-5-ethoxycarbonyl-6-formyl-1,4-dihydropyridine-3-carboxylate (1.13 g) in ethanol (15 ml) was added sodium borohydride (80 mg) with stirring under ice-cooling, and this mixture was further stirred for an hour at the same temperature. The reaction mixture was adjusted with dilute hydrochloric acid to pH 6 under ice-cooling and then the solvent was distilled off. To the residue was added water and the aqueous mixture was extracted with diethyl ether. The extract was washed with water and dried over magnesium sulfate. Removal of the solvent gave an oil, which was crystallized by treating with n-hexane. These were recrystallized from a mixture of diethyl ether and n-hexane to give pure crystals (900 mg) of 2-ethoxyethyl 2-methyl-4-(3-nitrophenyl)-5-ethoxycarbonyl-6-hydroxymethyl-1,4-dihydropyridine-3-carboxylate, m.p. 99° to 100° C.

(13) To a solution of 2-(N-methyl-N-benzylamino)ethyl 2-methyl-4-(3-nitrophenyl)-5-ethoxycarbonyl-6-formyl-1,4-dihydropyridine-3-carboxylate (1.5 g) in ethanol (15 ml) was added sodium borohydride (112 mg) under stirring and ice-cooling, and this mixture was further stirred for 20 minutes at the same temperature. The reaction mixture was adjusted with 0.1 N hydrochloric acid to pH 6 to 7 under ice-cooling, and concentrated under reduced pressure. To the residue was added ethyl acetate and water, and the aqueous layer was further washed with ethyl acetate twice. The extract obtained above and the washings were put together, washed with water, dried over magnesium sulfate, and concentrated under reduced pressure to give an oil (1.48 g) of 2-(N-methyl-N-benzylamino)ethyl 2-methyl-4-(3-nitrophenyl)-5-ethoxycarbonyl-6-hydroxymethyl-1,4-dihydropyridine-3-carboxylate.

I.R. Spectrum (film)
$\nu$(cm$^{-1}$): 3390, 1730, 1680, 1650, 1600, 1520, 1460, 1345, 1200, 1100, 1025, 900, 780, 740, 700

N.M.R. Spectrum ($\delta$: CDCl$_3$+D$_2$O)
ppm: 1.2 (3H, t, J=7 Hz), 2.2 (3H, s), 2.38 (3H, s), 2.66 (2H, t, J=6 Hz), 3.53 (2H, s), 3.97 to 4.26 (4H, m), 5.14 (1H, s), 7.28 to 8.15 (10H, m)

Thus obtained oil was dissolved into diethyl ether, and 21% ethanolic hydrochloric acid (225 mg) was added to the solution. A precipitating oil substance was washed with diethyl ether several times by decantation and pulverized to give powder (540 mg) of 2-(N-methyl-N-benzylamino)ethyl 2-methyl-4-(3-nitrophenyl)-5-ethoxycarbonyl-6-hydroxymethyl-1,4-dihydropyridine-3-carboxylate hydrochloride which began to decompose at 89° C. with turning to brown.

I.R. Spectrum (Nujol)
$\nu$(cm$^{-1}$): 3300, 2600, 1680, 1525, 1375, 1350, 1200, 1095, 740, 700

(14) To a mixture of powder (329 mg) of methyl 4-(2-chlorophenyl)-5-ethoxycarbonyl-6-formyl-1,4-dihydropyridine-3-carboxylate in ethanol (10 ml) was added sodium borohydride (25.11 mg) under ice-cooling. After further stirring for 50 minutes, the mixture was adjusted to pH 4 to 5 with dilute hydrochloric acid. After removal of the ethanol, water was added to the residue, which was extracted with ethyl acetate. The ethyl acetate layer was washed with water and dried and the residual crystals (about 280 mg) were dissolved in a mixture of diethyl ether and n-hexane and kept in a refrigerator to give pure crystals (184 mg) of methyl 4-(2-chlorophenyl)-5-ethoxycarbonyl-6-hydroxymethyl-1,4-dihydropyridine-3-carboxylate, m.p. 187° to 188° C.

(15) To a solution of diethyl 2-methyl-4-(2-nitrophenyl)-6-[2-N,N-diethylamino)ethyl]iminomethyl-1,4- dihydropyridine-3,5-dicarboxylate (1.1 g) in 99% ethanol (20 ml) was added sodium borohyride (115 mg) under stirring and the mixture was further stirred at room temperature for 5 hours. The resultant mixture was acidified with dilute hydrochloric acid. After removing ethanol, water was added to the residue and the mixture was washed with diethyl ether. The aqueous layer was basified with an aqueous solution of sodium bicarbonate and extracted with ethyl acetate. The extract was washed with water and dried. The solvent was removed from the extract to give greenish brown oil (0.8087 g) of a mixture including diethyl 2-methyl-4-(2-nitrophenyl)-6-[2-(N,N-diethylamino)ethyl-]aminomethyl-1,4-dihydropyridine-3,5-dicarboxylate (one part) and ethyl 2-methyl-4-(2-nitrophenyl)-5-oxo-6-[2-(N,N-diethylamino)ethyl]1,4,5,7-tetrahydropyrrolo[3,4-b]pyridine-3-carboxylate (one part). After dissolving the mixture in ethanol, the solution was refluxed for 5 hours. The removal of the solvent gave crystals. These were recrystallized from ethanol to give yellow needles (729.9 mg) of ethyl 2-methyl-4-(2-nitrophenyl)-5-oxo-6-[2-(N,N-diethylamino)ethyl]-1,4,5,7-tetrahydropyrrolo-[3,4-b]pyridine-3-carboxylate, m.p. 187° to 188° C.

(16) To a solution of diethyl 2-methyl-4-(2-nitrophenyl)-6-(2-hydroxyethyl)iminomethyl-1,4-dihydropyridine-3,5-dicarboxylate (1.2 g) in 96% ethanol (15 ml) was added sodium borohydride (115 mg) and stirred overnight at room temperature. The resultant mixture was weakly acidified with dilute hydrochloric acid and the ethanol was removed from the mixture. The residue was basified with an aqueous solution of sodium bicarbonate and then extracted with ethyl acetate. The extract was washed with water and dried over magnesium sulfate. The solvent was distilled off to give an oil of diethyl 2-methyl-4-(2-nitrophenyl)-6-(2-hydroxyethyl)-aminomethyl-1,4-dihydropyridine-3,5-dicarboxylate. This oil was dissolved in 95% ethanol (15 ml) and the solution was refluxed for 3 hours. Ethanol was removed from the solution to give a red oil. The oil was pulverized and recrystallized from a mixture of ethanol and diethyl ether to give an orange crystals (0.5998 g) of ethyl 2-methyl-4-(2-nitrophenyl)-5-oxo-6-(2-hydroxyethyl)-1,4,5,7-tetrahydropyrrolo-[3,4-b]pyridine-3-carboxylate. The product was further recrystallized from a mixture of ethanol and diethyl ether to give pure pale orange granules, m.p. 210° to 211° C.

EXAMPLE 6

(1) To a solution of diethyl 2-methyl-4-(2-chlorophenyl)-6-hydroxymethyl-1,4-dihydropyridine-3,5-dicarboxylate (759.7 mg) in dried pyridine was dropwise added a solution of acetyl chloride (313.5 mg) in methylene chloride under cooling and stirring. The mixture was stirred overnight at room temperature. After removing the solvent, water was added to the residue, and the mixture was weakly acidified with dilute hydrochloric acid, and then extracted with diethyl ether. The extract was washed with an aqueous saturated sodium chloride solution and water in turn, and dried. The solvent was removed from the extract to give viscous oil (0.99 g). The oil was allowed to stand to pulverize and the crystals were washed with n-hexane and collected by filtration to give crude product (0.6931 g) of diethyl 2-methyl-4-(2-chlorophenyl)-6-acetoxymethyl-1,4-dihydropyridine-3,5-dicarboxylate. The crude product was recrystallized from a mixture of diethyl ether and n-hexane to give the pure product, m.p. 98° C.

(2) A mixed solution of diethyl 2-methyl-4-(2-chlorophenyl)-6-hydroxymethyl-1,4-dihydropyridine-3,5-dicarboxylate (0.3798 g), pyridine (0.791 g) and succinic anhydride (0.1501 g) in dioxane (5 ml) was refluxed for 4.5 hours. The resultant solution was concentrated, acidified with dilute hydrochloric acid and extracted with diethyl ether. The extract was washed with dilute hydrochloric acid and water in turn. The diethyl ether extract was back-extracted with an aqueous saturated sodium bicarbonate solution and the aqueous solution was washed with diethyl ether. The aqueous solution was acidified with dilute hydrochloric acid to precipitate crystals. The crystals were collected by filtration, washed with water and then dried to give diethyl 2-methyl-4-(2-chlorophenyl)-6-(3-carboxypropionyl)oxymethyl-1,4-dihydropyridine-3,5-dicarboxylate (419.3 mg), m.p. 130° to 131° C.

(3) To a solution of diethyl 2-methyl-4-(2-chlorophenyl)-6-hydroxymethyl-1,4-dihydropyridine-3,5-dicarboxylate (0.7050 g) in pyridine (15 ml) was dropwise added a solution of ethyl 5-chloroformylpentanoate (0.7706 g) in methylene chloride under ice-cooling and the mixture was stirred at room temperature for 2.5 hours. After removing the pyridine water was added to residue and the mixture was extracted twice with ethyl acetate. The extract was washed with dilute hydrochloric acid, an aqueous sodium bicarbonate solution and water in turn, and then dried. The solvent was removed from the extract to give a yellow oil (1.0996 g) The oil was pulverized and recrystallized from a mixed solution of diethyl ether and n-hexane to give colorless flakes (0.7311 g) of diethyl 2-methyl-4-(2-chlorophenyl)-6-(5-ethoxycarbonylvaleryl)oxymethyl-1,4-dihydropyridine-3,5-dicarboxylate, m.p. 91° to 92° C.

(4) To a mixture of sodium 3-(N-methyl-N-benzylamino)propionate (2.0 g) in diethyl ether (40 ml) was added thionyl chloride (10 ml) with stirring under ice-cooling. The resultant mixture was stirred at room temperature for 3 hours, heated under reflux for 2 hours and concentrated under reduced pressure to give a solid containing 3-(N-methyl-N-benzylamino)propionyl chloride. A suspension of thus obtained solid in methylene chloride (5 ml) was added to a solution of diethyl 2-methyl-4-(2-chlorophenyl)-6-hydroxymethyl-1,4-dihydropyridine-3,5-dicarboxylate (0.76 g) in pyridine (5 ml) with stirring under ice-cooling. The mixture was stirred for an hour under ice-cooling and concentrated under reduced pressure, and water was added to the residue. The aqueous mixture was extracted with ethyl acetate and the extract was washed with water, dried and concentrated under reduced pressure to give a brown oil (1.55 g). The oil was subjected to column chromatography on silica gel with an eluent [a mixture of 2 parts of benzene and one part of ethyl acetate by volume] to give an oily substance. The oily substance was allowed to stand overnight to give crystals. These crystals were washed with n-hexane and recrystallized from a mixture of diethyl ether and n-hexane to give pure crystals of diethyl 2-methyl-4-(2-chlorophenyl)-6-(3-(N-methyl-N-benzylamino)propionyloxy)methyl-1,4-dihydropyridine-3,5-dicarboxylate, m.p. 86° to 87° C.

(5) To a mixture of diethyl 2-methyl-4-(2-nitrophenyl)-6-hydroxymethyl-1,4-dihydropyridine-3,5-dicarboxylate (2.35 g) in pyridine (30 ml), was dropwise added a solution of acetyl chloride (942 mg) in methylene chloride (5 ml) under stirring and ice-cooling over the period of 7 minutes. The mixture was further stirred for 70 minutes at room temperature. The pyridine was distilled off under reduced pressure and ethyl acetate was added to the residue. The resultant mixture was washed twice with water and adjusted to pH 4 with hydrochloric acid and then an aqueous solution of sodium chloride, dried and concentrated under reduced pressure to give an oily substance. This oily substance was crystallized by treating with a mixture of diethyl ether and a small amount of n-hexane, and collected crude crystals (2.5 g) were washed with n-hexane and thus obtained crystals were recrystallized from diethyl ether to give pure crystals (1.78 g) of diethyl 2-methyl-4-(2-nitrophenyl)-6-acetoxymethyl-1,4-dihydropyridine-3,5-dicarboxylate, m.p. 89° to 90° C.

(6) To a solution of diethyl 2-methyl-4-(3-nitrophenyl)-6-hydroxymethyl-1,4-dihydropyridine-3,5-dicarboxylate (1.95 g) in dried pyridine (25 ml) was dropwise added a solution of acetyl chloride (785 mg) in methylene chloride (5 ml) under ice-cooling and stirring over the period of 10 minutes. The mixture was further stirred for 50 minutes at room temperature. After removing the solvent, the residue was dissolved in ethyl acetate. The extract was washed with water five times and an aqueous solution of sodium chloride in turn, and dried over magnesium sulfate. The solvent was removed from the extract to give a red oil (2.47 g). The oil was crystallized by treating with diethyl ether, and the crystals were washed with n-hexane and collected by filtration to give crude crystals (2 g). These crystals were dissolved in diethyl ether and the mixture was filtered on silica gel. The filtrate was concentrated under reduced pressure and the crystalline residue was recrystallized from a mixture of diethyl ether and n-hexane to give pure crystals (1.45 g) of diethyl 2-methyl-4-(3-nitrophenyl)-6-acetoxymethyl-1,4-dihydropyridine-3,5-dicarboxylate, m.p. 133° to 135° C.

(7) To a mixture of 2-(N-methyl-N-benzylamino)ethyl 2-methyl-4-(3-nitrophenyl)-5-ethoxycarbonyl-6-hydroxymethyl-1,4-dihydropyridine-3-carboxylate (630 mg) in pyridine (10 ml) was added a solution of acetyl chloride (146 mg) in methylene chloride (3 ml) under stirring and ice-cooling. The resultant mixture was further stirred at 50° to 60° C. for 2 hours. After removing the pyridine, water and ethyl acetate were added to the residue and the aqueous layer was adjusted to pH 4. The organic layer was separated, dried over magnesium sulfate and concentrated under reduced pressure to give an oily substance (800 mg). This oily substance was subjected to column chromatography on silica gel with an eluent [a mixture of 2 parts of benzene and 1 part of ethyl acetate by volume] to give an oil (620 mg) of 2-(N-methyl-N-benzylamino)ethyl 2-methyl-4-(3-nitrophenyl)-5-ethoxycarbonyl-6-acetoxymethyl-1,4-dihydropyridine-3-carboxylate.

I.R. Spectrum (film)
$\nu$(cm$^{-1}$): 3370, 1747, 1690, 1650, 1615, 1530, 1480, 1350, 1210, 1100, 1045, 740, 700

N.M.R. Spectrum ($\delta$: CDCl$_3$+D$_2$O)
ppm: 1.18 (3H, t, J=7 Hz), 2.18 (6H, s), 2.36 (3H, s), 2.6 (2H, t, J=6 Hz), 3.5 (2H, s), 4.06 (2H, q, J=7 Hz), 4.15 (2H, t, J=6 Hz), 5.13 (1H, s), 5.31 (2H, s), 6.7 (1H, m), 7.23 to 8.08 (9H, m).

Thus obtained oil (580 mg) was dissolved in diethyl ether, and to the resultant solution was bit by bit added a diethyl ether solution of maleic acid to give a precipitating oil. This oil was washed with diethyl ether twice by decantation and pulverized by n-hexane to give powder (405 mg) of 2-(N-methyl-N-benzylamino)ethyl 2-methyl-4-(3-nitrophenyl)-5-ethoxycarbonyl-6-acetoxymethyl-1,4-dihydropyridine-3-carboxylate maleate, m.p. 58° to 65° C.

(8) To a solution of diethyl 2-methyl-4-(2-nitrophenyl)-6-hydroxymethyl-1,4-dihydropyridine-3,5-dicarboxylate (1.95 g) in pyridine (25 ml) was dropwise added a solution of benzoyl chloride (2.0 g) in methylene chloride (5ml) over 5 minutes at 5° to 6° C. with stirring. The resultant mixture was stirred for 15 minutes at the same temperature and then at room temperature for 2 hours, and followed by stirring at 50° C. for an hour and a half. After the reaction was over, the pyridine was distilled off and to the residue was added ethyl acetate and water. The ethyl acetate layer was separated, washed with dil. hydrochloric acid twice and then aqueous solution of sodium bicarbonate, and dried over magnesium sulfate. The solvent was removed and the residue was soon crystallized by treating with diethyl ether and collected by filtration. These crude crystals were washed with a mixture of diethyl ether and a small amount of ethyl acetate to give crystals, which was recrystallized from ethyl acetate (25 ml) to give powders of diethyl 2-methyl-4-(2-nitrophenyl)-6-benzoyloxymethyl-1,4-dihydropyridine-3,5-dicarboxylate, m.p. 156° to 157° C.

(9) To a solution of diethyl 2-methyl-4-(2-nitrophenyl)-6-hydroxymethyl-1,4-dihydropyridine-3,5-dicarboxylate (1.95 g) in pyridine (25 ml) was dropwise added over 5 minutes a solution of p-chlorophenoxyacetyl chloride (3.07 g) in methylene chloride under stirring and ice-cooling. The resultant mixture was stirred overnight under cooling with water at 20° C. After removal of the pyridine, water was added to the residue. The precipitated oily substance was extracted with ethyl acetate. The extract was adjusted to pH 4 to 5 with dil. hydrochloric acid, washed each three times with water and then an aqueous solution of sodium bicarbonate and dried over magnesium sulfate. The solvent was distilled off and the residual oil (4.75 g) was subjected to column chromatography on silica-gel using an eluent (benzene: ethyl acetate=10:1) to give an oil (2.65 g) of diethyl 2-methyl-4-(2-nitrophenyl)-6-(4-chlorophenoxy)acetoxymethyl-1,4-dihydropyridine-3,5-dicarboxylate, m.p. 86° to 88° C. (recrystallized from a mixture of diisopropylether and ethanol).

N.M.R. Spectrum ($\delta$, CDCl$_3$+D$_2$O)
ppm: 1.13 (6H, t, J=7 Hz), 2.2 (3H, s), 4.03, 4.08 (4H, q, J=7 Hz), 4.73 (2H, s), 5.43 (2H, s), 5.88 (1H, s), 6.53 (1H, broad s), 6.76 to 7.83 (8H, m)

EXAMPLE 7

Stirring a solution of diethyl 2-methyl-4-(2-chlorophenyl)-6-hydroxymethyl-1,4-dihydropyridine-3,5-dicarboxylate (1.1395 g) in dried pyridine (10 ml) at room temperature, a solution of p-toluenesulfonyl chloride (629.1 mg) in dried pyridine (10 ml) was dropwise added gradually thereto. The resultant mixture was stirred at room temperature for 1.5 hours and then heated at 80° C. for 4.5 hours with stirring. After removal of the pyridine, water was added to the residue and the resultant aqueous mixture was acidified with dil. hydrochloric acid and extracted twice with ethyl acetate. The extract was washed with dil. hydrochloric acid and then water, and dried. The resultant brown viscous oil was purified by column chromatography on silica-gel using an eluent (benzene: diethyl ether=1:1) to give an orange oil, which was crystallized by treating with diethyl ether. The resultant crystals were collected by filtration and recrystallized from a mixture of diethyl ether and n-hexane to give orange-yellowish prisms (0.1926 g) of diethyl 2-methyl-4-(2-chlorophenyl)-6-formyl-1,4-dihydropyridine-3,5-dicarboxylate, m.p. 87° to 88° C., which was identified with an authentic sample.

EXAMPLE 8

(1) A solution of diethyl 2-methyl-4-(2-nitrophenyl)-6-formyl-1,4-dihydropyridine-3,5-dicarboxylate (0.9709 g) and hydrazine hydrate (0.1252 g) in n-propyl alcohol (10 ml) was stirred at room temperature for 30 minutes. The resultant mixture contained mainly diethyl 2-methyl-4-(2-nitrophenyl)-6-hydrazonemethyl-1,4-dihydropyridine-3,5-dicarboxylate. Then the mixture was refluxed for 6 hours. After allowing to stand the resultant solution in a refrigerator overnight, the precipitating crystals were collected by filtration to give ethyl 2-methyl-4-(2-nitrophenyl)-5-oxo-1,4,5,6-tetrahyro-3-pyrido[2,3-d]-pyridazine-3-carboxylate (263.9 mg). The product was recrystallized from a mixture of ethanol and N,N-dimethylformamide to give the pure product, m.p. 279° to 281° C.

(2) A solution of diethyl 2-methyl-4-(2-chlorophenyl)-6-hydroxymethyl-1,4-dihydropyridine-3,5-dicarboxylate (592.5 mg) and p-toluenesulfonic acid (catalytic amount) in ethanol (6 ml) was refluxed for 4 hours. After the resultant solution was concentrated, diethyl ether was added to the residue. The precipitating crystals were collected by filtration to give ethyl 2-methyl-4-(2-chlorophenyl)-5-oxo-1,4,5,7-tetrahydrofuro[3,4-b]pyridine-3-carboxylate (317.5 mg). The crude product was recrystallized from ethyl acetate to give colorless granules (210.3 mg). m.p. 211° to 212° C.

(3) A solution of diethyl 2-methyl-4-(2-thienyl)-6-hydroxymethyl-1,4-dihydropyridine-3,5-dicarboxylate (400 mg) and p-toluenesulfonic acid (catalytic amount) in 99% ethanol (10 ml) was refluxed with stirring for 2 hours. After the resultant solution was concentrated, the residue was pulverized. The powder was recrystallized from ethyl acetate to give colorless prisms (203.2 mg) of ethyl 2-methyl-4-(2-thienyl)-5-oxo-1,4,5,7-tetrahydrofuro[3,4-b]pyridine-3-carboxylate, m.p. 232° C.

EXAMPLE 9

(1) A mixture of diethyl 2-methyl-4-(2-chlorophenyl)-6-hydroxymethyl-1,4-dihydropyridine-3,5-dicarboxylate (379.8 mg) and triphenylphosphine (314.7 mg) in carbon tetrachloride (5 ml) was refluxed for 3.5 hours. After the solvent was removed, the residue was dried under reduced pressure to give diethyl 2-methyl-4-(2-chlorophenyl)-6-chloromethyl-1,4-dihydropyridine-3,5-dicarboxylate. To this residue in 99% ethanol (10 ml) was added N-methylpiperazine (200 mg) and the solution was stirred at room temperature for 50 hours. Ethanol was removed from the reaction mixture and to the residue was added water. The mixture was extracted with ethyl acetate. After washing the extract with water, the extract was back-extracted with dilute hydrochloric acid. The aqueous layer was washed with diethyl ether, basified with an aqueous solution of sodium bicarbonate, and then extracted with ethyl acetate. The extract was washed with water, dried and then concentrated to give crude crystals (115.2 mg) of diethyl 2-methyl-4-(2-chlorophenyl)-6-(N-methylpiperazin-1-yl-methyl)-1,4-dihydropyridine-3,5-dicarboxylate. The crude crystals were recrystallized from a mixture of ethanol and diethyl ether to give colorless needles, m.p. 179° to 180° C.

(2) A mixture of diethyl 2-methyl-4-(2-chlorophenyl)-6-hydroxymethyl-1,4-dihydropyridine-3,5-dicarboxylate (1.1395 g) and triphenylphosphine (1.1803 g) in carbon tetrachloride (10 ml) was heated under reflux for 2 hours. After removing the solvent under reduced pressure, the residue was dissolved in 99% ethanol (20 ml). To the solution was added N-(2-hydroxyethyl)piperazine (859 mg) and the mixture was heated at 70° to 75° C. for 8 hours. The resultant mixture was concentrated under reduced pressure and the residue was dissolved in ethyl acetate. The solution was washed with water and then back-extracted with an aqueous dilute hydrochloric acid. The aqueous layer was washed with diethyl ether, alkalized with sodium bicarbonate and then extracted with ethyl acetate. The extract was washed with water, dried over magnesium sulfate and conentrated under reduced pressure to give crude crystals (560 mg). These were recrystallized from a mixture of ethanol and diethyl ether to give pure crystals (80 mg) of diethyl 2-methyl-4-(2-chlorophenyl)-6-[N-(2-hydroxyethyl)piperazin-1-yl]methyl-1,4-dihydropyridine-3, 5-dicarboxylate, m.p. 145° to 147° C.

(3) A mixture of 2-chloroethyl 2-methyl-4-(3-nitrophenyl)-5-ethoxycarbonyl-6-diethoxymethyl-1,4-dihydropyridine-3-carboxylate (8.5 g), N-methylbenzylamine (2.70 g) and triethylamine (2.6 g) in ethanol (40 ml) was heated under reflux for 56 hours. After removing the ethanol, the residue was dissolved in a mixture of ethyl acetate and water. The organic layer was separated and washed with water, dried over magnesium sulfate and concentrated under reduced pressure to give an oil (11 g). The oil was subjected to column chromatography on silica gel with an eluent [a mixture of 10 parts of benzene and one part of diethyl ether by volume] to give an oil (7.35 g) of 2-(N-benzyl-N-methylamino)ethyl 2-methyl-4-(3-nitrophenyl)-5-ethoxycarbonyl-6-diethoxymethyl-1,4-dihydropyridine-3-carboxylate.

I.R. Spectrum (film)
$\nu(cm^{-1})$:3400, 1700, 1690, 1610, 1523, 1475, 1350, 1275, 1197, 1092, 1055, 755, 698

N.M.R. Spectrum ($\delta$:CDCl$_3$+D$_2$O)
ppm:1.21 (9H, t, J=7 Hz), 2.21 (3H, s), 2.36 (3H, s), 2.63 (2H, t, J=6 Hz), 3.5 (2H, s), 3.65 (2H, q, J=7 Hz), 3.66 (2H, q, J=7 Hz), 4.1 (2H, q), 4.18 (2H, t, J=6 Hz), 5.18 (1H, s), 6.2 (1H, s), 6.86 (1H, s), 7.16 to 8.16 (4H, m)

(4) A mixture of 2-chloroethyl 2-methyl-4-(3-nitrophenyl)-5-ethoxycarbonyl-6-diethoxymethyl-1,4-dihydropyridine-3-carboxylate (2.0 g), diethylamine (1.75 g) and sodium iodide (60.3 mg) in n-propylalcohol (4 ml) was refluxed for 17 hours. After removal of the solvent from the reaction mixture, water and ethyl acetate were added to the residue. The ethyl acetate layer was washed twice with water, dried over magnesium sulfate, and concentrated to give a brown oil (2.46 g) of 2-(N,N-diethylamino)ethyl 2-methyl-4-(3-nitrophenyl)-5-ethoxycarbonyl-6-diethoxymethyl-1,4-dihydropyridine-3-carboxylate, which was identified by converting to the corresponding 6-formyl compound (oil) and then to the corresponding 6-cyano compound, m.p. 150° to 152° C.

(5) A mixture of 2-chloroethyl 2-methyl-4-(3-nitrophenyl)-5-ethoxycarbonyl-6-diethoxymethyl-1,4-dihydropyridine-3-carboxylate (1.491 g) and potassium carbonate (456.1 mg) in ethanol (30 ml) was refluxed for 6.5 hours. After removal of the ethanol, the residue was extracted with ethyl acetate. The ethyl acetate layer was washed twice with water and dried, and the solvent was distilled off to give a viscous oil (1.47 g). This oil was purified by column chromatography and the resultant oil (0.82 g) was crystallized and recrystallized from diisopropyl ether to give yellow granules (0.60 g) of 2-hydroxyethyl 2-methyl-4-(3-nitrophenyl)-5-ethoxycarbonyl-6-diethoxymethyl-1,4-dihydropyridine-3-carboxylate, m.p. 98° to 100° C.

A mixture of the above obtained yellow granules (1.46 g) obtained in Example 1-12 and potassium carbonate (0.41 g) in 80% ethanol (20 ml) was refluxed for 6.5 hours. After removal of the ethanol, water was added to the residue, and the mixture was acidified with dilute hydrochloric acid and extracted with ethyl acetate. The extract was washed three times with water, dried, and concentrated to give a brown oil (1.54 g). Thus obtained oil was subjected to column chromatography on silica gel with an eluent (a mixture of five parts of benzene and two part of ethyl acetate by volume), and the fraction containing the designated substance was concentrated to give a reddish oil (1.31 g) of 2-hydroxyethyl 2-methyl-4-(2-nitrophenyl)-5-ethoxycarbonyl-6-diethoxymethyl-1, 4-dihydropyridine-3-carboxylate.

I.R. Spectrum (film)
$\nu(cm^{-1})$;3530, 3410, 3360 (shoulder), 1706 (shoulder), 1697, 1690 (shoulder), 1532, 1480, 1356, 1275, 1208, 1100, 1105, 860, 832, 785

N.M.R. Spectrum ($\delta$, CDCl$_3$)
ppm: 1.0 to 1.45 (9H, m), 2.39 (3H, s), 2.2 to 2.73 (1H, broad), 3.4 to 4.5 (10H, m)

(6) A mixture of diethyl 2-methyl-4-(2-nitrophenyl)-6-formyl-1,4-dihydropyridine-3,5-dicarboxylate (388.37 mg), ethylene glycol (186.21 mg) and p-toluenesulfonic acid (catalytic amount) in absolute benzene. (5 ml) was refluxed for 45 minutes under azeotropic dehydration. The reaction mixture was allowed to stand and washed twice with an aqueous solution of sodium bicarbonate. After removal of the solvent, the residue immediately turned into crystals. Thus obtained crystals were recrystallized from a mixture of ethanol and diisopropyl ether to give yellow pure crystals (0.32 g) of diethyl 2-methyl-4-(2-nitrophenyl)-6-ethylenedioxymethyl-1,4-dihydropyridine-3,5-dicarboxylate, m.p 152° to 153.5° C. (7) A mixture of diethyl 2-methyl-4-(2-nitrophenyl)-6-hydroxymethyl-1,4-dihydropyridine-3,5-dicarboxylate (1.9518g) and triphenylphosphine (1.4425 g) in carbon tetrachloride (20 ml) was refluxed for 5 hours. After removal of the solvent, the residue was added to water and extracted with ethyl acetate. The extract was washed with water and dried. Removal of the solvent gave an orange-yellow oil (3.63 g). This oil was subjected to column chromatography on silica gel with an eluent (benzene:ethyl acetate=5:2) to give an oil (517 mg) of diethyl 2-methyl-4-(2-nitrophenyl)-6-chloromethyl-1,4-dihydropyridine-3,5-dicarboxylate.

(8) To a solution of an oil (517 mg) of diethyl 2-methyl-4-(2-nitrophenyl)-6-chloromethyl-1,4-dihydropyridine-3,5-dicarboxylate in 95% ethanol (1 ml) was added sodium cyanide (93 mg), and the resultant mixture was stirred at room temperature for 2 hours. Addition of water to the reaction mixture precipitated an oil. The oil was extracted twice with ethyl acetate, and the organic layer was washed with water twice and with a saturated solution of sodium chloride and dried. Removal of the solvent gave a foamy oil (0.42 g), which was subjected to column chromatography on silica gel with an eluent (benzene:ethyl acetate=5:2) to give a reddish orange oil (0.2783 g) of diethyl 2-methyl-4-(2-nitrophenyl)-6-cyanomethyl-1,4-dihydropyridine-3,5-dicarboxylate.

I.R. Spectrum (liquid)
$\nu(cm^{-1})$: 2210

EXAMPLE 10

(1) To a mixture of 2-allyloxybenzaldehyde (8.11 g) and ethyl 4,4-diethoxyacetoacetate (12.00 g) in benzene (about 31 ml) was added acetic acid (0.36 g) and to the resultant mixture was added each one third portion of piperdine (0.51 g) in benzene (about 4 ml) with an interval of 20 minutes. After refluxing for 2.5 hours the mixture was cooled to room temperature and benzene (50 ml) was added thereto. The resultant mixture was washed three times with water and dried over magnesium sulfate. Removing of the solvent, a red oil was gained and to this oil was added ethyl 3-aminocrotonate (8.56 g). The resultant mixture was warmed at 55° to 60° C. for 6.5 hours under stirring and further for 2 hours at 72° to 75° C. and finally for 2.5 hours at 105° to 107° C. The reaction mixture was subjected to column chromatography on silica gel with an eluent to give an oil (19.38 g) from the eluate. The oil (3.0 g) was further purified on silica gel column chromatography with an eluent (benzene:ethyl acetate=20:1) to give an oil (1.77 g) of diethyl 2-methyl-4-(2-allyloxyphenyl)-6-diethoxymethyl-1,4-dihydropyridine-3,5-dicarboxylate I.R. Spectrum (liquid)
$\nu(cm^{-1})$: 3430, 1695, 1650, 1618, 1490, 1371, 1280, 1095, 930, 760

N.M.R. Spectrum ($\delta$, CDCl$_3$)
ppm: 1.0–1.5 (12H, m), 2.28 (3H, s), 3.4–4.3 (8H, m), 5.35 (1H, s), 6.17 (1H, s), ca 4.5, ca 5–5.6, ca 5.7–6.4 (5H, m), 6.5–7.4 (5H, m)

(2) To a solution of diethyl 2-methyl-4-(2-allyloxyphenyl)-6-diethoxymethyl-1,4-dihydropyridine-3,5-dicarboxylate (1.5 g) in acetone (15 ml) was added 6N-hydrochloric acid (1.5ml) with stirring and the resultant mixture was further stirred for an hour and 45 minutes at room temperature. The solvent was removed, and addition of water to the residue resulted a yellowish suspension with precipitation of an oil, which was immediately solidified. After being allowed to stand for about 10 minutes, the precipitated solids were collected by filteration and washed with water and dried. Thus obtained crude crystals were recrystallized from a mixture of diisopropyl ether and acetone to give orange-yellow granules of diethyl 2-methyl-4-(2-allyloxyphenyl)-6-formyl-1,4-dihydropyridine-3,5-dicarboxylate, m.p. 129° to 131° C.

(3) A mixture of diethyl 2-methyl-4-(2-allyloxyphenyl)-6-formyl-1,4-dihydropyridine-3,5-dicarboxylate (4.53 g), hydroxylamine hydrochloride (866.9 mg), sodium acetate (1.2093 g) in acetic acid was stirred at room temperature for an hour. Acetic anhydride (3.5 ml) was added to the mixture and the resultant mixture was stirred at 93° to 98° C. for 3 hours. The acetic acid was distilled off under reduced pressure, and the residue was neutralized with a saturated aqueous solution of sodium bicarbonate and extracted twice with methylene chloride. The extract was washed with water twice and dried. Removal of the solvent gave a brown oil (6.42 g), which was immediately crystallized. The crystals were pulverized with diisopropyl ether to give yellow powder (3.21 g), which was recrystallized from 90% methanol to give orange-yellow crystals of diethyl 2-methyl-4-(2-allyloxyphenyl)-6-cyano-1,4-dihydropyridine-3,5-dicarboxylate, m.p. 143° to 145° C.

(4) To a solution of diethyl 2-methyl-4-(2-allyloxyphenyl)-6-formyl-1,4-dihydropyridine-3,5-dicarboxylate (4.70 g) in ethanol (100 ml) was gradually added at 4° C. sodium borohydride (445.2 mg) and the resultant mixture was stirred at 4° C. for 1.5 hours under ice-cooling. The reaction mixture was acidified with 50% acetic acid and ethanol was removed. To the residue was added water and the aqueous mixture was stirred for 10 minutes. The powder was collected by filtration and washed with water to give crude crystals (4.49 g), which were recrystallized from methanol to give yellow crystals of diethyl 2-methyl-4-(2-allyloxyphenyl)-6-hydroxymethyl-1,4-dihydropiridine-3,5-dicarboxylate, m.p. 124° to 126° C.

EXAMPLE 11

(1-i) To a mixture of 2-cyanobenzaldehyde (5.0 g), methyl 4, 4-dimethoxyacetoacetate (7.39 g) and acetic acid (0.458 g) in benzene (15 ml) was added portionwise each one third of a solution of piperidine (390 mg) in benzene (5 ml) for each 20 minutes' interval. The mixture was heated to reflux for 2 hours and the resulting water was removed off azeotropically during the reaction course. After cooling, the reaction mixture was shaken with a mixture of benzene (50 ml) and water (30 ml), and the organic layer was separated and washed with diluted aqueous sodium bicarbonate solution and water. The aqueous washings were extracted with benzene (30 ml). The benzene extract was combined with the above organic layer, washed with water, dried over magnesium sulfate and evaporated to dryness under reduced pressure. The oily residue (14.8 g) was chromatographed on a column of silica-gel (200 g) and eluted with a mixture of benzene and ethyl acetate (25:1, v/v) to give an oily methyl 2-(2-cyano-benzylidene)-4,4-dimethoxyacetoacetate (6.90 g). The thin layer chromatogram and N.M.R. spectrum of this product show that it consisted of a mixture of two stereoisomers.

N.M.R. δ ppm. (CDCl$_3$)

3.4 (s, 3H); 3.48 (s, 3H); 3.78 and 3.90 (3H, each s); 4.83 and 5.09 (1H, each s); 7.43–7.8 (m, 4H); 8.0 and 3.15 (1H, each s)

(1-ii) A mixture of above obtained methyl 2-(2-cyanobenzylidene)-4,4-dimethoxyacetoacetate (6.8 g) and methyl 3-aminocrotonate (2.98 g) was heated under stirring at around 60° C. for 2 hours, and then the temperature was gradually raised and kept at 100° to 103° C. for 10 hours. During the reaction course, n-propylalcohol (3 ml) was added into the reaction mixture for dissolving the resulting crystalline mass. The reaction mixture was dissolved in a mixture of diisopropyl ether (9 ml) and methanol (3 ml) and allowed to stand for a while to give pale brown fine crystals of dimethyl 2-methyl-4-(2-cyanophenyl)-6-dimethoxymethyl-1,4-dihydropyridine-3,5-dicarboxylate (6.39 g), an aliquot of which was recrystallized from a mixture of diisopropyl ether and methanol (1:1, v/v) to give the pure crystals mp. 133°–134.5° C.

N.M.R. δ ppm. (CDCl$_3$)

3.4 (3H, s), 3.48 (3H, s), 3.78 and 3.9 (3H, s), 4.83 and 5.09 (1H, s), 7.43 to 7.8 (4H, m), 8.0 and 8.15 (1H, s)

(2-i) To a mixture of methyl 2-formylbenzoate (4.92 g), ethyl 4,4-diethoxyacetoacetate (7.2 g) and acetic acid (0.36 g) in benzene (15 ml) was added portionwise each one third portion of a solution of piperidine (306 mg) in benzene (5 ml) for each 20 minutes' interval, and the mixture was heated to reflux for 3 hours under removing off azeotropically the resulting water. After cooling, the reaction mixture was diluted with additional benzene (25 ml), washed three times with water and successively with diluted aqueous sodium bicarbonate solution, water and saturated aqueous sodium chloride solution and dried over magnesium sulfate. The solvent was distilled off under reduced pressure to give reddish oil (12.7 g) of crude ethyl 2-(2-methoxycarbonylbenzyliden)-4,4-diethoxyacetoacetate which was used in the following reaction without any further purification.

(2-ii) A mixture of ethyl 2-(2-methoxycarbonylbenzylidene)-4,4-diethoxyacetoacetate (12.7 g) and ethyl 3-aminocrotonate (5.03 g) was heated under stirring at around 60° to 70° C. for 1.5 hours and then the temperature was raised gradually, to keep at 90° C. for 3.5 hours and finally at 110° C. for 4.5 hours. After cooling, the reaction mixture was dissolved in ethyl acetate (50 ml), washed twice with water, dried over magnesium sulfate and evaporated to driness under reduced pressure to give reddish brown oily residue (12.8 g). The oil was treated with a mixture of diisopropyl ether and n-hexane (1:10, v/v) to give light brown crystalline powder of diethyl 2-methyl-4-(2-methyoxycarbonylphenyl)-6-diethoxymethyl-1,4-dihydropyridine-3,5-dicarboxylate (3.5 g). An additional crop (0.33 g) was recovered from the mother liquor, and further crop (1.6 g) was recovered from the whole mother liquor by subjecting the residual oil (8.0 g) to column chromatography on silica-gel (240 g), and eluted with a mixture of benzene and ethyl acetate (15:1 and 10:1, v/v), (total yield 5.43 g). A 300 mg portion of the first crop was recrystallized from 3 ml of n-hexane to give 290 mg of the pure crystals, mp 94°–95° C.

N.M.R. δ ppm (CDCl$_3$)

1.25 (6H, t, J=7 H$_Z$), 1.15 (6H, t, J=7 H$_Z$), 2.33 (3H, s), 3.92 (3H, s), 3.42–4.23 (8H, m), 6.04 (1H, s), 6.11 (1H, s), 6.6 (1H, broad s), 7.0–7.8 (4H, m)

(3) To a solution of 2-N-methylsulfomylbenzaldehyde (1.75 g), methyl 4,4-dimethoxyacetoacetate (1.70 g), and acetic acid (0.1 g) in benzene (5 ml) was added a solution of piperidine (90 mg) in benzene (3 ml) in a similar manner to the aforementioned Examples (1-i) and (2-i), and the mixture was heated to reflux for 2 hours. During the reaction course, the resulting water was removed off azeotropically. After cooling, the reaction mixture was diluted with benzene (15 ml), washed twice with diluted aqueous sodium bicarbonate solution and in turn with water and saturated aqueous sodium chloride solution, dried over magnesium sulfate and then evaporated to dryness under reduced pressure to give reddish yellow oil (3.46 g). The oil was chromatographed on a column of silica-gel (69 g) and eluted with a mixture of benzene and ethyl acetate (3.5:1, v/v) to give an oily methyl 2(2-N-methylsulfamoylbenzylidene)-4,4-dimethoxyacetoacetate (1.12 g). A mixture of thus obtained oily methyl-2(2-N-methylsulfamoylbenzylidene)-4,4-dimethoxyacetoacetate (1.0 g) and methyl 3-aminocrotonate (355 mg) was heated at 60° C. for 3 hours, and the temperature was raised gradually to 100° C. during 1.5 hours and kept at 100° C. for 5.5 hours. The reaction mixture was chromatographed on a column of silica-gel (33 g) and eluted with mixture of benzene and ethyl acetate (5:1, v/v) to give an oily dimethyl 2-methyl-4-(2-N-methylsulfamoylphenyl)-6- dimethoxymethyl-1,4-dihydropyridine-3,5-dicarboxylate (840 mg).

N.M.R. δ ppm (CDCl$_3$)

2.37 (3H, s), 2.65 (3H, d, J=3 Hz), 3.40 (3H, s), 3.45 (3H, s), 3.63 (3H, s) 3.65 (3H, s), 4.77 (1H, q, J=3 Hz), 5.11 (1H, s), 6.01 (1H, s), 6.88 (1H, broad s), 7.35–7.75 (4H, m)

(4) A mixture of methyl 2-(2-nitrobenzylidene)-4,4-dimethoxyacetoacetate (15.19 g) and methyl 3-aminocrotonate (6.50 g) was heated at 60° to 63° C. for 6 hours and at 100° to 105° C. for 4 hours and 45 minutes. The resulting crystalline mass was triturated with methanol and collected by filtration to give crystals of dimethyl 2-methyl-4-(2-nitrophenyl)-6-dimethoxymethyl-1,4-dihydropyridine-3,5-dicarboxylate (12.04 g). Thus obtained crystals (1.07 g) were recrystallized from methanol (5 ml) to give pure crystals (0.93 g), m.p. 132° to 133° C.

N.M.R. δ ppm (CDCl$_3$)

2.36 (3H, s), 3.40 (3H, s), 3.44 (3H, s), 3.56 (3H, s), 3.66 (3H, s), 5.76 (1H, s), 5.99 (1H, s), 6.85 (1H, broad s), 7.1 to 7.8 (4H, m)

(5) A mixture of 2-nitrobenzaldehyde (6.8009 g), methyl 4,4-dimethoxyacetoacetate (8.7204 g), acetic acid (0.5405 g) and piperidine (0.4598 g) in benzene (30 ml) was heated to reflux for 2 hours under azeptropic dehydration. The reaction mixture was diluted with benzene (100 ml), washed twice with water, and in turn with diluted aqueous sodium bicarbonate solution and water, dried over magnesium sulfate and evaporated to dryness under reduced pressure to give crude oily methyl 2-(2-nitrobenzylidene)-4,4-dimethoxyyacetoacetate (15.23 g).

A mixture of thus obtained crude oil (15.23 g) and ethyl 3-aminocrotonate (6.6840 g) was heated at around 65° C. for 6 hours and then at 98° to 100° C. for 5 hours. The resultant viscous brown oil was dissolved in ethyl acetate, washed three times with water, dried over magnesium sulfate and evaporated to dryness under reduced pressure to give brown oil (19.40 g). The residual oil was crystallized by trituration with methanol (10 ml) to give yellowish crystalline powder (12.77 g) of ethyl 2-methyl-4-(2-nitrophenyl)-5-methoxycarbonyl-6-dimethoxymethyl-1,4-dihydropyridine-3-carboxylate. An additional 0.53 g of crystals were recovered from the mother liquor. Recrystallization from methanol gave yellowish granules, m.p. 122°–124° C.

N.M.R. δ ppm (CDCl$_3$)

1.15 (3H, t, J=7.5 Hz), 2.38 (3H, s), 3.40 (3H, s), 3.45 (3H, s), 3.60 (3H, s), 4.04 (2H, q, J=7.5 Hz), 4.08 (2H, q, J=7.5 Hz), 5.83 (1H, s), 5.98 (1H, s), 6.77 (1H, broad s), 7.1 to 7.85 (4H, m)

(6) To a solution of 2-nitrobenzaldehyde (6.80 g), methyl 4,4-dimethoxyacetoacetate (8.72 g) and acetic acid (0.54 g) in benzene (30 ml), was added piperidine (0.46 g), in a similar manner to aforementioned examples 1-i) and 2-i), and the mixture was heated to reflux for 2 hours under azeotropic dehydration. The reaction mixture, after cooling, was diluted with benzene (100 ml), washed three times with water, and in turn with diluted aqueous sodium bicarbonate solution and water, dried over magnesium sulfated and evaporated to dryness under reduce pressure to give oily methyl 2-(2-nitrobenzylidene)-4,4-dimethoxyacetoacetate (14.73 g).

A mixture of the above obtained oil (14.70 g) and isopropyl 3-aminocrotonate (7.09 g) was heated at 60° to 63° C. for 2 hours and at 85° to 90° C. for about 10 hours. The reaction mixture was treated with ethyl acetate to give yellowish crystals which were collected by filtration and washed with methanol. The filtrate was concentrated and the residue was treated with methanol to give additional crystals. The combined crystals (11.10 g) were recrystallized from methanol to give pure crystals of isopropyl 2-methyl-4-(2-nitrophenyl)-5-methoxycarbonyl-6-dimethoxymethyl-1,4-dihydropyridine-3-carboxylate, m.p. 143°–145° C.

N.M.R. δ ppm (CDCl$_3$)

0.99 (3H, d, J=6 Hz), 1.24 (3H, d, J=6 Hz), 2.39 (3H, s), 3.37 (3H, s), 3.45 (3H, s), 3.60 (3H, s), 4.96 (1H, hept., J=6 Hz), 5.88 (1H, s), 5.96 (1H, s), 6.82 (1H, s), 7.1 to 7.8 (4H, m)

(7) To a mixture of 3-nitrobenzaldehyde (7.56 g), methyl 4,4-dimethoxyacetoacetate (9,69 g) and acetic acid (600 mg) in benzene (25 ml) was added portionwise each one fifth portion of piperidine (851 mg) in benzene (5 ml) for each 20 minutes interval and the mixture was heated to reflux for 4 hours under azeotropic dehydration. After cooling, the reaction mixture was diluted with benzene (50 ml), washed twice with diluted aqueous sodium bicarbonate solution, and in turn, with water and saturated aqueous solution of sodium chloride, dried over magnesium sulfate and evaporated to dryness under reduced pressure to give crude reddish brown oily methyl (3-nitrobenzylidene)-4,4-dimethylacetoacetate (17.82 g) which was used in the following reaction without any further purification. A mixture of above oil (17.82 g) and methyl 3-aminocrotonate (6.33 g) was heated at 60° to 65° C. for 4.5 hours, at 100° to 105° C. for 8 hours and 45 minutes. The reaction mixture was chromatographed on a column of silica-gel (440 g) and eluted with a mixture of benzene and ethyl acetate (10:1, v/v) to give crystalline product (10.46 g) of dimethyl 2-methyl-4-(3-nitrophenyl)-6-dimethoxymethyl-1,4-dihydropyridine-3,5-dicarboxylate. Thus obtained crystals (720 mg) were recrystallized from diisopropyl ether (10 ml) to give pure specimen (560 mg), mp 99° to 100° C.

N.M.R. δ ppm (CDCl$_3$)

2.47 (3H, s), 3.52 (3H, s), 3.57 (3H, s), 3.77 (3H, s), 5.25 (1H, s), 6.1 (1H, s), 6.98 (1H, broad s), 7.38 to 8.17 (4H, m)

(8) To a solution of 3-nitrobenzaldehyde (4.53 g), 2-benzyloxyethyl acetoacetate (7.79 g) and acetic acid (360 mg) in benzene (15 ml), was added a solution of piperidine (306 mg) in benzene (5 ml), in a similar manner to the aforementioned Example 1-i), and the mixture was heated to reflux for 2.5 hours under azeotropic dehydration. The reaction mixture was left to cool and diluted with benzene (50 ml), washed with water, diluted aqueous sodium bicarbonate solution and water, dried over magnesium sulfate and then evaporated to dryness under reduced pressure to give brown oily 2-benzyloxyethyl 2-(3-nitrobenzylidene)-acetoacetate (12.58 g). The mixture of the above obtained oil (12.58 g) and ethyl 3-amino-4,4-diethoxycrotonate (8.47 g) was heated at 100° to 102° C. for 4 hours and at 110° to 115° C. for 6.5 hours. After cooling, the reaction mixture was dissolved in ethyl acetate, washed twice with water and saturated aqueous sodium chloride solution, dried over magnesium sulfate and evaporated to dryness under reduced pressure. The residual brown oil (19.04 g) was chromatographed on a column of silica-gel (570 g) and eluted with a mixture of benzene and ethyl acetate (13:1, v/v) to give oily 2-benzyloxyethyl 2-methyl-4-(3-nitrophenyl)-5-ethoxycarbonyl-6-diethoxymethyl-1,4-dihydropyridine-3-carboxylate (9.64 g).

N.M.R. δ pp. (CDCl$_3$)

1.17 (6H, t, J=7 Hz), 1.23 (3H, t, J=7 Hz), 2.35 (3H, s), 3.43 to 4.4 (10H, m), 4.5 (2H, s), 5.18 (1H, s), 6.86 (1H, broad s), 7.33 to 8.13 (9H, m)

EXAMPLE 12

(1) To a solution of dimethyl 2-methyl-4-(2-cyanophenyl)-6-dimethoxymethyl-1,4-dihydropyridine-3,5-dicarboxylate (6.0 g) in acetone (60 ml) was added 6 N hydrochloric acid (6 ml), and the resultant mixture was stirred for 3 hours at room temperature. The reaction mixture was diluted with water (30 ml), and adjusted to pH 7.5 with an aqueous sodium bicarbonate solution, and acetone was distilled off under reduced pressure. The resultant crystalline mass was crushed as finely as possible with a glass rod, washed with an additional water (100 ml), collected by filtration, further washed thoroughly with water, and air-dried to give crystalline powder of dimethyl 2-methyl-4-(2-cyanophenyl)-6-formyl-1,4-dihydropyridine-3,5-dicarboxylate (5.19 g).

N.M.R. δ ppm (CDCl$_3$)

2.41 (3H, s), 3.65 (3H, s), 3.75 (3H, s), 5.5 (1H, s), 7.0 (1H, s), 7.25 to 7.66 (4H, m), 10.53 (1H, s)

(2) To a solution of diethyl 2-methyl-4-(2-methoxycarbonylphenyl)-6-diethoxymethyl-1,4-dihydropyridine-3,5-dicarboxylate (5.03 g) in acetone (50 ml) was added 6 N-hydrochloric acid (5 ml), and the mixture was stirred for 2 hours at room temperature. After adding water (30 ml), the reaction mixture was neutralized with an aqueous sodium bicarbonate solution and acetone was distilled off under reduced pressure. The resultant oily precipitates were extracted with ethyl acetate. The ethyl acetate extracts were washed with water, saturated aqueous sodium chloride solution, dried over magnesium sulfate and evaporated to dryness under reduced pressure to give reddish oil of crude diethyl 2-methyl-4-(2-methoxycarbonylphenyl)-6-formyl-1,4-dihydropyridine-3,5-dicarboxylate (4.26 g), which was used in a succeeding reaction without further purification.

N.M.R. δ ppm (CDCl$_3$)

1.1 (3H, t, J=7 Hz), 1.8 (3H, t, J=7 Hz), 2.37 (3H, s), 3.93 (3H, s), 3.9 to 4.28 (4H, m), 6.2 (1H, s), 6.98 (1H, s), 7.1 to 7.8 (4H, m), 10.2 (1H, s)

(3) A mixture of a solution of dimethyl 2-methyl-4-(2-N-methylsulfamoylphenyl)-6-dimethoxymethyl-1,4-dihydropyridine-3,5-dicarboxylate (600 mg) in acetone (6 ml) and 6 N hydrochloric acid (0.6 ml) was stirred for 2.5 hours at room temperature and adjusted to pH 7 to 8 with a diluted aqueous sodium bicarbonate solution, and then acetone was distilled off under reduced pressure. The resultant oily precipitate was triturated with additional water to give crystalline powder of dimethyl 2-methyl-4-(2-N-methylsulfamoylphenyl)-6-formyl-1,4-dihydropyridine-3,5-dicarboxylate (380 mg).

N.M.R. δ ppm (CDCl$_3$)

2.45 (3H, s), 2.65 (3H, d, J=3 Hz), 3.65 (3H, s), 3.76 (3H, s), 4.6 (1H, q, J=3 Hz), 5.22 (1H, s) 7.09 (1H, broad s), 7.35 to 7.85 (4H, m), 10.49 (1H, s)

(4) A mixture of a solution of dimethyl 2-methyl-4-(2-nitrophenyl)-6-dimethoxymethyl-1,4-dihydropyridine-3,5-dicarboxylate (10.68 g) in acetone (110 ml) and 6 N hydrochloric acid (10 ml) was stirred at 25° C. for 3 hours, which was neutrallized with an aqueous sodium bicarbonate solution and acetone was distilled off under reduced pressure. The resultant reddish yellow oily precipitates were solidified, which were cracked finely, collected by filtration, washed with water and air dried over-night to give crude crystals of dimethyl 2-methyl-4-(2-nitrophenyl)-6-formyl-1,4-dihydropyridine-3,5-dicarboxylate (9.33 g).

N.M.R. δ ppm (CDCl$_3$) 2.41 (3H, s), 3.58 (3H, s), 3.71 (3H, s), 5.88 (1H, s), 7.10 (1H, broad s), 7.2 to 7.9 (4H, m), 10.43 (1H, s)

(5) To a solution of isopropyl 2-methyl-4-(2-nitrophenyl)-5-methoxycarbonyl-6-dimethoxymethyl-1,4-dihydropyridine-3,5-carboxylate (10.5 g) in acetone (105 ml) was added 6-N hydrochloric acid (15.5 ml) and the mixture was stirred at 25° C. for 2 hours. After removal of acetone, the resultant solution was diluted with water (50 ml), made alkaline with saturated aqueous sodium bicarbonate solution, and then extracted with ethyl acetate. The ethyl acetate extract was washed twice with saturated aqueous sodium chloride solution, dried over magnesium sulfate and evaporated to dryness under reduced pressure. The reddish-yellow oily residue (11.08 g) was triturated with a mixture of diethyl ether and n-hexane to give yellowish crystalline powder of isopropyl 2-methyl-4-(2-nitrophenyl)-5-methoxycarbonyl-6-formyl-1,4-dihydropyridine-3-carboxylate (8.94 g).

N.M.R. δ ppm (CDCl$_3$)

0.97 (3H, d, J=6 Hz), 1.21 (3H, d, J=6 Hz), 2.43 (3H, s), 3.70 (3H, s), 4.97 (1H, hept., J=6 Hz), 6.00 (1H, s), 6.95 (1H, broad s), 7.2 to 7.9 (4H, m), 10.38 (1H, s)

(6) To a solution of dimethyl 2-methyl-4-(3-nitrophenyl)-6-dimethoxymethyl-1,4-dihydropyridine-3,5-dicarboxylate (7.5 g) in acetone (75 ml) was added 6 N hydrochloric acid (7.5 ml) and the mixture was stirred at room temperature for 6 hours. The pricipitates which were separated out during the reaction course were collected by filtration to give yellowish crystals of dimethyl 2-methyl-4-(3-nitrophenyl)-6-formyl-1,4-dihydropyridine-3,5-dicarboxylate (2.26 g), and the filtrate was adjusted to pH 7.5 to 8 with an aqueous sodium bicarbonate solution, and the acetone was distilled off under reduced pressure to give additional crops of orange-yellow crystals (3.84 g) of the same product (total yield, 6.1 g). A small portion of the first crop was recrystallized from methanol to give pure crystals, m.p. 157°–157.5° C.

N.M.R. δ ppm (CDCl$_3$) 2.48 (3H, s), 3.7 (3H, s), 3.81 (3H, s), 5.3 (1H, s), 7.13 to 8.17 (5H, m), 10.5 (1H, s)

(7) To a solution of 2-benzyloxyethyl 2-methyl-4-(3-nitrophenyl)-5-ethoxycarbonyl-6-diethoxymethyl-1,4-dihydropyridine-3-carboxylate (6.0 g) in acetone (60 ml) was added 6 N hydrochloric acid (6 ml) and the mixture was stirred at room temperature for 2 hours. The reaction mixture was adjusted to pH 7.5 to 8 with an aqueous sodium bicarbonate solution, and acetone was distilled off under reduced pressure. The resultant solution was diluted with water (150 ml) to separate out oily precipitates, which were extracted twice with ethyl acetate (100 ml and 50 ml, respectively). The organic layer was washed with water, dried over magnesium sulfate and evaporated to dryness under reduced pressure to give oily 2-benzyloxyethyl 2 -methyl-4-(3-nitrophenyl)-5-ethoxycarbonyl-6-formyl-1,4-dihydropyridine-3-carboxylate (5.02 g).

N.M.R. δ ppm (CDCl$_3$)

1.25 (3H, t, J=7 Hz), 2.41 (3H, s), 4.5 (4H, s), 3.5 to 4.4 (6H, m), 5.29 (1H, s), 7.3 to 8.15 (10H, m), 10.45 (1H, s)

EXAMPLE 13

(1) A mixture of dimethyl 2-methyl-4-(2-cyanophenyl)-6-formyl-1,4-dihydropyridine-3,5-dicarboxylate (2.4 g), hydroxylamine hydrochloride (539.3 mg) and sodium acetate (752.3 mg) in acetic acid (15 ml) was stirred at room temperature for 55 minutes to form dimethyl-2-methyl-4-(2cyanophenyl)-6-hydroxyiminomethyl-1,4-dihydropyridine-3,5dicarboxylate. To the reaction mixture was added acetic anhydride (2.375 g), and the mixture was heated at 110° C. for 4 hours with stirring. The reaction mixture was concentrated and treated with water (30 ml). The resultant acidic solution was adjusted to pH 7.5 to 8 with an aqueous sodium bicarbonate solution, and extracted twice with ethyl acetate. The organic layer was washed with water, saturated aqueous sodium chloride solution, and evaporated to dryness under reduced pressure. The residue was kept overnight in a refrigerator for crystallization. The resultant crystals were collected by filtration and washed with small portion of cold methanol to give crystals of dimethyl 2methyl-4-(2-cyanophenyl)-6-cyano-1,4-dihydropyridine-3,5dicarboxylate (1.71 g). Additional crop (0.9 g) was recovered from the mother liquor. The combined crystals (2.61 g) were recrystallized from methanol to give pure crystals (1.2 g), m.p. 166°–166.5° C.

N.M.R. δ ppm (CDCl$_3$) 2.4 (3H, s), 3.67 (3H, s), 3.75 (3H, s), 5.42 (1H, s), 7.2 to 7.62 (4H, m), 7.9 (1H, s)

(2) A mixture of diethyl 2-methyl-4-(2-methoxycarbonylphenyl)-6-formyl-1,4-dihydropyridine-3,5-dicarboxylate (2.6 g), hydroxylamine hydrochloride (495 mg) and sodium acetate (691 mg) in acetic acid (20 ml) was stirred at room temperature for an hour to form diethyl 2-methyl-4-(2-methoxycarbonylphenyl)-6-hydroxyiminomethyl-1,4-dihydropyridine-3,5-dicarboxylate. To the reaction mixture was added acetic anhydride (2.18 ml) and the mixture was heated at 110° C. for 3.5 hours with stirring. Acetic acid was distilled off under reduced pressure from the reaction mixture and the resultant residue was adjusted to pH 8 with an aqueous sodium bicarbonate solution and extracted with ethyl acetate. The ethyl acetate extracts were washed with water, and saturated aqueous sodium chloride solution, dried over magnesium sulfate and then evaporated to dryness. The resultant oil (2.88 g) was chromatographed on a column of silica-gel (72 g), and eluted with a mixture of benzene and ethyl acetate (10:1, v/v) to give an oil (1.6 g), which was triturated with diisopropyl ether (3 ml) to give crystalline powder (1.3 g). Recrystallization from a mixture (20 ml) of diisopropyl ether and ethanol (15:1, v/v) gave pure crystals of diethyl 2-methyl-4-(2-methoxycarbonylphenyl)-6-cyano-1,4-dihydropyridine-3,5-dicarboxylate (1.03 g), mp 126° to 127° C.

N.M.R. δ ppm (CDCl$_3$)
1.15 (3H, t, J=7 Hz), 1.24 (3H, t, J=7 Hz), 2.33 (3H, s), 3.98 (3H, s), 3.90 to 4.38 (4H, q, J=7 Hz), 6.22 (1H, s), 7.2 to 7.88 (4H, m)

(3) A mixture of dimethyl 2-methyl-4-(2-nitrophenyl)-6-formyl-1,4-dihydropyridine-3,5-dicarboxylate (3.6 g), hydroxylamine hydrochloride (764 mg) and sodium acetate (1.06 g) in acetic acid (20 ml) was stirred at room temperature for 45 minutes to form dimethyl 2-methyl-4-(2-nitrophenyl)-6-hydroxyiminomethyl-1,4-dihydropyridine-3,5-dicarboxylate. To the reaction mixture was added acetic anhydride (3.37 g) and the mixture was stirred at room temperature for 15 minutes and then heated at 100° C. for 3 hours with stirring. After removal of the acetic acid, the residue was adjusted to pH 7.5 with an aqueous sodium bicarbonate solution and extracted with ethyl acetate. The extract was washed twice with water and saturated aqueous sodium chloride solution, dried over magnesium sulfate and evaporated to dryness under reduced pressure. The resultant oil (3.80 g) was chromatographed on a column of silica-gel (110 g) and eluted with a mixture of benzene and ethyl acetate (9:1, v/v) to give crystals (2.05 g), which were recrystallized from a mixture of ethyl acetate (12 ml) and n-hexane (6 ml) to give yellow granules of dimethyl 2-methyl4-(2-nitrophenyl)-6-cyano-1,4-dihydropyridine-3,5-dicarboxylate (1.19 g), mp 170.5° to 171.5° C.

N.M.R. δ ppm (CDCl$_3$) 2.37 (3H, s), 3.6 (3H, s), 3.7 (3H, s), 5.9 (1H, s), 7.34 to 7.83 (4H, m)

(4) A mixture of isopropyl 2-methyl-4-(2-nitrophenyl)-5-methoxycarbonyl-6-formyl-1,4-dihydropyridine-3-carboxylate (3.88 g), hydroxylamine hydrochloride (0.7644 g) and sodium acetate (1.0664 g) in acetic acid (20 ml) was stirred at room temperature for an hour to form isopropyl 2-methyl-4(2-nitrophenyl)-5-methoxycarbonyl-6-hydroxyiminomethyl-1,4dihydropyridine-3-carboxylate. To the reaction mixture was added acetic anhydride (3.37 g) and the mixture was heated at 95° to 100° C. for 6 hours. After removal of the acetic acid, water was added to the residue and the mixture was extracted with ethyl acetate. The extract was washed with water, an aqueous sodium bicarbonate solution and water in turn, dried over magnesium sulfate and evaporated to dryness under reduced pressure. The residual oil (3.69 g) was chromatographed on a column of silica-gel (100 g), and eluted with a mixture of benzene and ethyl acetate (5:1, v/v) to give an oil of isopropyl 2-methyl-4(2-nitrophenyl)-5-methoxycarbonyl-6-cyano-1,4-dihydropyridine-3-carboxylate (2.0 g), which was left in a refrigerator for several days to crystallize. Recrystallization from methanol gave pure crystals, m.p. 175.5°–176.5° C.

N.M.R. δ ppm (CDCl$_3$)
0.91 (3H, d, J=6 Hz), 1.17 (3H, d, J=6 Hz), 2.33 (3H, s), 3.65 (3H, s), 4.9 (1H, hept., J=6 Hz), 5.95 (1H, s), 6.8 (1H, broad s), 7.23 to 7.85 (4H, m)

(5) A mixture of dimethyl 2-methyl-4-(3-nitrophenyl)-6-formyl-1,4-dihydropyridine-3,5-dicarboxylate (2.0 g), hydroxylamine hydrochloride (424.3 mg) and sodium acetate (591.8 mg) in acetic acid (12 ml) was stirred at room temperature for 80 minutes to form dimethyl 2-methyl-4-(3nitrophenyl)-6-hydroxyiminomethyl-1,4-dihydropyridine-3, 5-dicarboxylate. To the reaction mixture was added acetic anhydride (1.87 g) and the mixture was heated at 110° C. for 3.5 hours with stirring. The reaction mixture was evaporated to form crystalline mass which was neutralized by treating with diluted aqueous sodium bicarbonate solution and the crystalline mass were pulverized, collected by filtration and washed thoroughly with water to give crystals (1.92 g). Recrystallization from a mixture of methanol and ethyl acetate gave pure crystals of dimethyl 2-methyl-4-(3-nitrophenyl)-6-cyano-1,4-dihydropyridine-3,5-dicarboxylate (1.04 g), mp 206° to 207° C. An additional crop was recovered from the mother liquor of above recrystallization (0.6 g).

N.M.R. δ ppm (CDCl$_3$)
2.4 (3H, s), 3.65 (3H, s), 3.78 (3H, s), 5.12 (1H, s), 6.76 (1H, broad s), 7.36 to 8.1 (4H, m)

(6) A mixture of 2-benzyloxyethyl 2-methyl-4-(3-nitrophenyl)-5-ethoxycarbonyl-6-formyl-1,4-dihydropyridine-3-carboxylate (2.44 g), hydroxylamine hydrochloride (377 mg) and sodium acetate (526 mg) in acetic acid (15 ml) was stirred at room temperature for an hour to form 2-benzyloxyethyl 2-methyl-4-(3-nitrophenyl)-5-ethoxycarbonyl-6-hydroxyiminomethyl-1,4-dihydropyridine-3-carboxylate. To the reaction mixture was added acetic anhydride (1.66 g) and the mixture was stirred at room temperature for an hour and then heated at 100° C. for 3 hours with stirring. After removal of the acetic acid, the residue was adjusted to pH 7.5 with aqueous sodium bicarbonate solution and extraced twice with ethyl acetate. The extracts were washed twice with water, and saturated aqueous sodium chloride solution, dried over magnesium sulfate and evaporated to dryness in vacuo. The residual brown oil (2.6 g) was chromatographed on a column of silica-gel (78 g) and eluted with a mixture of benzene and ethyl acetate (12:1, v/v) to give an oil (1.45 g). The oil was crystallized by triturating with a small amount of mixture of diisopropyl ehter and diethyl ether, and recrystallized from a mixture of diisopropyl ether (9 ml) and ethanol (1 ml) to give pure crystals of 2-benzyloxyethyl 2-methyl-4-(3-nitrophenyl)-5-ethoxycarbonyl-6-cyano-1,4-dihydropyridine-3-carboxylate (840 mg), mp 114° to 115° C. An additional crop (560 mg) was recovered from the filtrate by concentrating the filtrate and allowing to stand the residue in a refrigerator.

N.M.R. δ ppm (CDCl$_3$)

1.27 (3H, t, J=7 Hz), 2.37 (3H, s), 3.65 (2H, t), 4.13 to 4.35 (4H, m), 4.5 (2H, s), 5.21 (1H, s), 7.2 to 8.1 (9H, m)

EXAMPLE 14

(1) To a cold solution of dimethyl 2-methyl-4-(2-cyanophenyl)-6-formyl-1,4-dihydropyridine-3,5-dicarboxylate (2.3 g) in methanol (46 ml) at −5° C. was added portionwise sodium borohydride (140.7 mg) for 10 minutes, during which the temperature was kept at −4° to −5° C. with stirring. The mixture was stirred for additional 15 minutes at −6° C. The reaction mixture was diluted with water (20 ml) and acidified to about pH 5 with 50% actic acid, and then condensed under reduced pressure to separate out crystalline product. After adding water (30 ml), the crystals were collected by filtration, washed thoroughly with water and dried. Thus obtained crystals (2.05 g) were recrystallized from methanol (15 ml) to give pure crystals of dimethyl 2-methyl-4-(2-cyanophenyl)-6-hydroxymethyl-1,4dihydropyridine-3,5-dicarboxylate (1.67 g), mp 177° to 178° C.

N.M.R. δ ppm (CDCl$_3$)

2.4 (3H, s), 3.63 (3H, s), 3.66 (3H, s), 4.8 (2H, broad s), 3.52 (1H, m), 5.35 (1H, s), 7.1 to 7.63 (4H, m)

(2) To a solution of diethyl 2-methyl-4-(2-methoxycarbonylphenyl)-6-formyl-1,4-dihydropyridine-3,5-dicarboxylate (1.2 g) in ethanol (15 ml) was added portionwise sodium borohydride (62.3 mg) at 0° C. over 30 minutes with stirring. The mixture was stirred for further 20 minutes at 0° C. The reaction mixture was adjusted to pH 6 with 50% acetic acid and ethanol was distilled off under reduced pressure. The residual solution was shaken with a mixture of water and ethyl acetate, and the organic layer was separated, washed with water, aqueous sodium bicarbonate solution and water, dried over magnesium sulfate and evaporated to dryness under reduced pressure. The residual oil (1.0 g) was triturated in diethyl ether (2 ml) to give crude crystals. Any recrystallization of the crude crystals were resulted in insufficient purification. The recovered product (0.9 g) was chromatographed on a column of silica-gel (27 g) and eluted with a mixture of benzene and ethyl acetate (7:1, v/v) to give purified oil of diethyl 2-methyl-4-(2-methoxycarbonylphenyl)-6-hydroxymethyl-1,4-dihydropyridine-3,5-dicarboxylate (800 mg), which was crystallized and recrystallized from a mixture of diethyl ether and n-hexane to give pure crystals (500 mg), mp 106° to 108° C.

N.M.R. δ ppm (CDCl$_3$)

1.05 (3H, t, J=7 Hz), 1.1 (3H, t, J=7 Hz), 2.25 (3H, s), 3.90 (3H, s), 3.85 to 4.13 (2H, m), 4.71 (2H, broad s), 5.98 (1H, s), 7 to 7.6 (5H, m)

(3) To a cold suspension (−2° C.) of dimethyl 2-methyl-4-(2-N-methyl-sulfamoylphenyl)-6-formyl-1,4-dihydropyridine-3,5-dicarboxylate (350 mg) in methanol (7 ml) was added each one third portion of sodium borohydride (17.85 mg) over 2 minutes with stirring. Stirring was continued for additional an hour and 40 minutes at −5° to −4° C., during which, the reaction mixture was diluted twice with methanol; i.e. with 3 ml, after 30 minutes and with 4 ml after 1 hour; and a small portion of sodium borohydride (9 mg) was added to the reaction mixture after 1 hour and 20 minutes. Water (30 ml) was added to the reaction mixture and the resultant mixture was left to cool for 1 hour to form crystalline precipitates. The resulting crystals (260 mg) were collected by filtration and recrystallized from methanol (3 ml) to give dimethyl 2-methyl-4-(2-N-methylsulfamoylphenyl)-6-hydroxymethyl-1,4-dihydropyridine-3,5-dicarboxylate, m.p. 210° to 212° C.

N.M.R. δ ppm (DMSO-d6)

2.39 (3H, s), 3.33 (3H, s), 3.59 (6H, s), 4.66 (2H, broad d, J=5 Hz), 5.03 (1H, s), 5.59 (1H, broad t, J=5 Hz), 7.3–7.78 (5H, m), 7.34 (1H, s), 8.6 (1H, broad s)

(4) A solution of dimethyl 2-methyl-4-(2-nitrophenyl)-6-formyl-1,4-dihydropyridine-3,5-dicarboxylate (3.60 g) in methanol (72 ml) was cooled at 0° C., and sodium borohydride (0.2271 g) was added bit by bit thereto under cooling with stirring. The mixture was stirred at the same temperature for 15 minutes. The reaction mixture was adjusted to about pH 6 with 50% acetic acid and the methanol was distilled off under reduced pressure below 30° C. The residual solution was diluted with water (100 ml) and extracted with ethyl acetate. The extract was washed with water, an aqueous sodium bicarbonate solution and water in turn, dried over magnesium sulfate and then evaporated to dryness. The residual oil (3.70 g) was crystallized by triturating with diisopropyl ether to give crude crystals (2.74 g), which were recrystallized in first from methanol (8 ml) and then from ethyl acetate (10 ml) to give pure crystals of dimethyl 2-methyl-4-(2-nitrophenyl)-6-hydroxymethyl-1,4-dihydropyridine-3,5-dicarboxylate (770 mg), mp 164.5° to 165° C. The whole mother liquor of above recrystallizations were combined together and concentrated. The crystalline residue was collected by filtration and washed with methanol (5 ml) to give additional crystals (1.72 g), which were recrystallized from ethyl acetate to give additional pure specimen of the same product obtained above, (840 mg) m.p. 164.5° to 165° C. Total yield, 1.61 g.

N.M.R. δ ppm (CDCl$_3$)

2.33 (3H, s), 3.56 (3H, s), 3.58 (3H, s), 4.76 (2H, s), 5.75 (1H, s), 7.25 to 7.75 (4H, m)

(5) A solution of isopropyl 2-methyl-4-(2-nitrophenyl)-5-methoxycarbonyl-6-formyl-1,4-dihydropyridine-3-carboxylate (3.88 g) in methanol (70 ml) was cooled below −3° C., and sodium borohydride (0.2082 g) was bit by bit added thereto with stirring. After stirring for further 30 minutes at −2° C., the mixture was acidified with 50% acetic acid, and methanol was removed off under reduced pressure. The resultant mixture was diluted with water and extracted with ethyl acetate. The extract was washed with water, a dilute aqueous sodium bicarbonate solution and water in turn, dried over magnesium sulfate and evaporated to dryness under reduced pressure to give a reddish viscous oil (4.37 g), which was triturated with a mixture of diethyl ehter and n-hexane to give yellowish crystalline powder (3.75 g). Recrystallization form methanol (10 ml) gave yellowish granules of isopropyl 2-methyl-4-(2-nitrophenyl)-5-methoxycarbonyl-6-hydroxymethyl-1,4-dihydropyridine-3-carboxylate (2.38 g), m.p. 135° to 137° C., which were further recrystallized from ethyl acetate (5 ml) to give the pure specimen (1.08 g), m.p. 136.5° to 138° C.

N.M.R. δ ppm (CDCl$_3$)

0.96 (3H, d, J=6 Hz), 1.22 (3H, d, J=6 Hz), 2.38 (3H, s), 3.53 (3H, s), 4.70 (2H, s), 4.94 (1H, hept., J=6 Hz), 5.83 (1H, s), ca 7.0 to 8.0 (5H, m)

(6) To a cold mixture of 2-benzyloxyethyl 2-methyl-4-(2-nitrophenyl)-5-ethoxycarbonyl-6-formyl-1,4-dihydropyridine-3-carboxylate (1.8 g) in ethanol (36 ml) was added sodium borohydride (75.5 mg) below −3° C. and the resultant mixture was stirred at −3° to −5° C. for 40 minutes. The reaction mixture was adjusted to pH 5 to 6 with 50% acetic acid and the ethanol was distilled off under reduced pressure. The residue was diluted with water (100 ml) to separate out crystalline mass, which were pluverized and collected by filtration. The crystals (1.57 g) were recrystallized from a mixture of diethyl ether and n-hexane. The obtained crystals (910 mg) were not pure enough to analyze, then these were combined again with filtrate and purified through column chromatography on silica-gel column and eluted with a mixture of benzene and ethyl acetate (10:1, v,v) to give an oil (1 g), which was crystallized and recrystallized from a mixture of diisopropyl ether and ethanol to give pure crystals of 2-benzyloxyethyl 2-methyl-4-(2-nitrophenyl)-5-ethoxycarbonyl-6-hydroxymethyl-1,4-dihydropyridine-3-carboxylate (530 mg) m.p. 96° to 97° C.

N.M.R. δ ppm (CDCl$_3$)

1.10 (3H, t, J=7 Hz), 2.30 (3H, s), 4.47 (2H, s), 3.50–4.33 (6H, m), 4.73 (2H, d, J=5 Hz), 7.05–7.75 (9H, m)

(7) To a cold suspension of dimethyl 2-methyl-4-(3-nitrophenyl)-6-formyl-1,4-dihydropyridine-3,5-dicarboxylate (3.84 g) in methanol (76 ml) was added portionwise sodium borohydride (221.8 mg) at −7° C. over 7 minutes with stirring. Stirring was continued for further 5.5 hours during the course additional portion of sodium borohydride (40 mg) was added to the reaction mixture. The resultant mixture was diluted with water (50 ml), adjusted to pH 5 to 6 with 50% aqueous acetic acid, and a small amount of insoluble substance was filtered off. The filtrate was evaporated and the residual mixture of solids and oils was washed with diisopropyl ether (10 ml) to give solid product (2.7 g). The solid product was recrystallized once from a mixture (20 ml) of methanol and diisopropyl ether (yield 1.78 g) and then recrystallization from methanol (6 ml) to give pure crystals of dimethyl 2-methyl-4-(3-nitrophenyl)-6-hydroxymethyl-1,4-dihydropyridine-3,5-dicarboxylate (1.48 g), m.p. 145° to 146° C. An additional crop was recovered from the mother liquor of the first recrystallization by evaporating the solvent and triturating with methanol as crystalline powder (330 mg).

N.M.R. δ ppm (CDCl$_3$)

2.40 (3H, s), 3.65 (6H, s), 4.81 (2H, d, J=5 Hz) 5.11 (1H, s), 7.25–8.13 (6H, m)

(8) To a cold mixture of 2-benzyloxyethyl 2-methyl-4-(3-nitrophenyl)-5-ethoxycarboxyl-6-formyl-1,4-dihydropyridine-3-carboxylate (2.0 g) in ethanol (40 ml) was added portionwise sodium borohydride (84.1 g) at −5° C. over 3 minutes with stirring. After 35 minutes, additional sodium borohydride (8.4 mg) was added and the mixture was stirred for further 10 minutes at −2° C. The reaction mixture was adjusted to pH 5 to 6 with 50% aqueous acetic acid and ethanol was distilled off under reduced pressure. The residual mixture was diluted with water (100 ml) and extracted with ethyl acetate. The extract was washed with water, dried over magnesium sulfate, and evaporated to dryness under reduced pressure to give an oil which was crystallized by keeping in a refrigerator overnight. The crystals were washed with n-hexane to give crystals (1.6 g) which were recrystallized from a mixture (12 ml) of diisopropyl ether and ethanol (1:1, v/v) to give pure crystals of 2-benzyloxyethyl 2-methyl-4-(3-nitrophenyl)-5-ethoxycarbonyl-6-hydroxymethyl-1,4-dihydropyridine-3-carboxylate (860 mg), m.p. 114.5° to 115.5° C. A second crop was recovered from the mother liquor in a usual manner to yield 220 mg, m.p. 112° to 114° C.

N.M.R. δ ppm (CDCl$_3$)

1.20 (3H, t, J=7 Hz), 2.75 (3H, s), 3.65 (2H, t, J=3 Hz), 4.15 (2H, q, J=7 Hz), 4.24 (2H, t, J=3 Hz), 4.51 (2H, s), 4.78 (2H, broad s), 5.13 (1H, s), 7.20–8.13 (9H, m)

EXAMPLE 15

(1) A mixture of methyl 4,4-dimethoxy-2-(3-nitrobenzylidene)acetoacetate (8.0 g) and isopropyl 3-aminocrotonate (4.07 g) was heated at 70° C. for an hour with stirring, and the stirring was continued at 100° C. for an hour and at 120° C. for additional 2.5 hours. After dissolving the reaction mixture in ethyl acetate, the solution was washed with water and an aqueous solution of sodium chloride, dried over magnesium sulfate and then evaporated to dryness under reduced pressure to give a yellow-orange oil (11.03 g) of isopropyl ester of 5-methoxycarbonyl-6-dimethoxymethyl-2-methyl-4-(3-nitrophenyl)-1,4-dihydropyridine-3-carboxylic acid.

| N.M.R. | δppm(CDCl$_3$): | 1.13 (d, J=7.0Hz)<br>1.27 (d, J=7.0Hz) | (6H) |
|---|---|---|---|
| | 2.40 (3H, s), | 3.47 (s)<br>3.50 (s) | (6H), |

3.69 (3H, s), 5.0 (1H, heptet, J=7.0 Hz), 5.17 (1H, s), 6.04 (1H, s), 6.92 (1H, broad s), 7.2–8.2 (4H, m).

(2) Isopropyl ester of 5-methoxycarbonyl-6-dimethoxymethyl-2-methyl-4-phenyl-1,4-dihydropyridine-3-carboxylic acid was prepared by reacting methyl 2-benzylidene-4,4-dimethoxyacetoacetate, which was obtained from benzaldehyde and methyl 4,4-dimethoxyacetoacetate according to the same manner as that of Preparation 1, with isopropyl 3-aminocrotonate in substantially the same manner as that of Example 15-(1).

N.M.R. δppm (CDCl₃): 1.11 (3H, d, J=6.5 Hz), 1.23 (3H, d, J=6.5 Hz), 2.37 (3H, s), 3.42 (3H, s), 3.46 (3H, s), 4.96 (1H, heptet, J=6.5 Hz), 5.03 (1H, s), 6.03 (1H, s), 6.73 (1H, s), 7.0–7.4 (5H, m).

The following examples are prepared in substantially the same manner as that of Example 15-(1).

(3) Isopropyl ester of 5-methoxycarbonyl-6-dimethoxymethyl-2-methyl-4-(2-tolyl)-1,4-dihydropyridine-3-carboxylic acid.

N.M.R. δppm (CDCl₃): 1.07 (3H, d, J=6.5 Hz), 1.21 (3H, d, J=6.5 Hz), 2.32 (3H, s), 2.55 (3H, s), 3.41 (3H, s), 3.44 (3H, s), 3.62 (3H, s), 4.96 (1H, heptet, J=6.5 Hz), 5.20 (1H, s), 5.97 (1H, s), 6.65 (1H, s), 6.9–7.4 (4H, m).

(4) Isopropyl ester of 5-methoxycarbonyl-6-dimethoxymethyl-2-methyl-4-(4-pyridyl)-1,4-dihydropyridine-3-carboxylic acid, mp 115°–117° C.

(5) Isopropyl ester of 4-(2-chlorophenyl)-5-methoxycarbonyl-6-dimethoxymethyl-2-methyl-1,4-dihydropyridine-3-carboxylic acid, mp 86°–87.5° C.

(6) Isopropyl ester of 4-(2-trifluoromethylphenyl)-5-methoxycarbonyl-6-dimethoxymethyl-2-methyl-1,4-dihydropyridine-3-carboxylic acid, mp 92°–94° C.

(7) Isopropyl ester of 5-methoxycarbonyl-6-dimethoxymethyl-4-(2-methoxyphenyl)-2-methyl-1,4-dihydropyridine-3-carboxylic acid, mp 110°–111.5° C.

(8) Isopropyl ester of 4-(2-allyloxyphenyl)-5-methoxycarbonyl-6-dimethoxymethyl-2-methyl-1,4-dihydropyridine-3-carboxylic acid.

N.M.R. δppm (CDCl₃): 1.01 (3H, d, J=6.5 Hz), 1.21 (3H, d, J=6.5 Hz), 2.33 (3H, s), 3.46 (6H, s), 3.63 (3H, s), 4.4–6.3 (8H, m), 6.60 (1H, broad s), 6.7–7.5 (4H, m).

(9) Isopropyl ester of 5-methoxycarbonyl-6-dimethoxymethyl-4-(2-thienyl)-1,4-dihydropyridine-3-carboxylic acid.

N.M.R. δppm (CDCl₃): 1.22 (3H, d, J=6.5 Hz), 1.28 (3H, d, J=6.5 Hz), 2.37 (3H, s), 3.43 (3H, s), 3.49 (3H, s), 3.76 (3H, s), 5.07 (1H, heptet, J=6.5 Hz), 5.38 (1H, s), 6.04 (1H, s), 6.65–7.45 (4H, m).

(10) Isopropyl ester of 4-(2,4-dichlorophenyl)-5-methoxycarbonyl-6-dimethoxymethyl-2-methyl-1,4-dihydropyridine-3-carboxylic acid.

N.M.R. δppm (CDCl₃): 1.07 (3H, d, J=6.5 Hz), 1.21 (3H, d, J=6.5 Hz), 2.34 (3H, s), 3.42 (3H, s), 3.46 (3H, s), 3.64 (3H, s), 4.97 (1H, heptet, J=6.5 Hz), 5.39 (1H, s), 5.96 (1H, s), 6.65 (1H, s), 7.0–7.4 (3H, m).

(11) Isopropyl ester of 4-(3,4-dichlorophenyl)-5-methoxycarbonyl-6-dimethoxymethyl-2-methyl-1,4-dihydropyridine-3-carboxylic acid.

N.M.R. δppm (CDCl₃): 1.18 (d, J=6.5Hz), 1.25 (d, J=6.5Hz) } (6H), 2.39 (3H, s), 3.46 (3H, s), 3.50 (3H, s), 3.70 (3H, s), 5.00 (1H, s), 5.00 (1H, heptet, J=6.5 Hz), 6.03 (1H, s), 6.75 (1H, s), 7.0–7.5 (3H, m).

(12) Isopropyl ester of 5-methoxycarbonyl-6-dimethoxymethyl-4-(3,4-dimethoxyphenyl)-2-methyl-1,4-dihydropyridine-3-carboxylic acid.

N.M.R. δppm (CDCl₃): 1.16 (3H, d, J=6.5 Hz), 1.25 (3H, d, J=6.5 Hz), 2.37 (3H, s), 3.41 (s), 3.43 (s), 3.45 (s), 3.49 (s) } (6H), 3.79 (3H, s), 3.84 (6H, s), 4.99 (1H, s), 4.99 (1H, heptet, J=6.5 Hz), 6.03 (1H, s), 6.6–7.3 (4H, m).

(13) Dipropyl ester of 2-methyl-4-(3-nitrophenyl)-6-dipropoxymethyl-1,4-dihydropyridine-3,5-dicarboxylic acid.

N.M.R. δppm (CDCl₃): 2.37 (3H, s), 5.02 (1H, s), 6.21 (1H, s), 6.88 (1H, broad s).

(14) 2-(N-Benzyl-N-methylamino)ethyl ester of 5-ethoxycarbonyl-6-diethoxymethyl-4-(2-trifluoromethylphenyl)-2-methyl-1,4-dihydropyridine-3-carboxylic acid.

N.M.R. δppm (CDCl₃): 1.1–1.3 (9H, m), 2.17 (3H, s), 2.33 (3H, s), 2.60 (2H, t, J=6 Hz), 3.48 (2H, s), 3.4–4.4 (8H, m), 5.63 (1H, s), 6.13 (1H, s), 6.71 (1H, s), 7.1–7.6 (9H, m).

(15) 2-Phenoxyethyl ester of 5-ethoxycarbonyl-6-diethoxymethyl-4-(2-trifluoromethylphenyl)-2-methyl-1,4-dihydropyridine-3-carboxylic acid.

N.M.R. δppm (CDCl₃): 1.0 to 1.5 (9H, m), 2.37 (3H, s), 3.5–4.6 (10H, m), 5.67 (1H, s), 7.12 (1H, s), 6.7–7.8 (10H, m).

(16) 2-Chloroethyl ester of 5-ethoxycarbonyl-6-diethoxymethyl-4-(2-trifluoromethylphenyl)-2-methyl-1,4-dihydropyridine-3-carboxylic acid.

N.M.R. δppm (CCl₄): 1.0–1.5 (6H, m), 2.39 (3H, s), 3.4–4.5 (10H, m), 5.5–5.7 (1H, m), 6.10 (1H, s), 6.55 (1H, s), 7–7.6 (4H, m).

(17) 2-Ethoxyethyl ester of 5-ethoxycarbonyl-6-diethoxymethyl-4-(2-trifluoromethylphenyl)-2-methyl-1,4-dihydropyridine-3-carboxylic acid.

N.M.R. δppm (CCl₄): 1.0–1.4 (12H, m), 2.38 (3H, s), 3.3–4.3 (12H, m), 5.5–5.7 (1H, m), 6.10 (1H, s), 6.47 (1H, s), 7.2–7.7 (4H, m).

(18) 2-Benzyloxyethyl ester of 5-ethoxycarbonyl-6-diethoxymethyl-4-(2-trifluoromethylphenyl)-2-methyl-1,4-dihydropyridine-3-carboxylic acid.

N.M.R. δppm (CDCl₃): 1.0–1.6 (9H, m), 2.32 (3H, s), 3.4–4.4 (10H, m), 4.47 (2H, s), 5.6–5.7 (1H, m), 6.11 (1H, s), 6.6–6.8 (1H, broad s), 7.2–7.7 (9H, m).

EXAMPLE 16

(1) A mixture of 2-phenoxyethyl ester of 2-(2-trifluoromethylbenzylidene)acetoacetate (19.62 g) and ethyl 2-amino-4,4-diethoxycrotonate (11.95 g) was heated for 20 hours at 100° to 110° C. and for additional 12 hours at 120° to 130° C. The resultant mixture was dissolved in ethyl acetate and washed with water and then dried over anhydrous magnesium sulfate. The solvent was removed by distillation to give a crude oil. (27.7 g), which was chromatographed over silica gel with a mixture of benzene and ethyl acetate (50:1 by volume) as an eluent to give 2-phenoxyethyl ester of 5-ethoxycarbonyl-6-diethoxymethyl-4-(2-trifluoromethylphenyl)-2-methyl-1,4-dihydropyridine-3-carboxylic acid (19.34 g).

N.M.R. δppm (CDCl₃): 1.0 to 1.5 (9H, m), 2.37 (3H, s), 3.5–4.6 (10H, m), 5.67 (1H, s), 7.12 (1H, 6.7–7.8 (10H, m).

The following compounds were obtained in substantially the same manner as that of Example 16-(1).

(2) 2-Chloroethyl ester of 5-ethoxycarbonyl-6-diethoxymethyl-4-(2-trifluoromethylphenyl)-2-methyl-1,4-dihydropyridine-3-carboxylic acid.

N.M.R. δppm (CCl4): 1.0–1.5 (6H, m), 2.39 (3H, s), 3.4–4.5 (10H, m), 5.5–5.7 (1H, m), 6.10 (1H, s), 6.55 (1H, s), 7–7.6 (4H, m).

(3) 2-Ethoxyethyl ester of 5-ethoxycarbonyl-6-diethoxymethyl-4-(2-trifluoromethylphenyl)-2-methyl-1,4-dihydropyridine-3-carboxylic acid.

N.M.R. δppm (CCl4): 1.0–1.4 (12H, m), 2.38 (3H, s), 3.3–4.3 (12H, m), 5.5–5.7 (1H, m), 6.10 (1H, s), 6.47 (1H, s), 7.2–7.7 (4H, m).

(4) 2-Benzyloxyethyl ester of 5-ethoxycarbonyl-6-diethoxymethyl-4-(2-trifluoromethylphenyl)-2-methyl-1,4-dihydropyridine-3-carboxylic acid.

N.M.R. δppm (CDCl$_3$): 1.0–1.6 (9H, m), 2.32 (3H, s), 3.4–4.4 (10H, m), 4.47 (2H, s), 5.6–5.7 (1H, m), 6.11 (1H, s), 6.6–6.8 (1H, broad s), 7.2–7.7 (9H, m)

(5) 2-(N-Benzyl-N-methylamino)ethyl ester of 5-ethoxycarbonyl -6-diethoxymethyl-4-(2-trifluoromethylphenyl)-2-methyl-1,4-dihydropyridine-3-carboxylic acid.

N.M.R. δppm (CDCl$_3$): 1.1–1.3 (9H, m), 2.17 (3H, s), 2.33 (3H, s), 2.60 (2H, t, J=6 Hz), 3.48 (2H, s), 3.4–4.4 (8H, m), 5.63 (1H, s), 6.13 (1H, s), 6.71 (1H, s), 7.1–7.6 (9H, m).

(6) Isopropyl ester of 5-methoxycarbonyl-6-dimethoxymethyl-2-methyl-4-(3-nitrophenyl)-1,4-dihydropyridine-3-carboxylic acid.

N.M.R. δppm (CDCl$_3$): 1.13 (d, J=7.0 Hz) 1.27 (d, J=7.0 Hz)

$$\left.\begin{array}{l}2.40\ (3H,\ s),\ 3.47\ (s)\\ 3.50\ (s)\end{array}\right\}\ (6H),$$

3.69 (3H, s), 5.0 (1H, heptet, J=7.0 Hz), 5.17 (1H, s), 6.04 (1H, s), 6.92 (1H, broad s), 7.2–8.2 (4H, m).

(7) Isopropyl ester of 5-methoxycarbonyl-6-dimethoxymethyl-2-methyl-4-phenyl-1,4-dihydropyridine-3-carboxylic acid.

N.M.R. δppm (CDCl$_3$): 1.11 (3H, d, J=6.5 Hz), 1.23 (3H, d, J=6.5 Hz), 2.37 (3H, s), 3.42 (3H, s), 3.46 (3H, s), 4.96 (1H, heptet, J=6.5 Hz), 5.03 (1H, s), 6.03 (1H, s), 6.73 (1H, s), 7.0–7.4 (5H, m).

(8) Isopropyl ester of 5-methoxycarbonyl-6-dimethoxymethyl-2-methyl-4-(2-tolyl)-1,4-dihydropyridine-3-carboxylic acid.

N.M.R. δppm (CDCl$_3$): 1.07 (3H, d, J=6.5 Hz), 1.21 (3H, d, J=6.5 Hz), 2.32 (3H, s), 2.55 (3H, s), 3.41 (3H, s), 3.44 (3H, s), 3.62 (3H, s), 4.96 (1H, heptet, J=6.5 Hz), 5.20 (1H, s), 5.97 (1H, s), 6.65 (1H, s), 6.9–7.4 (4H, m).

(9) Isopropyl ester of 5-methoxycarbonyl-6-dimethoxymethyl-2-methyl-4-(4-pyridyl)-1,4-dihydropyridine-3-carboxylic acid.

I.R. νNujol/max: 3300, 3200, 3070, 1710 (shoulder), 1700, 1650, 1603, 1518, 1278, 1269, 1190, 1090, 960, 782 cm$^{-1}$

(10) Isopropyl ester of 4-(2-chlorophenyl)-5-methoxycarbonyl-6dimethoxymethyl-2-methyl-1,4-dihydropyridine-3-carboxylic acid, mp 86°–87.5° C.

(11) Isopropyl ester of 4-(2-trifluoromethylphenyl)-5-methoxycarbonyl-6-dimethoxymethyl-2-methyl-1,4-dihydropyridine-3-carboxylic acid.

I.R. νNujol/max: 3400, 1720, 1690, 1653, 1493, 1319, 1310, 1278, 1206, 1095, 1035, 951, 768 cm$^{-1}$.

(12) Isopropyl ester of 5-methoxycarbonyl-6-dimethoxymethyl-4-(2-methoxyphenyl)-2-methyl-1,4-dihydropyridine-3-carboxylic acid, mp 110–111.5° C.

(13) Isopropyl ester of 4-(2-allyloxyphenyl)-5-methoxycarbonyl-6-dimethoxymethyl-2-methyl-1,4-dihydropyridine-3-carboxylic acid.

N.M.R. δppm (CDCl$_3$): 1.01 (3H, d, J=6.5 Hz), 1.21 (3H, d, J=6.5 Hz), 2.33 (3H, s), 3.46 (6H, s), 3.63 (3H, s), 4.4–6.3 (8H, m), 6.60 (1H, broad s), 6.7–7.5 (4H, m)

(14) Isopropyl ester of 5-methoxycarbonyl-6-dimethoxymethyl-2-methyl-4-(2-thienyl)-1,4-dihydropyridine-3-carboxylic acid.

N.M.R. δppm (CDCl$_3$): 1.22 (3H, d, J=6.5 Hz), 1.28 (3H, d, J=6.5 Hz), 2.37 (3H, s), 3.43 (3H, s), 3.49 (3H, s), 3.76 (3H, s), 5.07 (1H, heptet, J=6.5 Hz), 5.38 (1H, s), 6.04 (1H, s), 6.65–7.45 (4H, m).

(15) Isopropyl ester of 4-(2,4-dichlorophenyl)-5-methoxycarbonyl-6-dimethoxymethyl-2-methyl-1,4-dihydropyridine-3-carboxylic acid.

N.M.R. δppm, (CDCl$_3$): 1.07 (3H, d, J=6.5 Hz), 1.21 (3H, d, J=6.5 Hz), 2.34 (3H, s), 3.42 (3H, s), 3.46 (3H, s), 3.64 (3H, s), 4.97 (1H, heptet, J=6.5 Hz), 5.39 (1H, s), 5.96 (1H, s), 6.65 (1H, s), 7.0–7.4 (3H, m)

(16) Isopropyl ester of 4-(3,4-dichlorophenyl)-5-methoxycarbonyl-6-dimethoxymethyl-2-methyl-1,4-dihydropyridine-3-carboxylic acid.

N.M.R. δppm (CDCl$_3$): 1.18 (d, J=6.5 Hz)) (6H), 1.25 (d, J=6.5 Hz) 2.39 (3H, s), 3.46 (3H, s), 3.50 (3H, s), 3.70 (3H, s), 5.00 (1H, s), 5.00 (1H, heptet, J=6.5 Hz), 6.03 (1H, s), 6.75 (1H, s), 7.0–7.5 (3H, m).

(17) Isopropyl ester of 5-methoxycarbonyl-6-dimethoxymethyl-4-(3,4-dimethoxyphenyl)-2-methyl-1,4-dihydropyridine-3-carboxylic acid.

N.M.R. δppm (CDCl$_3$): 1.16 (3H, d, J=6.5 Hz), 1.25 (3H, d, J=6.5 Hz), 2.37 (3H, s), $$\left.\begin{array}{l}3.41\ (s)\\ 3.43\ (s)\\ 3.45\ (s)\\ 3.49\ (s)\end{array}\right\}\ (6H),$$

3.79 (3H, s), 3.84 (6H, s), 4.99 (1H, s), 4.99 (1H, heptet, J=6.5 Hz), 6.03 (1H, s), 6.6–7.3 (4H, m).

(18) Dipropyl ester of 2-methyl-4-(3-nitrophenyl)-6-dipropoxymethyl-1,4-dihydropyridine-3,5-dicarboxylic acid.

N.M.R. δppm (CDCl$_3$): 2.37 (3H, s), 5.02 (1H, s), 6.21 (1H, s), 6.88 (1H, broad s).

EXAMPLE 17

(1) To a solution of 2-phenoxyethyl ester of 5-ethoxycarbonyl-6-diethoxymethyl-4-(2-trifluoromethylphenyl)-2-methyl-1,4-dihydropyridine-3-carboxylic acid (15.85 g) in acetone (159 ml) was added 6 N hydrochloric acid (15.85 ml) at ambient temperature with stirring and the stirring was continued for 1.5 hours. The reaction mixture was neutralized with a saturated aqueous solution of sodium bicarbonate, and the acetone was removed in vacuo. The residue was dissolved in ethyl acetate, washed with water and then dried. Removal of the solvent gave an oil (13.56 g) of 2-phenoxyethyl ester of 5-ethoxycarbonyl-4-(2-trifluoromethylphenyl)-6-formyl-2-methyl-1,4-dihydropyridine-3-carboxylic acid.

N.M.R. δppm (CDCl₃): 1.22 (3H, t, J=7.5 Hz), 2.40 (3H, s), 4.0-4.6 (6H, m), 5.71 (1H, s), 6.7-7.7 (10H, m), 10.26 (1H, s).

The following compounds were prepared in substantially the same manner as that of Example 17-(1).

(2) Isopropyl ester of 6-formyl-5-methoxycarbonyl-2-methyl-4-phenyl-1,4-dihydropyridine-3-carboxylic acid.

(3) Isopropyl ester of 6-formyl-5-methoxycarbonyl-2-methyl-4-(2-tolyl)-1,4-dihydropyridine-3-carboxylic acid, mp 143°-144° C.

(4) Isopropyl ester of 6-formyl-5-methoxycarbonyl-2-methyl-4-(4-pyridyl)-1,4-dihydropyridine-3-carboxylic acid, mp 143°-145° C.

(5) Isopropyl ester of 4-(2-chlorophenyl)-6-formyl-5-methoxycarbonyl-2-methyl-1,4-dihydropyridine-3-carboxylic acid, mp 102°-103° C.

(6) Isopropyl ester of 4-(2-trifluoromethylphenyl)-6-formyl-5-methoxycarbonyl-2-methyl-1,4-dihydropyridine-3-carboxylic acid, mp 83°-85° C.

(7) Isopropyl ester of 6-formyl-5-methoxycarbonyl-4-(2-methoxyphenyl)-2-methyl-1,4-dihydropyridine-3-carboxylic acid, mp 142°-143° C.

(8) Isopropyl ester of 4-(2-allyloxyphenyl)-6-formyl-5-methoxycarbonyl-2-methyl-1,4-dihydropyridine-3-carboxylic acid, mp 103°-104.5° C.

(9) Isopropyl ester of 6-formyl-5-methoxycarbonyl-2-methyl-4-(2-thienyl)-1,4-dihydropyridine-3-carboxylic acid, mp 114°-116° C.

(10) Isopropyl ester of 4-(2,4-dichlorophenyl)-6-formyl-5-methoxycarbonyl-2-methyl-1,4-dihydropyridine-3-carboxylic acid.

N.M.R. δppm (CDCl₃): 1.07 (3H, d, J=6.5 Hz), 1.24 (3H, d, J=6.5 Hz), 2.39 (3H, s), 3.71 (3H, s), 4.98 (1H, heptet, J=6.5 Hz), 5.51 (1H, s), 6.93 (1H, s), 7.0-7.4 (3H, m), 10.34 (1H, s).

(11) Isopropyl ester of 4-(3,4-dichlorophenyl)-6-formyl-5-methoxycarbonyl-2-methyl-1,4-dihydropyridine-3-carboxylic acid, mp 95°-96° C.

(12) Isopropyl ester of 6-formyl-5-methoxycarbonyl-4-(3,4dimethoxyphenyl)-2-methyl-1,4-dihydropyridine-3-carboxylic acid.

N.M.R. δppm (CDCl₃): 1.14 (3H, d, J=6.5 Hz), 1.26 (3H, d, J=6.5 Hz), 2.40 (3H, s), 3.78 (3H, s), 3.84 (6H, s), 4.98 (1H, heptet, J=6.5 Hz), 5.05 (1H, s), 6.5-37. (4H, m), 10.44 (1H, s).

(13) Dipropyl ester of 6-formyl-2-methyl-4-(3-nitrophenyl)-1,4-dihydropyridine-3,5-dicarboxylic acid.

N.M.R. δppm (CDCl₃): 0.87 (3H, t, J=7.5 Hz), 0.90 (3H, t, J=7.5 Hz), 1.55 (2H, sixtet, J=7.5 Hz), 1.61 (2H, sixtet, J=7.5 Hz), 2.44 (3H, s), 4.02 (2H, t, J=7.5 Hz), 4.13 (2H, t, J=7.5 Hz),
5.28 (1H, s), 7.11 (1H, broad s), 7.4-8.2 (4H, m), 10.56 (1H, s).

(14) 2-Hydroxyethyl ester of 5-ethoxycarbonyl-6-formyl-2-methyl-4-(3-nitrophenyl)-1,4-dihydropyridine-3-carboxylic acid.

N.M.R. δppm (CDCl₃): 5.25 (1H, s), 10.50 (1H, s).

(15) Isopropyl ester of 6-formyl-5-methoxycarbonyl-2-methyl-4-(3-nitrophenyl)-1,4-dihydropyridine-3-carboxylic acid.

N.M.R. δppm (CDCl₃): 1.22 (3H, t, J=7.5 Hz), 2.40 (3H, s) 4.0 to 4.6 (6H, m), 5.71 (1H, s), 6.7 to 7.7 (10H, m), 10.26 (1H, s)

(16) 2-Ethoxyethyl ester of 5-ethoxycarbonyl-6-formyl-4-(2-trifluoromethylphenyl)-2-methyl-1,4-dihydropyridine-3-carboxylic acid.

N.M.R. δppm (CDCl₃): 1.14 (t, J=7 Hz)) (6H), 1.26 (t, J=7 Hz) 2.43 (3H, s), 3.3-3.8 (4H, m), 4.0-4.5 (4H, m), 5.7-5.8 (1H, m), 6.8-7.0 (1H, m), 7.1-7.8 (4H, m), 10.27 (1H, s).

(17) 2-Benzyloxyethyl ester of 5-ethoxycarbonyl-6-formyl-4-(2-trifluoromethylphenyl)-2-methyl-1,4-dihydropyridine-3-carboxylic acid.

N.M.R. δppm (CCl₄): 1.23 (3H, t, J=7.5 Hz), 2.40 (3H, s), 3.4-4.5 (6H, m), 4.41 (2H, s), 5.7-5.8 (1H, m), 6.8-6.9 (1H, m) 7.2-7.8 (9H, m), 10.28 (1H, s).

(18) 2-[N-Benzyl-N-methylamino]ethyl ester of 5-ethoxycarbonyl-6-formyl-4-(2-trifluoromethylphenyl)-2-methyl-1,4-dihydropyridine-3-carboxylic acid.

N.M.R. δppm (CDCl₃): 1.23 (3H, t, J=7 Hz), 2.19 (3H, s), 2.41 (3H, s), 2.63 (2H, t, J=7 Hz), 3.51 (2H, s), 4-4.4 (4H, m), 5.71 (1H, broad s), 6.91 (1H, broad s), 7.2-7.7 (9H, m), 10.28 (1H, s).

EXAMPLE 18

(1) To a solution of isopropyl ester of 6-formyl-5-methoxycarbonyl-2-methyl-4-(3-nitrophenyl)-1,4-dihydropyridine-3-carboxylate (4.2 g) in ethanol (85 ml) was gradually added portionwise sodium borohydride (0.409 g) over a period of 35 minutes under cooling below 0° C. with stirring. After the reaction mixture was acidified with 50% aqueous solution of acetic acid, the ethanol was removed under reduced pressure. To the resultant aqueous suspension was diluted with water and the precipitated pale-yellowish powder was collected by filtration, washed with water and dried. This powder (3.89 g) was recrystallized with ethanol to give a yellow powder (3.05 g) of isopropyl ester of 6-hydroxymethyl-5-methoxycarbonyl-2-methyl-4-(3-nitrophenyl)-1,4-dihydropyridine-3-carboxylic acid, mp 164°-166° C.

The following compounds were prepared in substantially the same manner as that of Example 18-(1).

(2) Isopropyl ester of 6-hydroxymethyl-5-methoxycarbonyl-2-methyl-4-phenyl-1,4-dihydropyridine-3-carboxylic acid, mp 132°-133° C.

(3) Isopropyl ester of 6-hydroxymethyl-5-methoxycarbonyl-2-methyl-4-(2-tolyl)-1,4-dihydropyridine-3-carboxylic acid, mp 134°-135.5° C.

(4) Isopropyl ester of 6-hydroxymethyl-5-methoxycarbonyl-2-methyl-4-(4-pyridyl)-1,4-dihydropyridine-3-carboxylic acid, mp 182°-183° C. (dec.).

(5) Isopropyl ester of 4-(2-chlorophenyl)-6-hydroxymethyl-5-methoxycarbonyl-2-methyl-1,4-dihydropyridine-3-carboxylic acid, mp 122°-123° C.

(6) Isopropyl ester of 4-(2-trifluoromethylphenyl)-6-hydroxymethyl-5-methoxycarbonyl-2-methyl-1,4-dihydropyridine-3-carboxylic acid, mp 123°-125° C.

(7) Isopropyl ester of 6-hydroxymethyl-5-methoxycarbonyl-4-(2-methoxyphenyl)-2-methyl-1,4-dihydropyridine-3-carboxylic acid, mp 142°-143° C.

(8) Isopropyl ester of 4-(2-allyloxyphenyl)-6-hydroxymethyl-5-methoxycarbonyl-2-methyl-1,4-dihydropyridine-3-carboxylic acid, mp 124°-125° C.

(9) Isopropyl ester of 6-hydroxymethyl-5-methoxycarbonyl-2-methyl-4-(2-thienyl)-1,4-dihydropyridine-3-carboxylic acid, mp 124.5°-126° C.

(10) Isopropyl ester of 4-(2,4-dichlorophenyl)-6-hydroxymethyl-5-methoxycarbonyl-2-methyl-1,4-dihydropyridine-3-carboxylic acid, mp 150°-151° C.

(11) Isopropyl ester of 4-(3,4-dichlorophenyl)-6-hydroxymethyl-5-methoxycarbonyl-2-methyl-1,4-dihydropyridine-3-carboxylic acid, mp 122°-123° C.

(12) Isopropyl ester of 6-hydroxymethyl-5-methoxycarbonyl-4-(3,4-dimethoxyphenyl)-2-methyl-1,4-dihydropyridine-3-carboxylic acid, mp 123°–124° C.

(13) Dipropyl ester of 6-hydroxymethyl-2-methyl-4-(3-nitrophenyl)-1,4-dihydropyridine-3,5-dicarboxylic acid, mp 118°–120° C.

(14) 2-Phenoxyethyl ester of 5-ethoxycarbonyl-4-(2-trifluoromethylphenyl)-6-hydroxymethyl-2-methyl-1,4-dihydropyridine-3-carboxylic acid, mp 148°–149° C.

(15) 2-Ethoxyethyl ester of 5-ethoxycarbonyl-4-(2-trifluoromethylphenyl)-6-hydroxymethyl-2-methyl-1,4-dihydropyridine-3-carboxylic acid, mp 65°–66.5° C.

(16) 2-Benzyloxyethyl ester of 5-ethoxycarbonyl-4-(2-trifluoromethylphenyl)-6-hydroxymethyl-2-methyl-1,4-dihydropyridine-3-carboxylic acid, mp 104°–106° C.

EXAMPLE 19

(1) To a solution of isopropyl ester of 6-formyl-5-methoxycarbonyl-2-methyl-4-(3-nitrophenyl)-1,4-dihydropyridine-3-carboxylic acid (4.5 g) in acetic acid (35 ml) were added hydroxylamine hydrochloride (0.97 g) and sodium acetate (1.43 g), and the mixture was stirred at ambient temperature for 2.5 hours. After acetic anhydride (4.14 g) was added to this reaction mixture, the mixture was stirred at ambient temperature for 1.5 hours and at 95°–100° C. for additional 4 hours. The acetic acid and the excess of acetic anhydride were removed in vacuo, followed by adding water to the residue and it was neutralized with a saturated aqueous solution of sodium bicarbonate. This aqueous suspension was extracted twice with ethyl acetate, and the combined extract was washed with water, dried over anhydrous magnesium sulfate and evaporated to dryness under reduced pressure to give a reddish-brown oil (4.88 g), which was chromatographed over silica gel (150 g) with a mixture of benzene and ethyl acetate (10:1 by volume) as an eluent to give a crude crystals (2.99 g). These were recrystallized from ethanol to give yellow prisms (1.89 g) of isopropyl ester of 6-cyano-5-methoxycarbonyl-2-methyl-4-(3-nitrophenyl)-1,4-dihydropyridine-3-carboxylic acid, mp 148°–150° C.

The following compounds were prepared in substantially the same manner as that of Example 19-(1).

(2) Isopropyl ester of 6-cyano-5-methoxycarbonyl-2-methyl-4-phenyl-1,4-dihydropyridine-3-carboxylic acid, mp 130°–131° C.

(3) Isopropyl ester of 6-cyano-5-methoxycarbonyl-2-methyl-4-(2-tolyl)-1,4-dihydropyridine-3-carboxylic acid, mp 147°–149° C.

(4) Isopropyl ester of 6-cyano-5-methoxycarbonyl-2-methyl-4-(4-pyridyl)-1,4-dihydropyridine-3-carboxylic acid, mp 192°–195° C. (dec.).

(5) Isopropyl ester of 4-(2-chlorophenyl)-6-cyano-5-methoxycarbonyl-2-methyl-1,4-dihydropyridine-3-carboxylic acid, mp 176°–177° C.

(6) Isopropyl ester of 6-cyano-4-(2-trifluoromethylphenyl)-5-methoxycarbonyl-2-methyl-1,4-dihydropyridine-3-carboxylic acid, mp 172°–173° C.

(7) Isopropyl ester of 6-cyano-5-methoxycarbonyl-4-(2-methoxyphenyl)-2-methyl-1,4-dihydropyridine-3-carboxylic acid, mp 139°–140° C.

(8) Isopropyl ester of 4-(2-allyloxyphenyl)-6-cyano-5-methoxycarbonyl-2-methyl-1,4-dihydropyridine-3-carboxylic acid, mp 115°–116° C.

(9) Isopropyl ester of 6-cyano-5-methoxycarbonyl-2-methyl-4-(2-thienyl)-1,4-dihydropyridine-3-carboxylic acid, mp 129°–131° C.

(10) Isopropyl ester of 4-(2,4-dichlorophenyl)-6-cyano-5-methoxycarbonyl-2-methyl-1,4-dihydropyridine-3-carboxylic acid, mp 141°–142° C.

(11) Isopropyl ester of 4-(3,4-dichlorophenyl)-6-cyano-5-methoxycarbonyl-2-methyl-1,4-dihydropyridine-3-carboxylic acid, mp 159°–160° C.

(12) Isopropyl ester of 6-cyano-5-methoxycarbonyl-4-(3,4-dimethoxyphenyl)-2-methyl-1,4-dihydropyridine-3-carboxylic acid, mp 124.5°–125.5° C.

(13) Dipropyl ester of 6-cyano-2-methyl-4-(3-nitrophenyl)-1,4-dihydropyridine-3,5-dicarboxylic acid, mp 138°–140° C.

(14) 2-Phenoxyethyl ester of 6-cyano-5-ethoxycarbonyl-4-(2-trifluoromethylphenyl)-2-methyl-1,4-dihydropyridine-3-carboxylic acid, mp 118°–119° C.

(15) 2-Hydroxyethyl ester of 6-cyano-5-ethoxycarbonyl-2-methyl-4-(3-nitrophenyl)-1,4-dihydropyridine-3-carboxylic acid, mp 150.5°–152° C.

(16) 2-Ethoxyethyl ester of 6-cyano-5-ethoxycarbonyl-4-(2-trifluoromethylphenyl)-2-methyl-1,4-dihydropyridine-3-carboxylic acid, mp 104°–105° C.

(17) 2-Benzyloxyethyl ester of 6-cyano-5-ethoxycarbonyl-4-(2-trifluoromethylphenyl)-2-methyl-1,4-dihydropyridine-3-carboxylic acid, mp 146°–147.5° C.

(18) 2-(N-Benzyl-N-methylamino)ethyl ester of 6-cyano-5-ethoxycarbonyl-4-(2-trifluoromethylphenyl)-2-methyl-1,4-dihydropyridine-3-carboxylic acid hydrochloride, mp 203°–204° C. (dec.)

EXAMPLE 20

To a solution of 2-acetoxyethyl ester of 6-cyano-5-ethoxycarbonyl-2-methyl-4-(3-nitrophenyl)-1,4-dihydropyridine-3-carboxylic acid (1.119 g) in ethanol (20 ml) was added dropwise an aqueous solution (5 ml) of potassium carbonate (0.346 g) under refluxing and stirring for 2 hours.

After cooling, the ethanol was removed in vacuo from the reaction mixture, followed by neutralizing with acetic acid and extracted twice with ethyl acetate. The combined extract was washed with diluted aqueous solution of sodium bicarbonate and an aqueous solution of sodium chloride, and then dried.

The solvent was removed in vacuo to give an oil, which was spontaneously crystallized to obtain crystals (0.94 g) of 2-hydroxyethyl ester of 6-cyano-5-ethoxycarbonyl-2-methyl-4-(3-nitrophenyl)-1,4-dihydropyridine-3-carboxylic acid, mp 150.5°–152° C.

EXAMPLE 21

A mixture of 2-chloroethyl ester of 5-ethoxycarbonyl-6-diethoxymethyl-4-(2-trifluoromethylphenyl)-2-methyl-1,4-dihydropyridine-3-carboxylic acid (5.20 g), N-methyl benzylamine (3.63 g) and sodium iodide (0.2 g) in propyl alcohol (10 ml) was heated under reflux for 4.5 hours. After the solvent was removed in vacuo from the reaction mixture, water and ethyl acetate were added to the residue. The ethyl acetate layer was separated, washed with water and then dried. Removal of the solvent gave a residual oil (6.98 g), which was chromatographed over silica gel (210 g) with a mixture of benzene and ethyl acetate (5:1 by volume) as an eluent to give an oil (3.67 g) of 2-(N-benzyl-N-methylamino)ethyl ester of 5-ethoxycarbonyl-6-diethoxymethyl-4-(2-trifluoromethylphenyl)-2-methyl-1,4-dihydropyridine-3-carboxylic acid.

N.M.R. δppm(CDCl$_3$): 1.1–1.3 (9H,m), 2.17 (3H,s), 2.33 (3H,s), 2.60 (2H,t,J=6 Hz), 3.48 (2H,s), 3.4–4.4

(8H,m), 5.63 (1H,s), 6.13 (1H,s), 6.71 (1H,s), 7.1–7.6 (9H,m).

EXAMPLE 22

(1) A mixture of methyl 2-(2-cyanobenzylidene)-4,4-dimethoxyacetoacetate (10.1 g) and isopropyl 3-aminocrotonate (5.51 g) was heated for 40 minutes at 78° C. and for 5.5 hours at 120° C. with stirring, followed by heating for an hour at 125° C. without the stirring. After the reaction mixture was allowed to stand overnight, it was dissolved in ethyl acetate. This solution was washed twice with water, dried and then evaporated to dryness under reduced pressure to give a residue, which was crystallized from ethyl ether. The crystals were collected by filtration and washed with a small amount of ethyl ether to give crude powder of isopropyl ester of 4-(2-cyanophenyl)-5-methoxycarbonyl-6-dimethoxymethyl-2-methyl-1,4-dihydropyridine-3-carboxylic acid (8.96 g). Further, the crude product (0.77 g) was recovered from the filtrate. 0.5 g Of this crude product was recrystallized from isopropyl ether to give purified white powder of the same product (0.37 g), mp 171°–172.5° C.

The following compound was obtained in the similar manner to that of Example 22-(1).

(2) Isopropyl ester of 5-methoxycarbonyl-4-(2-methoxycarbonylphenyl)-6-dimethoxymethyl-2-methyl-1,4-dihydropyridine-3-carboxylic acid.

N.M.R. $\delta$ppm (CDCl$_3$): 0.95 (3H, d, J=7 Hz), 1.19 (3H, d, J=7 Hz), 2.37 (3H, s), 3.40 (3H, s), 3.46 (3H, s), 3.61 (3H, s), 3.97 (3H, s), 4.97 (1H, heptet, J=7 Hz), 5.93 (1H, s), 6.05 (1H, s), 6.59 (1H, broad s), 7.0~7.9 (4H, m).

EXAMPLE 23

(1) A mixture of 2-chloroethyl 2-(2-cyanobenzylidene)acetoacetate (4.72 g) and ethyl 3-amino-4,4-diethoxycrotonate (4.06 g) was heated for 3 hours at 100°~105° C. with stirring. After cooling, the reaction mixture was dissolved in ethyl acetate, and the solution was washed twice with an aqueous solution of sodium chloride and then dried over magnesium sulfate. After removal of the solvent under reduced pressure, the residual oil was chromatographed over silica gel with a mixture of benzene and ethyl acetate (5:1 V/V) to give 2-chloroethyl ester of 4-(2-cyanophenyl)-5-ethoxycarbonyl-6-diethoxymethyl-2-methyl-1,4-dihydropyridine-3-carboxylic acid (5.81 g).

N.M.R. $\delta$ppm (CDCl$_3$): 1.1 to 1.4 (9H, m), 2.37 (3H, s), 3.4~3.95 (6H, m), 4.0~4.4 (4H, m), 5.39 (1H, s), 6.24 (1H, s), 6.90 (1H, broad s), 7.1~7.6 (4H, m)

The following compounds (2)~(5) were obtained in the similar manner to that of Example 23-(1).

(2) 2-(N-Benzyl-N-methylamino)ethyl ester of 4-(2-cyanophenyl)-5-ethoxycarbonyl-6-diethoxymethyl-2-methyl-1,4-dihydropyridine-3-carboxylic acid.

N.M.R. $\delta$ppm (CDCl$_3$): 1.1~1.5 (9H, m), 2.21 (3H, s), 2.40 (3H, s), 2.72 (2H, t, J=6 Hz), 3.53 (2H, s), 3.5~4.5 (8H, m), 5.44 (1H, s), 6.30 (1H, s), 6.87 (1H, broad s), 7.2~7.8 (9H, m)

(3) 2-Ethoxyethyl ester of 4-(2-cyanophenyl)-5-ethoxycarbonyl-6-diethoxymethyl-2-methyl-1,4-dihydropyridine-3-carboxylic acid.

N.M.R. $\delta$ppm (CDCl$_3$): 1.0~1.5 (12H, m), 2.42 (3H, s), 3.3~4.4 (12H, m), 5.45 (1H, s), 6.30 (1H, s), 6.87 (1H, s), 7.1~7.7 (4H, m)

(4) 2-Phenoxyethyl ester of 4-(2-cyanophenyl)-5-ethoxycarbonyl-6-diethoxymethyl-2-methyl-1,4-dihydropyridine-3-carboxylic acid, mp 94°~95° C.

(5) 2-Benzyloxyethyl ester of 4-(2-cyanophenyl)-5-ethoxycarbonyl-6-diethoxymethyl-2-methyl-1,4-dihydropyridine-3-carboxylic acid, mp 97.5°~98.5° C.

EXAMPLE 24

(1) A solution of isopropyl ester of 4-(2-cyanophenyl)-5-methoxycarbonyl-6-dimethoxymethyl-2-methyl-1,4-dihydropyridine-3-carboxylic acid (9.32 g) in 6 N hydrochloric acid (11 ml) and acetone (95 ml) was stirred for 5 hours at ambient temperature. The reaction mixture was neutralized with sodium bicarbonate and then the acetone was removed by distillation therefrom. To the resultant solution were poured water and ethyl acetate, and the ethyl acetate layer was separated, washed with water and an aqueous solution of sodium chloride, and then dried over magnesium sulfate. The ethyl acetate was removed by distillation under reduced pressure to give a solid, which was washed with a mixture of ethyl ether and hexane to provide crude yellowish-orange powder (7.65 g) of isopropyl ester of 4-(2-cyanophenyl)-6-formyl-5-methoxycarbonyl-2-methyl-1,4-dihydropyridine-3-carboxylic acid. 0.5 g Of this powder was recrystallized from isopropyl ether to give the purified yellowish-orange powder of the same product (0.34 g), mp 132°~134° C.

The following compounds (2)~(6) were obtained in the similar manner to that of Example 24-(1).

(2) Isopropyl ester of 6-formyl-5-methoxycarbonyl-4-(2-methoxycarbonylphenyl)-2-methyl-1,4-dihydropyridine-3-carboxylic acid N.M.R. $\delta$ppm (CDCl$_3$): 0.94 (d, J=6.5 Hz)} (6H) 1.19 (d, J=6.5 Hz) 2.41 (3H, s), 3.70 (3H, s), 3.97 (3H, s), 4.96 (1H, heptet, J=6.5 Hz), 6.21 (1H, s), 6.82 (1H, broad s), 7.0~7.9 (4H, m), 10.23 (1H, s)

(3) 2-(N-Benzyl-N-methylamino)ethyl ester of 4-(2-cyanophenyl)-5-ethoxycarbonyl-6-formyl-2-methyl-1,4-dihydropyridine-3-carboxylic acid.

N.M.R. $\delta$ppm (CDCl$_3$): 1.29 (3H, t, J=7.5 Hz), 2.21 (3H, s), 2.44 (3H, s), 2.71 (2H, t, J=6 Hz), 3.51 (2H, s), 4.1~4.4 (4H, m), 5.51 (1H, s), 7.04 (1H, broad s), 7.2~7.75 (9H, m), 10.57 (1H, s)

(4) 2-Ethoxyethyl ester of 4-(2-cyanophenyl)-5-ethoxycarbonyl-6-formyl-2-methyl-1,4-dihydropyridine-3-carboxylic acid, mp 115°~116° C.

(5) 2-Phenoxyethyl ester of 4-(2-cyanophenyl)-5-ethoxycarbonyl-6-formyl-2-methyl-1,4-dihydropyridine-3-carboxylic acid mp 104°~105° C.

(6) 2-Benzyloxyethyl ester of 4-(2-cyanophenyl)-5-ethoxycarbonyl-6-formyl-2-methyl-1,4-dihydropyridine-3-carboxylic acid.

N.M.R. $\delta$ppm (CDCl$_3$): 1.28 (3H, t, J=7 Hz), 2.41 (3H, s), 3.5~3.8 (2H, m), 4.0~4.5 (4H, m), 4.48 (2H, s), 5.48 (1H, s), 6.9~7.5 (10H, m), 10.51 (1H, s)

EXAMPLE 25

(1) To a solution of isopropyl ester of 4-(2-cyanophenyl)-6-formyl-5-methoxycarbonyl-2-methyl-1,4-dihydropyridine-3-carboxylic acid (3.90 g) in acetic acid (20 ml) were added hydroxylamine hydrochloride (0.88 g) and sodium acetate (1.30 g), and the mixture was stirred for an hour at ambient temperature. To the reaction mixture was added acetic anhydride (3.97 g) with stirring, and the stirring was continued for an hour at ambient temperature and for additional 4 hours at 95°~100° C. After the reaction mixture was allowed to stand at ambient temperature, the acetic acid was removed by distillation under reduced pressure. The resultant residue was diluted with water, neutralized with an aqueous solution of sodium bicarbonate and then extracted twice with ethyl acetate. After the combined extract was washed twice with water and dried, the solvent was removed by distillation under reduced pressure to give an oil, which was allowed to stand overnight and pulverized with a small amount of ethyl ether. The powder was washed with isopropyl ether and recrystallized from methanol to give yellowish-orange crystals of isopropyl ester of 6-cyano-4-(2-cyanophenyl)-5-methoxycarbonyl-2-methyl-1,4-dihydropyridine-3-carboxylic acid (1.99 g), mp 198°~200° C.

The following compounds (2)~(6) were obtained in the similar manner to that of Example 25-(1).

(2) Isopropyl ester of 6-cyano-5-methoxycarbonyl-4-(2-methoxycarbonylphenyl)-2-methyl-1,4-dihydropyridine-3-carboxylic acid, mp 121.5°~123° C.

(3) 2-(N-Benzyl-N-methylamino)ethyl ester of 6-cyano-4-(2-cyanophenyl)-5-ethoxycarbonyl-2-methyl-1,4-dihydropyridine-3-carboxylic acid hydrochloride, mp 230° C. (dec.).

(4) 2-Ethoxyethyl ester of 6-cyano-4-(2-cyanophenyl)-5-ethoxycarbonyl-2-methyl-1,4-dihydropyridine-3-carboxylic acid, mp 135°~136° C.

(5) 2-Phenoxyethyl ester of 6-cyano-4-(2-cyanophenyl)-5-ethoxycarbonyl-2-methyl-1,4-dihydropyridine-3-carboxylic acid, mp 170.5°~172° C.

(6) 2-Benzyloxyethyl ester of 6-cyano-4-(2-cyanophenyl)-5-ethoxycarbonyl-2-methyl-1,4-dihydropyridine-3-carboxylic acid, mp 132°~133° C.

EXAMPLE 26

(1) To a solution of isopropyl ester of 4-(2-cyanophenyl)-6-formyl-5-methoxycarbonyl-2-methyl-1,4-dihydropyridine-3-carboxylic acid (3.2 g) in ethanol (65 ml) was added dropwise sodium borohydride (0.33 g) over a period of 10 minutes under cooling at 0° C. with stirring, and the stirring was continued for an hour at the same temperature. After the reaction mixture was slightly acidified with 50% aqueous acetic acid under cooling at 0° C., the ethanol was removed by distillation under reduced prressure. The resultant residue was diluted with water, neutralized with sodium bicarbonate and extracted twice with ethyl acetate. The combined extract was washed with water, an aqueous solution of sodium chloride, and then dried. The solvent was removed by distillation under reduced pressure to give a viscous yellowish oil (3.75 g), which was pulverized with a mixture of ethyl ether and hexane. This powder (3.19 g) was recrystallized from isopropyl ether containing a small amount of methanol to give pale-yellowish crystals of isopropyl ester of 4-(2-cyanophenyl)-6-hydroxymethyl-methoxycarbonyl-2-methyl-1,4-dihydropyridine-3-carboxylic acid (1.97 g), mp 135°~137° C.

The following compounds (2)~(5) were obtained in the similar manner to that of Example 26-(1).

(2) Isopropyl ester of 6-hydroxymethyl-5-methoxycarbonyl-4-(2-methoxycarbonylphenyl)-2-methyl-1,4-dihydropyridine-3-carboxylic acid, mp 144°~145° C.

(3) 2-Ethoxyethyl ester of 4-(2-cyanophenyl)-5-ethoxycarbonyl-6-hydroxymethyl-2-methyl-1,4-dihydropyridine-3-carboxylic acid, mp 127.5°~128.5° C.

(4) 2-Phenoxyethyl ester of 4-(2-cyanophenyl)-5-ethoxycarbonyl-6-hydroxymethyl-2-methyl-1,4-dihydropyridine-3-carboxylic acid, mp 116°~117° C.

(5) 2-Benzyloxyethyl ester of 4-(2-cyanophenyl)-5-ethoxycarbonyl-6-hydroxymethyl-2-methyl-1,4-dihydropyridine-3-carboxylic acid, mp 109°~110° C.

EXAMPLE 27

To a mixture of 2-chloroethyl ester of 5-ethoxycarbonyl-4-(2-cyanophenyl)-6-diethoxymethyl-2-methyl-1,4-dihydropyridine-3-carboxylic acid (5.81 g) and N-benzyl-N-methylamine (5.78 g) in n-propyl alcohol (10 ml) was added a catalytic amount of sodium iodide (0.2 g), and the mixture was refluxed for 4 hours under heating with stirring. After cooling, the solvent was removed by distillation from the reaction mixture under reduced pressure to give a residue, which was dissolved in a mixture of ethyl acetate and water.

The separated organic layer was washed several times with water and then dried. Removal of the solvent gave brownish oil, which was purified by column chromatography on silica gel (230 g) with a mixture of benzene and ethyl acetate (5:2 v/v) as an eluent to give 2-(N-benzyl-N-methylamino)ethyl ester of 4-(2-cyanophenyl)-5-ethoxycarbonyl-6-diethoxymethyl-2-methyl-1,4-dihydropyridine-3-carboxylic acid (5.10 g).

N.M.R. $\delta$ppm (CDCl$_3$): 1.1~1.5 (9H, m), 2.21 (3H, s), 2.40 (3H, s), 2.72 (2H, t, J=6 Hz), 3.53 (2H, s), 3.5~4.5 (8H, m), 5.44 (1H, s), 6.30 (1H, s), 6.87 (1H, broad s), 7.2~7.8 (9H, m).

EXAMPLE 28

A mixture of methyl 2-(2-cyanobenzylidene)-4,4-dimethoxyacetoacetate (11.12 g) and n-propyl 3-aminocrotonate (7.53 g) was stirred at 67° C. for 4 hours, and the stirring was continued at 95.5° C. for 14 hours and at 102° C. for additional 15 hours. The reaction mixture (11.83 g) was dissolved in a proper quantity of diisopropyl ether, and chromatographed on silica gel (300 g) with methylene chloride as an eluent. Fractions containing a desired compound were collected. The solvent was distilled off from the eluate under reduced pressure to give pale yellowish crystals (1.45 g) of n-propyl 6-dimethoxymethyl-2-methyl-4-(2-cyanophenyl)-5-methoxycarbonyl-1,4-dihydropyridine-3-carboxylate, mp 139°-141° C.

N.M.R. $\delta$ppm (CDCl$_3$): 1.78 (3H, t, J=7.3 Hz). 1.64 (2H, sixtet, J=7.3 Hz), 2.42 (3H, s), 3.47 (3H, s), 3.52 (3H, s), 3.73 (3H, s), 4.04 (2H, t, J=7.3 Hz), 5.42 (1H, s), 6.08 (1H, s), 6.77 (1H, m), 7.13-7.38 (1H, m), 7.38-7.71 (3H, m)

EXAMPLE 29

Isobutyl 6-dimethoxymethyl-2-methyl-4-(2-cyanophenyl)-5-methoxycarbonyl-1,4-dihydropyridine-3-carboxylate (17.38 g) was obtained by heating a mixture of methyl 2-(2-cyanobenzylidene)-4,4-dimethoxyacetoacetate (10.82 g) and isobutyl 3-aminocrotonate (8.47 g) in substantially the same manner as that of Example 28, mp 126°-128° C.

N.M.R. $\delta$ppm (CDCl$_3$): 0.74 (3H, d, J=6.5 Hz), 0.87 (3H, d, J=6.5 Hz), 2.02 (1H, m), 2.41 (3H, s), 3.47 (3H, s), 3.52 (3H, s), 3.73 (3H, s), 3.87 (2H, d, J=6.5 Hz), 5.42 (1H, s), 6.06 (1H, s), 6.76 (1H, m), 7.13-7.43 (1H, m), 7.43-7.68 (3H, m)

EXAMPLE 30

Neopentyl 6-dimethoxymethyl-2-methyl-4-(2-cyanophenyl)-5-methoxycarbonyl-1,4-dihydropyridine-3-carboxylate (8.53 g) was obtained by heating a mixture of methyl 2-(2-cyanobenzylidene)-4,4-dimethoxyacetoacetate (10.37 g) and neopentyl 3-aminocrotonate (8.60 g) in substantially the same manner as that of Example 28, mp 130°–131° C.

N.M.R. δppm (CDCl$_3$): 0.85 (9H, s), 2.36 (3H, s), 3.42 (3H, s), 3.46 (3H, s), 3.67 (3H, s), 3.80 (2H, s), 5.37 (1H, s), 6.00 (1H, s), 6.75 (1H, m), 7.00–7.35 (1H, m), 7.35–7.65 (3H, m)

EXAMPLE 31

To a solution (132 ml) of n-propyl 6-dimethoxymethyl-2-methyl-4-(2-cyanophenyl)-5-methoxycarbonyl-1,4-dihydropyridine-3-carboxylate (13.28 g) in acetone was added dropwise 6 N hydrochloric acid (13.2 ml) at 12° C. with stirring, and the stirring was continued for 5.5 hours. The resultant mixture was adjusted to about pH 7 with an aqueous sodium bicarbonate solution. The acetone was distilled off under reduced pressure. The precipitated crystals were collected by filtration and washed with an aqueous sodium chloride solution, water and petroleum ether, successively, and then recrystallized from a mixture of benzene and n-hexane. The crystals were collected by filtration and washed with diethyl ether to give n-propyl 6-formyl-2-methyl-4-(2-cyanophenyl)-5-methoxycarbonyl-1,4-dihydropyridine-3-carboxylate (3.37 g), mp 137.5°–141.0° C.

The mother liquor of the above recrystallization was evaporated to dryness and the residue was chromatographed on silica gel (240 g) with methylene chloride as an eluent to recover the above same product (3.83 g). Total yield was 7.2 g.

N.M.R. δppm (CDCl$_3$): 0.78 (3H, t, J=7 Hz), 1.63 (2H, sixtet, J=7 Hz), 2.43 (3H, s), 3.77 (3H, s), 4.02 (2H, t, J=7 Hz), 5.45 (1H, s), 6.95 (1H, m), 7.2–7.8 (4H, m), 10.51 (1H, s)

EXAMPLE 32

Isobutyl 6-formyl-2-methyl-4-(2-cyanophenyl)-5-methoxycarbonyl-1,4-dihydropyridine-3-carboxylate (6.82 g) was obtained by reacting isobutyl 6-dimethoxymethyl-2-methyl-4-(2-cyanophenyl)-5-methoxycarbonyl-1,4-dihydropyridine-3-carboxylate (20.37 g) with 6 N hydrochloric acid (14 ml) in substantially the same manner as that of Example 31, mp 152.5°–154.5° C.

N.M.R. δppm (CDCl$_3$): 0.76 (3H, d, J=6.5 Hz), 0.82 (3H, d, J=6.5 Hz), 2.02 (1H, m), 2.46 (3H, s), 3.83 (3H, s), 3.90 (2H, d, J=6.5 Hz), 5.53 (1H, s), 7.0 (1H, m), 7.2–7.8 (4H, m), 10.55 (1H, s).

EXAMPLE 33

Neopentyl 6-formyl-2-methyl-4-(2-cyanophenyl)-5-methoxycarbonyl-1,4-dihydropyridine-3-carboxylate (5.83 g) was obtained by reacting neopentyl 6-dimethoxymethyl-2-methyl-4-(2-cyanophenyl)-5-methoxycarbonyl-1,4-dihydropyridine-3-carboxylate (15.56 g) with 6 N hydrochloric acid (14.2 ml) in substantially the same manner as that of Example 31, mp 141.0°–143.0° C.

N.M.R. δppm (CDCl$_3$): 0.86 (9H, s), 2.43 (3H, s), 3.80 (3H, s), 3.85 (2H, s), 5.49 (1H, s), 7.00 (1H, m), 7.3–7.7 (4H, m), 10.50 (1H, s)

EXAMPLE 34

A mixture of n-propyl 6-formyl-2-methyl-4-(2-cyanophenyl)-5-methoxycarbonyl-1,4-dihydropyridine-3-carboxylate (4.29 g), hydroxylamine hydrochloride (0.87 g), sodium acetate (1.13 g) and acetic acid (26 ml) was stirred at ambient temperature for 5 hours. To this mixture was added acetic anhydride (5 g), followed by stirring at ambient temperature for 80 minutes, at 85° C. for 2.5 hours and at 93° C. for additional 9.5 hours. After cooling, the solvent was removed from the reaction mixture under reduced pressure, and to the residue were added an aqueous solution of sodium bicarbonate and methylene chloride. The separated organic layer was washed with water, dried and then evaporated to dryness to give a residue (3.42 g), which was chromatographed on silica gel (100 g) with methylene chloride as an eluent and desired fractions were collected and evaporated. The resultant residue was recrystallized twice from a mixed solvent of methanol and water and then from methylene chloride to give pure crystals (2.29 g) of n-propyl 6-cyano-2-methyl-4-(2-cyanophenyl)-5-methoxycarbonyl-1,4-dihydropyridine-3-carboxylate, mp 150.0°–151.5° C.

N.M.R. δppm (CDCl$_3$): 0.77 (3H, t, J=7 Hz), 1.59 (2H, sixtet, J=7 Hz), 2.37 (3H, s), 3.74 (3H, s), 3.98 (2H, t, J=7 Hz), 5.38 (1H, s), 6.85 (1H, m), 7.0–7.7 (4H, m).

EXAMPLE 35

Isobutyl 6-cyano-2-methyl-4-(2-cyanophenyl)-5-methoxycarbonyl-1,4-dihydropyridine-3-carboxylate (1.81 g) was obtained by reacting isobutyl 6-formyl-2-methyl-4-(2-cyanophenyl)-5-methoxycarbonyl-1,4-dihydropyridine-3-carboxylate (3.39 g) with hydroxylamine hydrochloride (0.89 g), sodium acetate (1.12 g), acetic acid (25 ml) and acetic anhydride (6.24 g) in substantially the same manner as that of Example 34, mp 196.0°–197.5° C.

N.M.R. δppm (CDCl$_3$): 0.75 (3H, d, J=7 Hz), 0.81 (3H, d, J=7 Hz), 1.97 (1H, m), 2.40 (3H, s), 3.78 (3H, s), 3.85 (2H, d, J=7 Hz), 5.41 (1H, s), 7.02 (1H, m), 7.19–7.68 (4H, m).

EXAMPLE 36

Neopentyl 6-cyano-2-methyl-4-(2-cyanophenyl)-5-methoxycarbonyl-1,4-dihydropyridine-3-carboxylate (1.69 g) was obtained by reacting neopentyl 6-formyl-2-methyl-4-(2-cyanophenyl)-5-methoxycarbonyl-1,4-dihydropyridine-3-carboxylate (3.78 g) with hydroxylamine hydrochloride (0.97 g), sodium acetate (1.19 g), acetic acid (25 ml) and acetic anhydride (6.4 g) in substantially the same manner as that of Example 34, mp 173.0°–174.0° C.

N.M.R. δppm (CDCl$_3$): 0.87 (9H, s), 2.41 (3H, s), 3.79 (3H, s), 3.84 (2H, s), 5.44 (1H, s), 6.85 (1H, m), 7.2–7.8 (4H, m).

EXAMPLE 37

To a suspension of n-propyl 6-formyl-2-methyl-4-(2-cyanophenyl)-5-methoxycarbonyl-1,4-dihydropropyridine-3-carboxylate (2.00 g) in ethanol (40 ml) was added sodium borohydride (0.17 g) at −5° to −10° C. over a period of 5 minutes with stirring, and the stirring was continued at the same temperature for 2 hours. To the reaction mixture was added 50% acetic acid (0.6 ml), followed by removal of the solvent under reduced pressure. The residue was dissolved in ethyl acetate, washed with an aqueous solution of sodium chloride and then dried. The solution was evaporated to give crude crystals (2.04 g), which were recrystallized from a mixed solvent of methanol and water to give pure product (1.34 g) of n-propyl 6-hydroxymethyl-2-methyl-4-(2-cyanophenyl)-5-methoxycarbonyl-1,4-dihydropyridine-3-carboxylate, mp 149.0°–152.5° C.

N.M.R. δppm (CDCl$_3$): 0.77 (3H, t, J=7 Hz), 1.61 (2H, sixtet, J=7 Hz), 2.38 (3H, s), 3.63 (3H, s), 3.99 (2H, t, J=7 Hz), 4.79 (2H, s), 5.31 (1H, s), 7.32 (1H, m), 7.1–7.6 (4H, m).

EXAMPLE 38

Isopropyl 6-hydroxymethyl-2-methyl-4-(2-cyanophenyl)-5-methoxycarbonyl-1,4-dihydropyridine-3-carboxylate (1.49 g) was obtained by reacting isopropyl 6-formyl-2-methyl-4-(2-cyanophenyl)-5-methoxycarbonyl-1,4-dihydropyridine-3-carboxylate (2.00 g) with sodium borohydride (0.18 g) in substantially the same manner as that of Example 37, mp 134.5°–137.0° C.

N.M.R. δppm (CDCl$_3$): 0.75 (3H, d, J=7 Hz), 0.81 (3H, d, J=7 Hz), 1.97 (1H, m), 2.39 (3H, s), 2.8 (1H, m), 3.64 (3H, s), 3.86 (2H, d, J=7 Hz), 4.81 (2H, s), 5.35 (1H, s), 7.1–7.7 (5H, m).

EXAMPLE 39

Neopentyl 6-hydroxymethyl-2-methyl-4-(2-cyanophenyl)-5-methoxycarbonyl-1,4-dihydropyridine-3-carboxylate (1.54 g) was obtained by reacting neopentyl 6-formyl-2-methyl-4-(2-cyanophenyl)-5-methoxycarbonyl-1,4-dihydropyridine-3-carboxylate (2.00 g) with sodium borohydride (0.16 g) in substantially the same manner as that of Example 37, mp 178.0°–179.5° C.

N.M.R. δppm (CDCl$_3$): 0.87 (9H, s), 2.38 (3H, s), 3.63 (3H, s), 3.81 (2H, s), 4.78 (2H, s), 5.33 (1H, s), 7.37 (1H, m), 7.1–7.6 (4H, m).

Preparation of the Starting Compounds

Preparation 1

(1) To a solution of 3-nitrobenzaldehyde (7.56 g) and methyl 4,4-dimethoxyacetoacetate (7.93 g) in dried benzene (30 ml) were added acetic acid (0.18 g) and piperidine (0.17 g), and the mixture was heated under reflux for 3.5 hours, while azeotropically removing the water formed therefrom. After adding benzene to the reaction mixture, the solution was washed successively with water, diluted aqueous solution of sodium bicarbonate, water and a saturated aqueous solution of sodium chloride, in turn and then dried. Removal of the solvent under reduced pressure gave an oily residue (15.74 g), which was chromatographed over silica gel (470 g) with a mixture of benzene and ethyl acetate (25:1 by volume as an eluent to give a yellow oil (8.06 g) of methyl 4,4-dimethoxy-2-(3-nitrobenzylidene)acetoacetate (a mixture of cis and trans isomers).

N.M.R. δppm (CDCl$_3$): 3.45 (s), 3.48 (s) (6H), 3.88 (s), 3.91 (s) (3H), 4.90 (s), 5.08 (s) (1H), 7.25–8.4 (5H, m).

The following compounds were obtained in substantially the same manner as that of Preparation 1.

(2) Methyl 4,4-dimethoxy-2-(2-methylbenzylidene)acetoacetate (a mixture of cis and trans isomers).

N.M.R. δppm (CDCl$_3$): 2.33 (3H, s), 3.23 (s), 3.42 (s) (6H), 3.64 (s), 3.79 (s) (3H), 4.53 (s), 5.04 (s) (1H), 6.8–7.4 (4H, m), 7.97 (s), 8.09 (s) (1H)

(3) Methyl 2-(2-chlorobenzylidine)-4,4-dimethoxyacetoacetate (a mixture of cis and trans isomers).

N.M.R. δppm (CDCl$_3$): 3.28 (s), 3.41 (s) (6H), 3.71 (s), 3.81 (s) (3H), 4.68 (s), 5.08 (s) (1H), 7–7.5 (4H, m), 8.02 (s), 8.12 (s) (1H).

(4) Methyl 4,4-dimethoxy-2-(4-pyridylmethylene)acetoacetate (a mixture of cis and trans isomers).

N.M.R. δppm (CDCl$_3$): 3.41 (s), 3.48 (s) (6H), 3.82 (s), 3.89 (s) (3H), 4.82 (s), 5.06 (s) (1H), 7.1–7.4 (2H, m), 7.73 (s), 7.83 (s) (1H), 8.5–8.8 (2H, m).

(5) Methyl 2-(2-trifluoromethylbenzylidene)-4,4-dimethoxyacetoacetate (a mixture of cis and trans isomers).

N.M.R δppm (CDCl$_3$): 3.28 (s), 3.42 (s) (6H), 3.61 (s), 3.84 (s) (3H), 4.62 (s), 5.06 (s) (1H), 7.2–7.8 (4H, m), 8.0–8.14 (1H, m).

(6) Methyl 4,4-dimethoxy-2-(2-methoxybenzylidene)acetoacetate (a mixture of cis and trans isomers).

N.M.R. δppm (CDCl$_3$): 3.39 (s), 3.47 (s) (6H), 3.78 (s), 3.88 (s) (6H), 4.77 (s), 5.16 (s) (1H), 6.7–7.2 (m), 7.3–7.9 (m) (4H), 8.15 (s), 8.23 (s) (1H).

(7) Methyl 2-(2-allyloxybenzylidine)-4,4-dimethoxyacetoacetate (a mixture of cis and trans isomers).

N.M.R. δppm (CDCl₃): 3.3 (s) ⎫
                      3.4 (s) ⎭ (6H), 3.73 (s) ⎫ (3H), 4.54 (2H, m),
3.78 (s) ⎭

4.71 (s) ⎫ (1H), 5.1–5.5 (5H, m),
5.07 (s) ⎭

5.8–6.22 (1H, m), 6.7–7.0 (m) ⎫ (4H),
                   7.2–7.4 (m) ⎭

8.14 (s) ⎫ (1H).
8.23 (s) ⎭

(8) Methyl 4,4-dimethoxy-2-(2-thenylidene)acetoacetate (a mixture of cis and trans isomers).

N.M.R. δppm (CDCl₃): 3.45 (6H, s), 3.88 (s) ⎫ (3H),
                                    3.95 (s) ⎭

5.11 (s) ⎫ (1H), 7–7.8 (3H, m),
5.17 (s) ⎭

7.93 (s) ⎫ (1H).
8.06 (s) ⎭

(9) Methyl 2-(2,4-dichlorobenzylidine)-4,4-dimethoxyacetoacetate (a mixture of cis and trans isomers).

N.M.R. δppm (CDCl₃): 3.39 (s) ⎫ (6H),
                      3.47 (s) ⎭

3.77 (s) ⎫ (3H), 4.77 (s) ⎫ (1H),
3.88 (s) ⎭       5.01 (s) ⎭

7.2–7.5 (3H, m), 7.97 (s) ⎫ (1H).
                  8.08 (s) ⎭

(10) Methyl 2-(3,4-dichlorobenzylidene)-4,4-dimethoxyacetoacetate (one of cis and trans isomers), mp 86.5°–87.5° C.

(11) Methyl 4,4-dimethoxy-2-(3,4-dimethoxybenzylidene)acetoacetate (a mixture of cis and trans isomers).

N.M.R. δppm (CDCl₃): 3.43 (s) ⎫ (6H),
                      3.49 (s) ⎭

3.87 (s) ⎫
3.92 (s) ⎬ (9H), 4.87 (s) ⎫ (1H),
3.93 (s) ⎪       5.10 (s) ⎭
3.97 (s) ⎭

6.6–7.4 (3H, m), 7.80 (s) ⎫ (1H).
                  7.89 (s) ⎭

(12) 2-Phenoxyethylester of 2-(2-trifluoromethylbenzylidene)acetoacetic acid (a mixture of cis and trans isomers).

N.M.R. δppm (CDCl₃): 2.18 (s) ⎫ (3H),
                      2.47 (s) ⎭

3.9–4.9 (4H, m), 6.8–8.2 (10H, m).

(13) 2-Chloroethyl ester of 2-(2-trifluoromethylbenzylidene)acetoacetic acid (a mixture of cis and trans isomers).

N.M.R. δppm (CDCl₃): 2.18 (s) ⎫ (3H),
                      2.46 (s) ⎭

3.50 (t, J=6Hz) ⎫ (2H),
3.76 (t, J=6Hz) ⎭

4.34 (t, J=6Hz) ⎫ (2H), 7.3–7.9 (4H, m),
4.51 (t, J=6Hz) ⎭

7.95 (q, J=2.2Hz) ⎫ (1H).
8.04 (q, J=2.2Hz) ⎭

(14) 2-Ethoxyethyl ester of 2-(2-trifluoromethylbenzylidene)acetoacetic acid (a mixture of cis and trans isomers).

N.M.R. δppm (CCl₄): 1.10 (t, J=7Hz) ⎫ (3H),
                     1.18 (t, J=7Hz) ⎭

2.11 (s) ⎫ (3H), 3.1–3.8 (4H, m),
2.38 (s) ⎭

4.1–4.5 (2H, m), 7.3–8.0 (5H, m).

(15) 2-Benzyloxyethyl ester of 2-(2-trifluoromethylbenzylidene)acetoacetic acid (a mixture of cis and trans isomers).

N.M.R δppm (CCl₄): 2.10 (s) ⎫ (3H), 3.4–3.9
                    2.37 (s) ⎭       (2H,m), 4.1–4.7 (m) ⎫
4.37 (s)    ⎬ (4H),           7.2–8.0
4.53 (s)    ⎭                 (10H, m)

Preparation 2

(1) A solution of 2-cyanobenzaldehyde (6.56 g), methyl 4,4-dimethoxyacetoacetate (7.93 g), acetic acid (0.18 g) and piperidine (0.17 g) in benzene (40 ml) was refluxed for 5 hours with stirring under azeotropic dehydration. After cooling, the reaction mixture was diluted with benzene, washed with water, an aqueous solution of sodium bicarbonate, and then dried over magnesium sulfate. After removal of the solvent, the residual oil (13.75 g) was subjected to column chromatography on silica gel (420 g) with a mixture of benzene and ethyl acetate (20:1 V/V) as an eluent. The fractions containing a desired compound were collected and the solvent was removed by distillation under reduced pressure to give a yellowish oil of methyl 2-(2-cyanobenzylidene)-4,4-dimethoxy acetoacetate (a mixture of cis and trans isomers) (10.11 g).

N.M.R.

| δppm (CDCl₃): | 3.41 (s), 3.49 (s) | (6H), | 3.79 (s), 3.92 (s) | (3H), |
| --- | --- | --- | --- | --- |
| 4.83 (s), 5.11 (s) | (1H), | 7.5~8.0 (4H, m), | 8.07 (s), 8.16 (s) | (1H) |

The following starting compounds (2)~(6) were obtained in the similar manner to that of Preparation 2-(1).

(2) Methyl 2-(2-methoxycarbonylbenzylidene)-4,4-dimethoxyacetoacetate (a mixture of cis and trans isomers)

N.M.R.
δppm (CDCl₃):
| 3.26 (s), 3.43 (s), 3.56 (s) | (6H) |
| --- | --- |
| 3.83 (s), 3.87 (s), 3.89 (s) | (6H) |
| 4.67 (s) | (1H) |
| 5.13 (s) | |
| 7.2~8.1 | (4H, m) |
| 8.39 (s), 8.46 (s) | (1H) |

(3) 2-Chloroethyl 2-(2-cyanobenzylidene)acetoacetate (a mixture of cis and trans isomers).

N.M.R.
δppm (CDCl₃):
| 2.34 (s), 2.50 (s) | (3H) |
| --- | --- |
| 3.6~3.9 | (2H, m) |
| 4.3~4.6 | (2H, m) |
| 7.25~7.9 | (4H, m) |
| 8.00 (s), 7.88 (s) | (1H) |

(4) 2-Ethoxyethyl 2-(2-cyanobenzylidene)acetoacetate (a mixture of cis and trans isomers).

N.M.R.
δppm (CDCl₃):
| 1.15 (t, J=6.5 Hz), 1.23 (t, J=6.5 Hz) | (3H) |
| --- | --- |
| 2.35 (s), 2.48 (s) | (3H) |
| 3.58 (2H, q, J=6.5 Hz) | |
| 3.7~3.8 | (2H, m) |
| 4.3~4.5 | (2H, m) |
| 7.30~8.05 | (4H, m) |
| 7.95 (s), 7.91 (s) | (1H) |

(5) 2-Phenoxyethyl 2-(2-cyanobenzylidene)acetoacetate (one of cis and trans isomers), mp 102.5°~104° C.

(6) 2-Benzyloxyethyl 2-(2-cyanobenzylidene)acetoacetate (a mixture of cis and trans isomers).

N.M.R.
δppm (CDCl₃):
| 2.29 (s), 2.43 (s) | (3H), |
| --- | --- |
| 3.50~3.85 | (2H, m) |
| 4.20~4.60 | (2H, m) |
| 4.55 (s), 4.44 (s) | (2H) |
| 7.15~7.85 | (9H, m) |
| 7.96 (s), 7.83 (s) | (1H) |

Preparation 3

A benzene solution (120 ml) of 2-cyanobenzaldehyde (30.97 g), methyl 4,4-dimethoxyacetoacetate (46.14 g), acetic acid (2.3 g) and piperidine (2.4 g) was refluxed under heating for 8 hours. After addition of benzene (80 ml) and washing with water, the solution was treated with an activated charcoal. The evaporated residue was chromatographed on silica gel (500 g) with methylene chloride as an eluent. The fractions containing a desired compound were collected and evaporated to give methyl 2-(2-cyanobenzylidine)-4,4-dimethoxyacetoacetate (25.16 g).

| N.M.R. δppm(CDCl₃): | 3.41 (s), 3.50 (s) | (6H), | 3.69 (s), 3.92 (s) | (3H), |
| --- | --- | --- | --- | --- |
| 4.83 (s), 5.10 (s) | (1H), | 7.40-7.90 (4H, m), | 8.04 (s), 8.17 (s) | (1H) |

What is claimed is:
1. A compound of the formula:

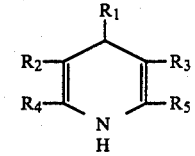

wherein
R₁ is unsubstituted phenyl or phenyl having one substituent selected from halogen, nitro, lower alkyl, halo(lower)alkyl, lower alkoxy, lower alkenyloxy, cyano, trifluoromethyl and lower alkoxycarbonyl or phenyl having two substituents selected from chloro-nitro, dihalo or dimethoxy, R₂ and R₃ are each, same or different, esterified carboxy selected from lower alkoxycarbonyl, hydroxy(lower)alkoxycarbonyl, lower alkoxy(lower)alkoxycarbonyl, phenyl(lower)alkoxy(lower)alkoxycarbonyl, phenoxy(lower)alkoxycarbonyl, N,N-di(lower)alkylamino(lower)alkoxycarbonyl and N-lower alkyl-N-phenyl(lower)alkylamino(lower)alkoxycarbonyl, and R₄ or R₅ is cyano or cyano(lower)alkyl and the other is the same, hydrogen or lower alkyl.

2. A compound according to claim 1, wherein
R₁ is phenyl, nitrophenyl, halophenyl, halo and nitrodisubstituted phenyl, trifluoromethylphenyl, cyanophenyl, lower alkenyloxyphenyl or lower alkoxycarbonylphenyl, R₂ is lower alkoxycarbonyl, R₃ is lower alkoxycarbonyl, lower alkoxy(lower)alkoxycarbonyl, benzyloxy-ethoxycarbonyl, phenoxy(lower)alkoxycarbonyl, N,N-di(lower)alkylamino(lower)alkoxycarbonyl or N-(lower)alkyl-N-phenyl(lower)alkylamino(lower)alkoxycarbonyl, and the other of R₄ or R₅ is lower alkyl.

3. A compound according to claim 2 that is diethyl 2-methyl-4-(2-chlorophenyl)-6-cyano,-1,4-dihydropyridine-3,5-dicarboxylate.

4. A compound according to claim 2 that is diethyl 2-methyl-4-(2-trifluoromethylphenyl)-6-cyano-1,4-dihydropyridine-3,5-dicarboxylate.

5. A compound according to claim 2, wherein R₁ is nitrophenyl, R₂ and R₃ are each lower alkoxycarbonyl, R₄ is lower alkyl and R₅ is cyano.

6. A compound according to claim 5 that is diethyl 2-methyl-4-(2-nitrophenyl)-6-cyano-1,4-dihydropyridine-3,5-dicarboxylate.

7. A compound according to claim 5 that is diethyl 2-methyl-4-(3-nitrophenyl)-6-cyano-1,4-dihydropyridine-3,5-dicarboxylate.

8. A compound according to claim 2 wherein R₁ is 2-nitrophenyl, R₂ is ethoxycarbonyl, R₃ is 2-ethoxyethoxycarbonyl, benzyloxy(lower)alkoxycarbonyl, or 2-phenoxyethoxycarbonyl, R₄ is cyano and R₅ is methyl.

9. A compound according to claim 2 wherein R₁ is 3-nitrophenyl, R₂ is ethoxycarbonyl, R₃ is 2-ethoxyethoxycarbonyl, 2-(N,N-diethylamino)ethoxycarbonyl or 2-(N-methyl-N-benzylamino)ethoxycarbonyl, R₄ is cyano and R₅ is methyl.

10. A compound according to claim 2 that is diethyl 2-methyl-4-(2-chloro-5-nitrophenyl)-6-cyano-1,4-dihydropyridine-3,5-dicarboxylate.

11. A compound according to claim 2 that is diethyl 2-methyl-4-(2-nitrophenyl)-6-cyanomethyl-1,4-dihydropyridine-3,5-dicarboxylate.

12. A compound according to claim 2 that is diethyl 2-methyl-4-(2-allyloxyphenyl)-6-cyano-1,4-dihydropyridine-3,5-dicarboxylate.

13. A compound according to claim 5 that is dimethyl 2-methyl-4-(2-nitrophenyl)-6-cyano-1,4-dihydropyridine-3,5-dicarboxylate.

14. A compound according to claim 5 that is isopropyl 2-methyl-4-(2-nitrophenyl)-5-methoxycarbonyl-6-cyano-1,4-dihydropyridine-3-carboxylate.

15. A compound according to claim 5 that is dimethyl 2-methyl-4-(3-nitrophenyl)-6-cyano-1,4-dihydropyridine-3,5-dicarboxylate.

16. A compound according to claim 2 that is dimethyl 2-methyl-4-(2-cyanophenyl)-6-cyano-1,4-dihydropyridine-3,5-dicarboxylate.

17. A compound according to claim 2 that is diethyl 2-methyl-4-(2-methoxycarbonylphenyl)-6-cyano-1,4-dihydropyridine-3,5-dicarboxylate.

18. A compound according to claim 5 wherein R₁ is 3-nitrophenyl.

19. A compound according to claim 18 that is isopropyl-6-cyano-5-methoxycarbonyl-2-methyl-4-(3-nitrophenyl)-1,4-dihydropyridine-3-carboxylate.

20. A compound of the formula:

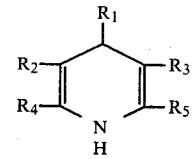

wherein
R₁ is unsubstituted phenyl or phenyl having one substituent selected from halogen, nitro, lower alkyl, halo(lower)alkyl, trifluoromethyl, lower alkoxy, lower alkenyloxy, cyano and lower alkoxycarbonyl, R₂ and R₃ are each, same or different, esterified carboxy selected from lower alkoxycarbonyl, hydroxy(lower)alkoxycarbonyl, lower alkoxy(lower)alkoxycarbonyl, phenyl(lower)alkoxy(lower)alkoxycarbonyl, phenoxy(lower)alkoxycarbonyl, N,N-(di)(lower)alkylamino(lower)alkoxycarbonyl and N-(lower)alkyl-N-phenyl(lower)alkylamino(lower)alkoxycarbonyl, R₄ is lower alkyl, R₅ is cyano or cyano(lower)alkyl.

21. A compound according to claim 20 wherein R₁ is phenyl, halophenyl, nitrophenyl, halo- and nitrodisubstituted phenyl, trifluoromethylphenyl, lower alkylphenyl, lower alkoxyphenyl, lower alkenyloxyphenyl, cyanophenyl and lower alkoxycarbonylphenyl, R₂ is lower alkoxycarbonyl, and
R₅ is cyano.

22. A compound according to claim 2 that is 3-(2-benzyl-oxyethoxycarbonyl)2-methyl-4-(3-nitrophenyl)-5-ethoxycarbonyl-6-cyano-1,4-dihydropyridine.

23. A method for effecting vasodilation in humans or mammals in need of such treatment which comprises administering thereto an effective amount of the compound of claim 1.

24. A method for effecting vasodilation in humans or mammals in need of such treatment which comprises administering thereto an oral daily dose of 0.1 to 500 mg. or 10 to 25% thereof intravenously of the compound of claim 1.

25. A method for effecting vasodilation in humans or mammals in need of such treatment which comprises administering thereto an oral daily dose of 1 to 50 mg. or 10 to 25% thereof intravenously of the compound of claim 1.

26. A method for effecting vasodilation in humans or mammals in need of such treatment which comprises administering thereto an oral daily dose of 1 μg to 10 mg/kg. or 10 to 25% thereof intravenously of the compound of claim 1.

27. A method for effecting vasodilation in humans or mammals in need of such treatment which comprises administering thereto an oral daily dose of 0.5 to 5 mg/kg or 10 to 25% thereof intravenously of the compound of claim 1.

* * * * *